(12) United States Patent
Geigle et al.

(10) Patent No.: US 11,788,228 B2
(45) Date of Patent: Oct. 17, 2023

(54) METHODS FOR PROCESSING LIGNOCELLULOSIC MATERIAL

(71) Applicant: CMBlu Energy AG, Alzenau (DE)

(72) Inventors: Peter Geigle, Alzenau (DE); Jan Hartwig, Alzenau (DE)

(73) Assignee: CMBlu Energy AG, Alzenau (DE)

( * ) Notice: Subject to any disclaimer, the term of this patent is extended or adjusted under 35 U.S.C. 154(b) by 478 days.

(21) Appl. No.: 16/480,958

(22) PCT Filed: Feb. 13, 2018

(86) PCT No.: PCT/EP2018/053595
§ 371 (c)(1),
(2) Date: Jul. 25, 2019

(87) PCT Pub. No.: WO2018/146341
PCT Pub. Date: Aug. 16, 2018

(65) Prior Publication Data
US 2019/0390405 A1    Dec. 26, 2019

(30) Foreign Application Priority Data

Feb. 13, 2017  (WO) ................. PCT/EP2017/000198
Apr. 7, 2017   (WO) ................. PCT/EP2017/000463
(Continued)

(51) Int. Cl.
*D21C 9/04*    (2006.01)
*D21C 11/00*   (2006.01)
(Continued)

(52) U.S. Cl.
CPC .......... *D21C 11/0007* (2013.01); *C07C 46/10* (2013.01); *C07C 303/06* (2013.01);
(Continued)

(58) Field of Classification Search
CPC ....... C08B 3/00; D21C 11/0007; D21C 3/022; D21C 9/004
See application file for complete search history.

(56) References Cited

U.S. PATENT DOCUMENTS 1,916,627 A    7/1933  Mersch
1,963,383 A    6/1934  Rogers
(Continued)

FOREIGN PATENT DOCUMENTS

CN    101475758 A    7/2009
CN    102040483 A    5/2011
(Continued)

OTHER PUBLICATIONS

Moodley B., et al., "The electro-oxidation of lignin in Sappi Saiccor dissolving pulp mill effluent," Internet Citation, 33-40 (2011).
(Continued)

*Primary Examiner* — Jacob T Minskey
(74) *Attorney, Agent, or Firm* — HARNESS DICKEY & PIERCE P.L.C.

(57) ABSTRACT

The invention relates to novel methods for processing lignocellulosic material. More specifically, the invention proves an integrated approach for processing cellulose to obtain paper and pulp and valorizing lignin to obtain value-added chemicals and products.

26 Claims, 3 Drawing Sheets

(30) Foreign Application Priority Data

Oct. 5, 2017 (WO) .................. PCT/EP2017/001177
Oct. 11, 2017 (WO) .................. PCT/EP2017/075987

(51) Int. Cl.
| | |
|---|---|
| *C07C 46/10* | (2006.01) |
| *C07C 303/06* | (2006.01) |
| *D21C 3/02* | (2006.01) |
| *D21C 9/00* | (2006.01) |
| *D21F 3/02* | (2006.01) |

(52) U.S. Cl.
CPC ............. *D21C 3/022* (2013.01); *D21C 9/004* (2013.01); *D21F 3/02* (2013.01); *C07C 2603/24* (2017.05)

(56) References Cited

U.S. PATENT DOCUMENTS

| | | | |
|---|---|---|---|
| 3,646,071 A | 2/1972 | Frey et al. | |
| 4,124,606 A | 11/1978 | Anello et al. | |
| 4,420,644 A | 12/1983 | Huibers et al. | |
| 4,579,943 A * | 4/1986 | Kamide ................ | C08B 11/12 442/414 |
| 5,002,634 A | 3/1991 | Dimmel et al. | |
| 5,049,477 A | 9/1991 | Nakamura et al. | |
| 5,723,675 A | 3/1998 | Joo et al. | |
| 5,932,752 A | 8/1999 | Keshavaraja et al. | |
| 5,944,953 A | 8/1999 | Lavoie et al. | |
| 11,008,284 B2 | 5/2021 | Krawczyk et al. | |
| 11,225,756 B2 | 1/2022 | Krawczyk et al. | |
| 2004/0244925 A1 | 12/2004 | Tarasenko | |
| 2007/0073076 A1* | 3/2007 | Lewis ................... | C07F 7/025 556/482 |
| 2010/0086675 A1 | 4/2010 | Berta et al. | |
| 2011/0144337 A1 | 6/2011 | Santhosh et al. | |
| 2011/0268652 A1 | 11/2011 | Machhammer et al. | |
| 2013/0079566 A1* | 3/2013 | Lin ....................... | B01J 23/34 585/242 |
| 2013/0116424 A1* | 5/2013 | Peterson .............. | C07D 307/06 549/507 |
| 2013/0232852 A1 | 9/2013 | Peterson et al. | |
| 2013/0232853 A1 | 9/2013 | Peterson et al. | |
| 2015/0243991 A1 | 8/2015 | Huskinson et al. | |
| 2016/0009621 A1 | 1/2016 | Blair | |
| 2016/0013497 A1 | 1/2016 | Jones et al. | |
| 2016/0032525 A1 | 2/2016 | Kurple et al. | |
| 2016/0130752 A1 | 5/2016 | Stigsson et al. | |
| 2016/0197371 A1 | 7/2016 | Takechi | |
| 2018/0079721 A1 | 3/2018 | Armand et al. | |
| 2018/0097249 A1 | 4/2018 | Narayan et al. | |
| 2018/0099917 A1 | 4/2018 | Anthony et al. | |
| 2019/0152902 A1 | 5/2019 | Krawczyk et al. | |
| 2019/0390405 A1 | 12/2019 | Geigle et al. | |
| 2019/0393506 A1 | 12/2019 | Hartwig et al. | |
| 2020/0014040 A1 | 1/2020 | Kerker et al. | |
| 2020/0283380 A1 | 9/2020 | Krawczyk et al. | |
| 2021/0020943 A1 | 1/2021 | Hartwig et al. | |
| 2021/0024453 A1 | 1/2021 | Hartwig et al. | |
| 2021/0276945 A1 | 9/2021 | Krawczyk et al. | |

FOREIGN PATENT DOCUMENTS

| | | |
|---|---|---|
| CN | 103000924 A | 3/2013 |
| FR | 3030561 A1 | 6/2016 |
| GB | 1502275 A | 3/1978 |
| JP | S51100064 A | 9/1976 |
| JP | S51138666 A | 11/1976 |
| JP | S52144662 A | 12/1977 |
| JP | H9227499 A | 9/1997 |
| JP | 2001507404 A | 6/2001 |
| JP | 3813864 B2 | 8/2006 |
| JP | 2011057636 A | 3/2011 |
| JP | 2013254685 A | 12/2013 |
| JP | 2015534708 A | 12/2015 |
| JP | 2019503619 A | 2/2019 |
| JP | 2019513831 A | 5/2019 |
| KR | 20150004218 U | 11/2015 |
| RO | 76126 A2 | 5/1981 |
| SU | 1129204 A1 | 12/1984 |
| WO | 1998/13538 A1 | 4/1998 |
| WO | WO-2009083940 A2 | 7/2009 |
| WO | WO-2011131959 A1 | 10/2011 |
| WO | 2014052682 A2 | 4/2014 |
| WO | WO-2014081235 A1 | 5/2014 |
| WO | WO-2014204985 A1 | 12/2014 |
| WO | WO-2015048550 A1 | 4/2015 |
| WO | 2015148357 A1 | 10/2015 |
| WO | WO-2016144909 A1 | 9/2016 |
| WO | 2017174098 A1 | 10/2017 |
| WO | 2017174206 A1 | 10/2017 |
| WO | 2017174207 A1 | 10/2017 |
| WO | 2018146341 A1 | 8/2018 |
| WO | WO-2018/146343 A1 | 8/2018 |
| WO | WO-2018146344 A1 | 8/2018 |

OTHER PUBLICATIONS

Zakzeski J., et al., "The Catalytic Valorization of Lignin for the Production of Renewable Chemicals," Chemical Reviews, 110(6): 3552-3599 (2010).
International Search Report from PCT Application No. PCT/EP2018/053595 dated Jun. 12, 2018.
Written Opinion from PCT Application No. PCT/EP2018/053595 dated Jun. 12, 2018.
Wedege K., et al., "Organic Redox Species in Aqueous Flow Batteries: Redox Potentials, Chemical Stability and Solubility," Scientific Reports, 6(1) (2016).
Written Opinion from PCT Application No. PCT/EP2018/053596 dated May 3, 2018.
U.S. Appl. No. 16/091,437, filed Oct. 4, 2018.
U.S. Appl. No. 16/091,436, filed Oct. 4, 2018.
U.S. Appl. No. 16/484,301, filed Aug. 7, 2019.
U.S. Appl. No. 16/968,732, filed Aug. 10, 2020.
Vandenberghe A., and Willems J.F., "Sulphonation of Alkylhydroquinones," Bull. Soc. Chim. Belges, 74(9-10): 397-406 (1965).
Hu L., et al., "Methods to Improve Lignin's Reactivity as a Phenol Substitute and as Replacement for Other Phenolic Compounds: A Brief Review," Bio Resources, 6(3): 3515-3525 (2011).
International Search Report issued in PCT/EP2017/000461 dated Dec. 6, 2017.
International Search Report issued in PCT/EP2017/000462 dated Sep. 6, 2017.
Written Opinion issued in PCT/EP2017/000461 dated Dec. 6, 2017.
Written Opinion issued in PCT/EP2017/00462 dated Sep. 6, 2017.
Zakzeski, J et al., "The Catalytic Valorization of Lignin for the Production of Renewable Chemicals," Chem. Rev., 110: 3552-3599 (2010).
Office Action from corresponding Eurasian Patent Application No. 201892234 dated Sep. 10, 2019.
Azarov, V.I., "Khimiya drevesiny i sinteticheskikh polimerov," Sankt-Petersburg, pp. 366-373 (1999).
Brauns, F.E., "Khimiya lignina," Moscow, pp. 558-570 (1964).
Office Action dated Mar. 20, 2020 issued in U.S. Appl. No. 16/091,436.
Restriction Requirement from U.S. Appl. No. 16/091,437 dated Jun. 15, 2020.
International Search Report from PCT Application No. PCT/EP2018/053596 dated May 3, 2018.
International Search Report from PCT Application No. PCT/EP2018/053597 dated May 8, 2018.
Written Opinion from PCT Application No. PCT/EP2018/053597 dated May 8, 2018.
Huber, G. W., et al., "Synthesis of Transportation Fuels from Biomass: Chemistry, Catalysts, and Engineering," Chemical Reviews, American Chemical Society, 106: 4044-4098 (2006).

(56) References Cited

OTHER PUBLICATIONS

Moodley, B. et al., "The electro-oxidation of lignin in Sappi Saiccor dissolving pulp mill effluent," 37(1): 33-40 (2011).
Xu, Ch. et al., "Lignin depolymerisation strategies: towards valuable chemicals and fuels," Chem Soc Rev. 43: 7485-7500 (2014).
Zhou, Y. et al., "Methods to Improve Lignin's Reactivity as a Phenol Substitute and as Replacement for Other Phenolic Compounds: A Brief Review," BioResources, 6(3): 1-11 (2011).
Wedege, K., et al., "Organic Redox Species in Aqueous Flow Batteries: Redox Potentials, Chemical Stabilitiy and Solubility," Scientific Reports, 6(1): 1-13 (2016).
International Search Report from PCT Application No. PCT/EP2019/053602 dated Apr. 3, 2019.
Written Opinion from PCT Application No. PCT/EP2019/053602 dated Apr. 3, 2019.
Smook, Gary A., "Handbook for Pulp and Paper Technologists," Angus Wilde Publications, 2nd edition, chapters 7 and 8 (1992).
Denisov, E.T., and Metelitsa, D.I., "Oxidation of Benzene," Russ. Chem. Rev., 37 (656), 1968.
www.chem.uiuc.edu, "Oxidation of Phenols," (1999).
Dominguez-Ramos, A., et al., "Electrochemical Oxidation of Lignosulfonate: Total Organic Carbon Oxidation Kinetics," Ind. Eng. Chem. Res., 47(24): 9848-9853 (2008).
Duval, A., et al., "Fractionation of lignosulfonates: comparison of ultrafiltration and ethanol solubility to obtain a set of fractions with distinct properties," Holzforschung, 69(2): 127-134 (2015).
Gierer, J., "Chemistry of delignification, Part 1: General concept and reactions during pulping," Wood Science and Technology, 19: 289-312 (1985).
Gierer, J., "Chemistry of delignification: Part 2: Reactions of lignins during bleaching," Wood Science and Technology, 20: 1-33 (1986).
Miyazawa, T., et al., "Highly regioselective propanoylation of dihydroxybenzenes mediated by *Candida antarctica* lipase B in organic solvents," Tetrahedron Letters, 49: 175-178 (2008).
Weatherbee, C., et al., "A New Approach to Tertiary β-Chloroalkylamines. Synthesis of β-Chloroalkylaminomethylhydroquinones[1]", Journal of Organic Chemistry, 21(10): 1138-1141 (1956).
Zhang, S., et al., "An Organic Electroactive Material for Flow Batteries," Electrochimica Acta, 190: 737-743 (2016).
Weetall, H. H., et al., "Biotechnology and Bioengineering—A Direct Fuel Cell for the Production of Electricity from Lignin," vol. 27, No. 7, p. 1-11 (1985).
Mark, H. B., and Atkin, C. L., "Electrode Reactions of Aromatica Compounds in Strong Acid Solutions," Analytical Chemistry, 36(3): 514-520.
Arai, G., and Onozuka, M., "The Reaction of 1, 4-Naphthoquinone-2-sulfonate with Sodium Sulfite," The Chemical Society of Japan, 12: 1899-1903, (1981).
Office Action from corresponding U.S. Appl. No. 16/480,956 dated Aug. 17, 2021.
Office Action from corresponding U.S. Appl. No. 16/480,958 dated Aug. 23, 2021.
Dorn, Bv H. W., et al., "Certain Derivatives of the Ethers of Hydroxyhydroquinone," Journal of the American Chemical Society, 61: 144-147 (1939).
Yang, B., et al., "An Inexpensive Aqueous Flow Battery for Large-Scale Electrical Energy Storage Based on Water-Soluble Organic Redox Couples," Journal of the Electrochemical Society, 161(9): A1371-A1380 (2014).
Office Action from corresponding Japanese Application No. 2019-503619 dated Feb. 8, 2022.
Fitzky, H.G., et al., "Paramagnetic electron resonance measurements of short-lived, substituted p-benzosemiquinones," Photographische Korrespondenz, 103(4): 60-64 (1967).
Office Action from corresponding U.S. Appl. No. 16/484,301 dated Apr. 22, 2022.
U.S. Appl. No. 17/177,567, filed Feb. 17, 2021.
U.S. Appl. No. 16/967,898, filed Aug. 6, 2020.
U.S. Appl. No. 17/842,079, filed Jun. 16, 2022.

Kaiho, A. et al., "Construction of the di(trimethylolpropane) cross linkage and the phenylnaphthalene structure coupled with selective ?—O—4 bond cleavage for synthesizing lignin-based epoxy resins with a controlled glass transition temperature," Green Chem., 18: 6526-6535 (2016).
Klein, I. et al., "Lignin depolymerization over Ni/C catalyst in methanol, a continuation: effect of substrate and catalyst loading," Catal. Sci. Technol., 5: 3242-3245 (2015).
Restriction Requirement issued in corresponding U.S. Appl. No. 16/484,301 dated Sep. 29, 2021.
Office Action issued in corresponding U.S. Appl. No. 16/484,301 dated Oct. 27, 2022.
Restriction Requirement issued in U.S. Appl. No. 16/968,732 dated Mar. 17, 2022.
Office Action issued in U.S. Appl. No. 16/968,732 dated Jun. 24, 2022.
Office Action issued in U.S. Appl. No. 16/968,732 dated Nov. 30, 2022.
Restriction Requirement issued in corresponding U.S. Appl. No. 16/480,956 dated Apr. 28, 2021.
Restriction Requirement issued in corresponding U.S. Appl. No. 16/091,436 dated Aug. 1, 2019.
Interview Summary issued in corresponding U.S. Appl. No. 16/091,436 dated Jun. 4, 2020.
Office Action issued in corresponding U.S. Appl. No. 16/091,437 dated Nov. 25, 2020.
Office Action issued in corresponding U.S. Appl. No. 16/091,437 dated May 4, 2021.
Yang et al., "High-Performance Aqueous Organic Flow Battery with Quinone-Based Redox Couples at Both Electrodes", Journal of The Electrochemical Society 163(7):A1442-A1449 (2016).
Search Report issued in corresponding EP Appln. No. EP22173705.9 dated Oct. 28, 2022.
Office Action issued in corresponding U.S. Appl. No. 16/967,898 dated Dec. 6, 2022.
Office Action issued in corresponding JP Appln. No. 2021-142062 dated Mar. 16, 2023.
Search Report issued in corresponding EP Appln. No. 22203539.6 dated Mar. 15, 2023.
Search Report issued in corresponding EP Appln. No. 22203648.5 dated Mar. 17, 2023.
Chowdhury Pankaj et al., "Aqueous Photoelectrochemical Reduction of Anthraquinone Disulfonate at Organic Polymer Films", Macromolecular Chemistry and Physics, 217(10):1119-1127 (2016).
Corby B. W. et al., "Clean-chemistry sulfonation of aromatics", J. Chem. Research (S), 26-327 (2002).
Abraham, Ignatious et al. "Recent Advances in 1,4-Benzoquinone Chemistry", Journal of the Brazilian Chemical Society, 22(3):385-421, XP93023984 (2011).
Cheng, Yu-Ting et al. "Production of targeted aromatics by using Diels-Alder classes of reactions with furans and olefins over ZSM-5", Green Chemistry, 14(1):3114-3125, XP055068442 (2012).
Gosselink, Richard et al. "Lignin as a renewable aromatic resource for the chemical industry (Thesis)", 1-196, XP93023331 (2011).
Gosselink, Richard et al. "Lignin as a renewable aromatic resource for the chemical industry (Mini-symposium organized by Wageningen UR Lignin Platform)", Wageningen Contents, 1-26, XP055271803 (2011).
Iskhakova, Gulnara et al. "Diels-Alder reaction between naphthalene and N-phenylmaleimide under ambient and high pressure conditions", 1-10, XP93023886 (2005).
Kamm, Birgit et al. "International biorefinery systems", Pure & Applied Chemistry, 79(11):1983-1997, XP93023254 (2007).
Kim Sungjin et al. "Synthesis of 2,5-Diaminoquinones by One-Pot Copper-Catalyzed Aerobic Oxidation of Hydroquinones and Addition Reaction of Amines", Advanced Synthesis and Catalysis, 351(16):2573-2578, XP93023976 (2009).
Lange, Jean-Paul et al. "Lignocellulose conversion: an introduction to chemistry process and economics", Biofuels, Bioproducts & Biorefining, 1(1):39-48, XP93023325 (2007).
McCarthy, Joseph et al. "Lignin Chemistry, Technology, and Utilization: A Brief History" In: Chemistry, Process Design, and Safety

(56) References Cited

OTHER PUBLICATIONS for the Nitration Industry /ACS /Symposium Series, American Chemical Society/Oxford University Press, US, 1-99, XP93023322 (1999).
Ochoa-Gomez, Jose et al. "Industria Quimica Basada en Biomasa implicaciones tecnologicas", 1-106, XP93023315 (2007).
Qi Song et al. "Hydrogenolysis of lignosulfonate into phenols over heterogeneous nickel. catalysts", Chemical Communications, 48(56): 7019-7021, XP055157001 (2012).
Shao, Dan et al. "Electrochemical oxidation of lignin by two typical electrodes: Ti/Sb—SnO2 and Ti/PbO2", Chemical Engeneering Journal, 244:288-295, XP93023751 (2014).
Tarasov, Dmitry et al. "Production of Lignosulfonate in NSSC-Based Biorefinery", Biotechnology Progress, 31(6):1508-1514, XP093023239 (2015).
CAS Registry No. 783281-80-1; 2-Naphthalenesulfonic acid, 1,4-dihydro-3-methoxy-1,4-dioxo-, (2004).
CAS Registry No. 745756-46-1; 2,7-Naphthalenedisulfonic acid, 1,4-dihydro-3-(1-methylethoxy)-1,4-dioxo-, (2004).
Chemical Abstracts Accession No. 2012:1705525 (CAPlus), (2012).
Chemical Abstracts Accession No. 1964:468988 (CAPlus), (1964).
Chemical Abstracts Accession No. 1963:66335 (CAPlus); (1962).
Examination Report from corresponding Australian Application No. 2017246493 dated May 3, 2023.
Huskinson et al., "A metal-free organic-inorganic aqueous flow battery," Nature, 505(7482):195-198 (2014).

\* cited by examiner

METHODS FOR PROCESSING LIGNOCELLULOSIC MATERIAL

BACKGROUND

Since the invention of the oil refinery in the late 19th century, aromatic chemicals have been produced industrially from crude oil, mainly from catalytic reforming of the naphtha fraction, and are used for a range of high-volume industrial applications, including plastics from polystyrene (from styrene), polyethylene terephthalate (PET, from para-xylene), and phthalate resins (from ortho-xylene).

As supplies of crude oil dwindle around the world, alternative sustainable sources for these chemicals must be found, for which the aromatic lignin polymer found in lignocelluosic plant biomass is an abundant raw material. Although lignocelluosic biomass is annually renewable, it is still a limited resource. Nevertheless, the European Environment Agency estimates that Europe's biomass production capacity could grow up to 300 Mtons by 2030. Similarly, the US Department of Energy estimates that sustainable biomass production in the US could reach 1.2 Btons per year by 2060, and this without compromising edible crops.

Biomass is a mixture of organic molecules, containing hydrogen, oxygen, nitrogen, phosphorous and sulphur atoms, plus small quantities of alkali-, alkaline-earth metals and heavy metals. Lignocellulosic biomass can be considered a collection of fibrous cellulose backbones with a hemicellulose coating that are connected by lignin.

The aromatic heteropolymer lignin is a major component of plant cell walls, and is produced industrially from paper/pulp manufacture and cellulosic bioethanol production. Access to lignin from lignocellulosic material is growing, as pretreatment methodologies in the cellulosic ethanol and paper and pulp production yield lignin as a separate by-product. As of 2004, the pulp and paper industry alone produced 50 million tons of extracted lignin, yet the existing markets for lignin production remain limited and focus on low value products such as dispersing or binding agents. As a result, only approximately 2% of lignin s are used commercially with the remainder burned as a low value fuel. It is estimated that about 60% more lignin generated than is needed to meet internal energy use by its combustion. Nevertheless, lignin conversion has a significant potential as a source for the sustainable production of fuels and bulk chemicals. With its unique structure and chemical properties, a wide variety of bulk and fine chemicals, in particular aromatic compounds, as well as fuels or carbon materials are potentially obtainable from lignin.

Lignin is the only large-volume renewable feedstock that is composed of aromatics, and new processes are needed to fully utilize its potential as a source of value-added chemicals. Hence, the main goal of tomorrow's biorefineries will be the development of integrated approaches combining the processing of cellulose with the valorization of lignin.

SUMMARY

It is the object of the present invention to comply with the needs in the art and provide novel methods of integrated processing of both cellulose and lignin-derived process streams particularly derived from paper and pulp manufacturing.

DETAILED DESCRIPTION

Figure 1:
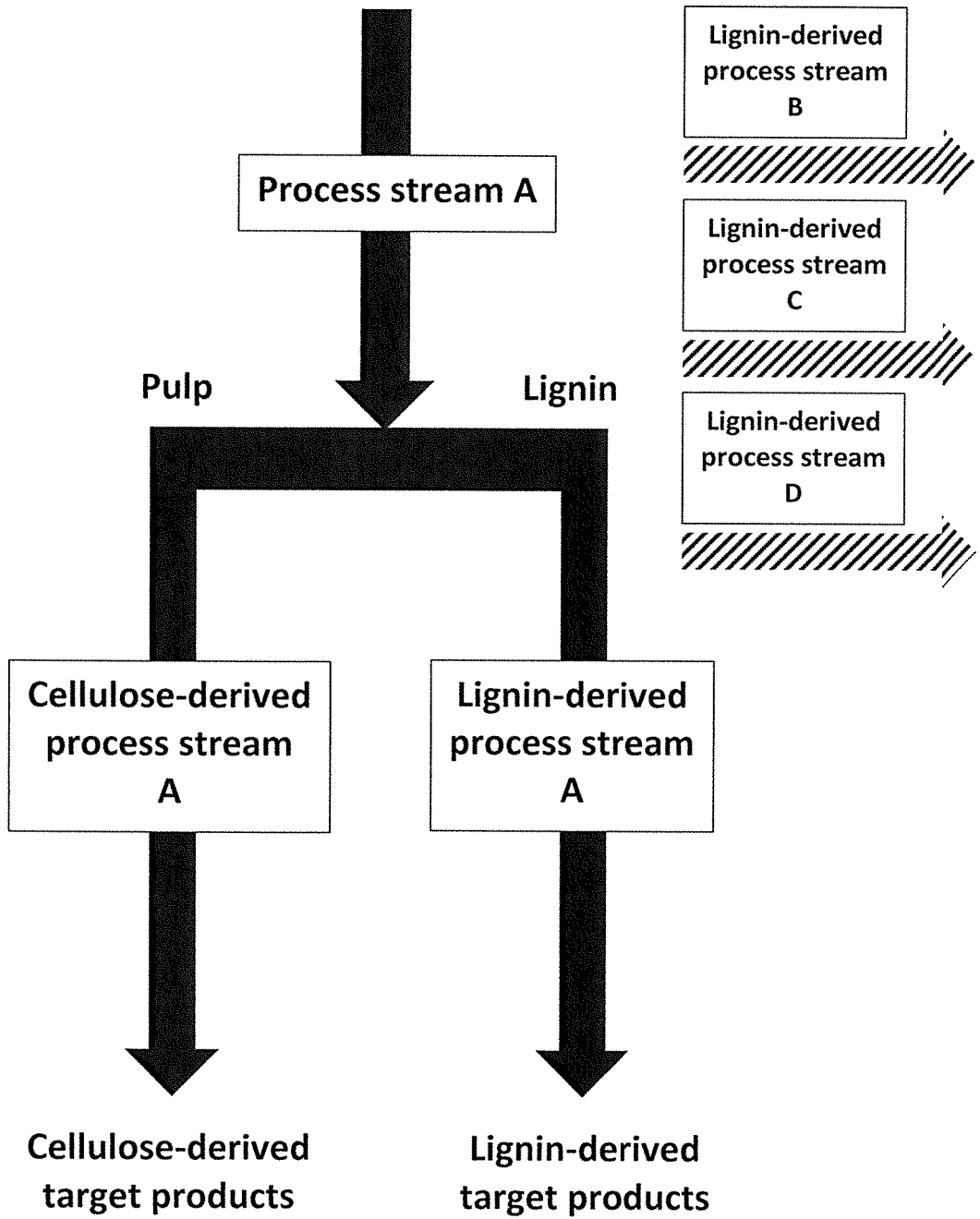
FIG. 1 illustrates the general principle underlying the inventive method. A main process stream A is separated into a cellulose-derived process stream A and a lignin-derived process stream A. Typically, separation is accomplished after pulping the lignocellulosic material. Dashed arrows are used to indicate that further lignin-derived process streams (B, C, D . . .) may be separated from the main process stream A to provide further valuable lignin-derived products via alternative routes of processing the lignocellulosic material. These additional process streams (B, C, D . . .) may in principle be separated from the main process stream A after any of the method steps described herein, typically prior to or after step 1) (provision and preparation of lignocellulosic material), after step 2) (pulping), after step 4) (isolation and purification of modified lignin-derived components) or after step 5) (chemical decomposition).
Figure 2:
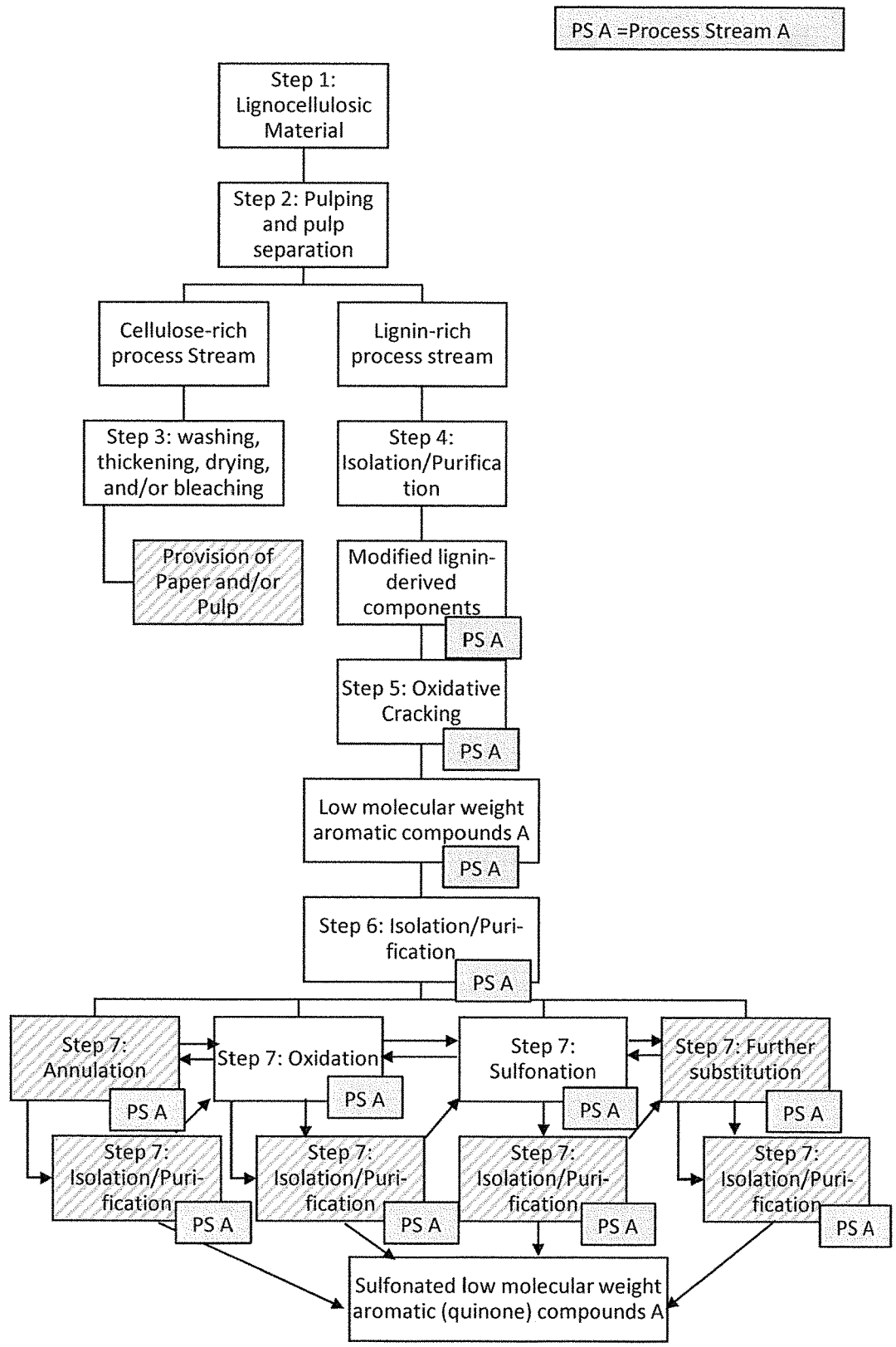
FIG. 2 illustrates the inventive method in some further detail. Shaded areas and dashed lines are used to indicate optional method steps.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the features of the present invention will be described. These features are described for specific embodiments. It should, however, be understood that they may be combined in any manner and in any number to generate additional embodiments. The variously described examples and preferred embodiments should not be construed to limit the present invention to only explicitly described embodiments. This present description should be understood to support and encompass embodiments, which combine the explicitly described embodiments with any number of the disclosed and/or preferred features. Furthermore, any permutations and combinations of all described features in this application shall be considered supported by the description of the present application, unless it is understood otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "alkyl" refers to the radical of saturated hydrocarbon groups, including linear (i.e. straight-chain) alkyl groups, branched-chain alkyl groups, cyclo-alkyl (alicyclic) groups, alkyl-substituted cyclo-alkyl groups, and cyclo-alkyl-substituted alkyl groups, or a group derived therefrom. Preferably, an alkyl group contains less than 30 carbon atoms, more preferably from 1 to 10 carbon atoms ("$C_{1-10}$ alkyl"), from 1 to 9 carbon atoms ("$C_{1-9}$ alkyl"), from 1 to 8 carbon atoms ("$C_{1-8}$ alkyl"), from 1 to 7 carbon atoms ("$C_{1-7}$ alkyl"), or from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group may contain 1 to 4 carbon atoms ("$C_{1-4}$ alkyl"), from 1 to 3 carbon atoms ("$C_{1-3}$ alkyl"), or from 1 to 2 carbon atoms ("$C_{1-2}$ alkyl").

Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like.

Unless otherwise specified, each instance of an alkyl group is independently unsubstituted (an "unsubstituted alkyl") or substituted (a "substituted alkyl") with one or more substituents (e.g., halogen, such as F).

In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. Compounds described herein contemplates any and all such combinations in order to arrive at a stable compound. Heteroatoms such as nitrogen may have hydrogen substituents and/or any suitable substituent as described herein which satisfy the valencies of the heteroatoms and results in the formation of a stable moiety. Compounds described herein are not intended to be limited in any manner by the exemplary substituents described herein.

In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted iso-propyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$alkyl, e.g., —$CF_3$, Bn).

Exemplary substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Substituents may themselves be substituted. For instance, the substituents of a "substituted alkyl" may include both substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls may be further substituted with alkyls, alkenyls, alkoxys, alkylthios, aminoalkyls, carbonyl-substituted alkyls, —$CF_3$, —CN, and the like.

The term "haloalkyl" refers a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group as defined herein, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent hydrocarbon chain. Unless otherwise specified, each instance of a heteroalkyl group is independently unsubstituted (an "unsubstituted heteroalkyl") or substituted (a "substituted heteroalkyl") with one or more substituents as defined herein.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system, or a group derived therefrom. Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents as defined herein.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"), or a group derived therefrom. In heterocyclyl groups that contain one or more nitrogen atoms, the point of attachment may be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and may be saturated or may contain one or more carbon-carbon double or triple bonds. Heterocyclyl polycyclic ring systems may include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents as defined herein.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"), or a group derived therefrom. In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as defined herein.

The term "aryl" as used herein thus includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"), or a group derived therefrom. In heteroaryl groups that contain one or more nitrogen atoms, the point of attachment may be a carbon or nitrogen atom, as valency permits. Heteroaryl polycyclic ring systems may include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

A group is optionally substituted unless expressly provided otherwise. The term "optionally substituted" refers to a group which may be substituted or unsubstituted as defined herein.

The term "aliphatic group" refers to a straight-chain, branched-chain, or cyclic non-aromatic saturated or unsaturated hydrocarbon group and includes as alkyl groups, alkenyl groups, and alkynyl groups.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to group of formula —OR, wherein R is an alkyl group, as defined herein. Exemplary alkoxyl groups include methoxy, ethoxy, propyloxy, tert-butoxy and the like.

The term "aralkyl", as used herein, refers to an alkyl group substituted with an aryl group (e.g., an aromatic or heteroaromatic group).

The term "carbonyl" refers to a group which contains a carbon atom connected with a double bond to an oxygen or a sulfur atom. Examples of moieties which contain a carbonyl include aldehydes, ketones, carboxylic acids, amides, esters, anhydrides, etc.

The term "ester" refers to groups or molecules which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "carbonyl" includes groups such as "alkylcarbonyl" groups where an alkyl group is covalently bound to a carbonyl group, "alkenylcarbonyl" groups where an alkenyl group is covalently bound to a carbonyl group, "alkynylcarbonyl" groups where an alkynyl group is covalently bound to a carbonyl group, "arylcarbonyl" groups where an aryl group is covalently attached to the carbonyl group. Furthermore, the term also refers to groups where one or more heteroatoms are covalently bonded to the carbonyl moiety. For example, the term includes moieties such as, for example, aminocarbonyl moieties, (where a nitrogen atom is bound to the carbon of the carbonyl group, e.g., an amide), aminocarbonyloxy moieties, where an oxygen and a nitrogen atom are both bond to the carbon of the carbonyl group (e.g., also referred to as a "carbamate"). Furthermore, aminocarbonylamino groups are also included as well as other combinations of carbonyl groups bound to heteroatoms (e.g., nitrogen, oxygen, sulfur, etc. as well as carbon atoms), such as thiocarbonyl, thiocarboxylic acid and thiolformate. Furthermore, the heteroatom can be further substituted with one or more alkyl, alkenyl, alkynyl, aryl, aralkyl, acyl, etc. moieties.

The term "ether" refers to groups or molecules which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" refers to groups or molecules which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties where an alkyl, alkenyl, or alkynyl group is bonded to a sulfur atom which is covalently bonded to an alkynyl group.

The term "amine" or "amino" includes compounds where a nitrogen atom is covalently bonded to at least one carbon atom or heteroatom. The term "alkyl amino" includes groups and compounds where the nitrogen is bound to at least one additional alkyl group. The term "dialkyl amino" includes groups where the nitrogen atom is bound to at least two additional alkyl groups. The term "arylamino" and "diarylamino" include groups where the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amine" or "amino" in particular refers to a —$NH_2$ group, preferably including any of its protonation states, such as —$NH_3^+$.

The term "amide" or "aminocarboxy" includes compounds or moieties which contain a nitrogen atom which is bound to the carbon atom of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties where alkyl, alkenyl, alkynyl and aryl moieties, respectively, are bound to a nitrogen atom which is in turn bound to the carbon of a carbonyl group.

The term "nitro" refers to a —$NO_2$ group.

The term "halo" or "halogen" refers to fluorine (fluoro, —F), chlorine (chloro, —Cl), bromine (bromo, —Br), or iodine (iodo, —I) groups.

The term "thiol" or "sulfhydryl" refers to a —SH group.

The term "hydroxyl" refers to a —OH group, preferably including all of its protonation states, such as —$O^+$.

The term "sulfonyl" refers to a —$SO_3H$ group, preferably including all of its protonation states, such as —$SO_3^-$.

The term "phosphoryl" refers to a —$PO_3H_2$ group, preferably including all of its protonation states, such as —$PO_3H^-$ and —$PO_3^{2-}$.

The term "phosphonyl" refers to a —$PO_3R_2$ group, wherein each R is H or alkyl, provided at least one R is alkyl, as defined herein, preferably including all of its protonation states, such as —$PO_3R^-$.

The term "oxo" refers to a =O group.

The term "carboxyl" refers to a —COOH group, preferably including all of its protonation states, such as —$COO^-$.

The term "oxy" refers to a —O group.

The term "quinone" refers to a class of cyclic organic compounds that include fully conjugated —C(=O)— groups and carbon-carbon double bonds. In one example, the term "quinone" refers to organic compounds that are formally derived from aromatic compounds by replacement of an even number of —CH=groups with —C(=O)— groups with the double bonds rearranged as necessary to provide a fully conjugated cyclic dione, tetra-one, or hexaone structure. The term inter alia covers substituted and unsubstituted quinones derived from mono-, di- and trihydroaromatic systems comprising 1 to 3 fused carbon cyclic rings in both their oxidized ("quinone") and reduced ("hydroquinone") forms.

The term "conjugated" when referring to two functional groups (having a double bond) means that the two groups are part of a connected system of p-orbital delocalized electrons with alternating single and multiple bonds. The two groups also include a degree of unsaturation. For example, conjugated groups may include multiple double bonds or aromatic groups (e.g., phenyl) between the groups. Moreover, if the two groups adjacent, the groups are also conjugated.

The term "standard electrode potential" means the electrical potential (i.e., the voltage developed) of a reversible electrode at standard state in which solutes are at an effective concentration of 1 mol/liter, the activity for each pure solid, pure liquid, or for water (solvent) is 1, the pressure of each gaseous reagent is 1 atm., and the temperature is 25° C. Standard electrode potentials are reduction potentials.

The term "zeolite" refers to typically microporous, aluminosilicate minerals, which are useful as adsorbents and catalysts.

The term "Polyoxometalate(s)" or "POM(s)" refers to polyatomic ions, usually anions that may be composed of three or more transition metal oxyanions, which are linked together by shared oxygen atoms to form a closed 3-dimensional framework.

The present invention provides novel methods for processing lignocellulosic material. Advantageously, the methods envisages the processing of both cellulose and lignin obtained from the lignocellulosic starting material and therefore offers a comprehensive approach for the utilization of lignocellulosic material.

"Lignin" is generally understood herein as wood-derived heterogeneous phenolic macromolecule or, rather, a group of phenolic macromolecules of plant origin, which is or are composed of different monomeric building blocks. Hence, it is understood to be a natural copolymer. More specifically, lignin may be generally defined as an amorphous three-dimensional polymer, which is mainly and naturally composed of phenolic building blocks. Lignin in its "native" state, i.e. as part of the natural lignocellulosic material, is the starting material of the inventive method for any "modified lignin" and, subsequently, any "lignin-derived" compositions or compounds as described herein as product of the inventive methods.

Lignin typically comprises p-coumaryl, coniferyl and sinapyl alcohol as the phenolic building blocks, which are linked (randomly) with ether (C—O—C) bonds, such as "beta-O-4", "4-O-5" and, to a less frequent extent, "1-O-4". The most frequently seen covalent linkage in natural softwood and hardwood lignin is typically the "beta-O-4" bond, which accounts, e.g., for approximately 45-50% of all bonds in spruce and up to 60% in birch. Additionally, carbon-carbon (C—C) linkages may occur in natural lignin, such as "5-5", "beta-5", "beta-beta" and "beta-1", amongst which the "5-5" linkage is the most frequently seen C—C linkage, in particular in softwood, such as spruce. Typical linkages as "beta-O-4", "4-O-5" and "5-5" are depicted in the following:

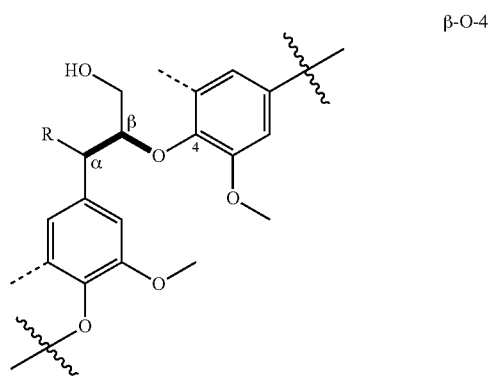

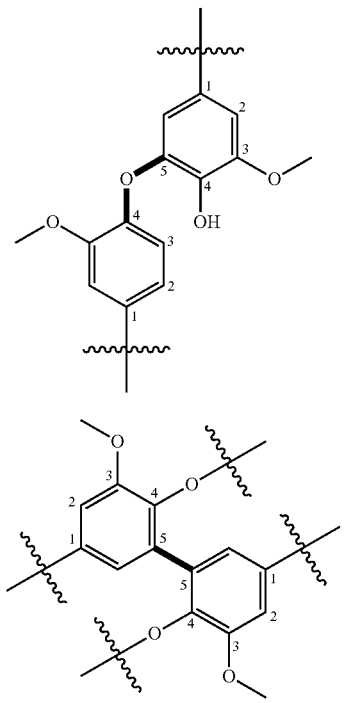

A "building block" as a base unit (derived from lignin) as used herein may preferably be understood as an organic moiety, which comprises at least one bond to covalently link said building block to another building block of the same or different chemical structure to form a plurality of covalently associated building blocks. Preferably, a building block according to the present invention is a "phenolic building block", i.e. any moiety comprising a six-membered aromatic ring, covalently functionalized by at least one hydroxyl group (—OH). Hence, the lignin "building block" is typically characterized by a monocyclic, typically an aromatic moiety, with the monocycle typically being substituted at least one position. Typically, each lignin building block exhibits a carbocyclic monocycle with one or two substituents acting as linkers to another building block and one or two substituents, which do not exhibit any linking function. A building block corresponds to a "monomer". A "dimer" as used herein typically comprises two such building blocks covalently linked. Thus, the dimer is typically characterized by two isolated monocyclic moieties covalently linked by a linker group or by a bond (biphenylic ring system). Biphenylic ring systems (as characteristic moiety of dimers) occur with lower frequency in plant lignin, in some plants (e.g. in spruce) with higher frequency. More generally, any such dimeric compounds belong to the class of bicycles.

A larger plurality of any such covalently connected or linked building blocks forms typically the larger 3-dimensional lignin structure. In the context of the present invention, a "polymer" refers to a natural lignin molecule as it occurs in plants, e.g. as part of lignocellulosic material. The lignin polymer is typically a copolymer of distinct building blocks. Natural lignin's "building block" corresponds to a "monomer". Accordingly, a building block typically is a (repeating) structural part of the natural polymer lignin. The (phenolic) building block has typically 9 carbon atoms ($C_9$) or, less frequently seen, 8 carbon atoms ($C_8$). Typically, the building blocks have a molecular weight of about 130 to 300 Da, preferably of 150 to 250 Da, more preferably of 160 to 190 Da. Preferably, their basic monomeric $C_9$ or $C_8$ structure is not altered in the course of the natural lignin modifying process by e.g. pulping. Such building blocks may serve as the basic unit in their chemistry, providing aromatic organic target compounds according to the present invention.

As used herein, the term "lignin-derived" has the broadest meaning with regard to any lignin, which underwent one or more process steps, from process step (1) onwards, according to the present invention. Therein, a "derived" material has to be understood as a chemical derivative. A "lignin-derived" material may be of any molecular weight smaller than the natural lignin polymer, including a small molecule, i.e. a low molecular weight compound as used herein. In this regard, both "modified lignin-derived components" and "lignin-derived compounds" according to the present invention are lignin-derived material. Accordingly, a "lignin-derived" modified lignin-derived component or a (target or precursor) compound as defined herein, is a (macro-)molecule, which corresponds to or is derived from a (monomeric) building block of natural lignin or is a homo- or heterodimers of such (monomeric) building blocks. Such compounds are derived from natural lignin via its modification in step (1.2) onwards, which provides the fraction of modified lignin-derived components as intermediates of the inventive method. Subsequently, a chemical decomposition step (3) provides lignin-derived low molecular weight precursor compounds that are subjected to a sulfonation step (5) to yield lignin-derived low molecular weight aromatic target compounds according to the invention. "Lignin-derived" compositions are thus comprising or (essentially) consisting of lignin-derived compounds.

In a further aspect, the present invention provides a method for producing sulfonated lmw (aromatic) compounds and compositions derived from lignin, fossil resources (such as crude oil or coal) or pure substances. An inventive method for preparing the desired target compounds and compositions from lignin is described in greater detail in the following.

General Method

The present invention generally relates to a method of processing lignocellulosic material to prepare valuable end products. Therefore, a main process stream (A) is derived from lignocellulosic material and processed according to the inventive method. The main process stream A is separated to provide a cellulose-derived process stream A and a lignin-derived process stream A. The cellulose-derived process stream A is subjected to at least one further processing steps in order to obtain valuable cellulose-derived compounds or products, such as paper or paperboard products. The lignin-derived process stream A is subjected to further processing steps in order to provide valuable low molecular weight lignin-derived compounds. The compounds are preferably aromatic in nature and are more preferably quinone compounds. Preferably, the lignin-derived process stream A may be used to obtain sulfonated low molecular weight aromatic lignin-derived quinone compounds, which may advantageously find use as redox flow battery electrolytes.

A "stream" or "process stream" refers to a conglomeration of material commonly resulting from and/or being subjected to a particular process step. The term as such generally does not imply any limitation as to the nature (e.g. phase) or composition of material. That is, a "process stream" according to the invention includes process streams of liquid and solid matter. A "lignin-derived process stream" preferably corresponds to or is derived from the lignin-derived fraction received after pulping of the lignocellulosic starting material. A "cellulose-derived process stream" preferably corresponds to or is derived from the cellulose-derived fraction received after pulping of the lignocellulosic starting material. After pulping, the main process stream A is preferably separated by appropriate means to yield the lignin-derived process stream A and the cellulose-derived process stream A. Process streams do not need to be pure and may comprise a mixture of different compounds. Accordingly, a "cellulose-derived process stream" refers to a process stream comprising the principal portion of cellulose (also referred to as "pulp") derived from the lignocellulosic material after pulping, whereas a "lignin-derived process stream" refers to a process stream comprising the principal portion of lignin derived from the lignocellulosic material after pulping. Cellulose-derived process streams thus typically comprises a higher proportion of cellulose than lignin-derived process streams, whereas lignin-derived process streams typically comprise a higher proportion of lignin than cellulose-derived process streams. Both types of process streams may however comprise residual amounts of cellulose/hemicellulose (in the lignin-derived process stream) or lignin (in the cellulose-derived process stream) as well as by-products, impurities, solvents, catalysts or reactants that may for instance have been introduced by the pulping process.

The cellulose-derived process stream A or "pulp" essentially comprises a mixture of (preferably pure/enriched) cellulosic fibrous material, and does not contain lignin or lignin-derived components or contains only minor residual amounts of lignin components (e.g. as impurities of the cellulosic fibrous material). It is further processed in step 3) to preferably yield valuable chemical compounds or paper or paperboard products as described herein.

The lignin-derived process stream A typically comprises modified lignin-derived components, which are typically lower molecular size fragments of lignin (natural lignin), and may typically be polymeric. Such modified lignin-derived components are usually more soluble or dispersible than natural lignin. In the paper and pulp industry, lignin-derived process streams are typically regarded waste material and a by-product of paper production from cellulose. It is thus typically either discarded or burned as fuel. However, the present invention provides a novel integrated process that allows the preparation of valuable compounds from the lignin-derived process stream in parallel to the cellulose-based products obtained from the cellulose-derived process stream.

To that end, in step 4), the lignin-derived process stream A is subjected to an isolation and/or purification step, yielding modified lignin-derived components. In step 5), said modified lignin-derived components are subjected to a chemical decomposition step to depolymerize the lignin-derived fragments and thereby obtain low molecular weight lignin-derived compounds. In step 6), said compounds are subsequently isolated and purified. Preferably, the compounds are further subjected to chemical transformation step 7), wherein the compounds may be annulated, substituted, oxidized, reduced isolated, purified or treated otherwise to obtain desired lignin-derived end products. Preferably, low molecular weight aromatic lignin-derived compounds derived from process stream A and obtained from step 6) may be (a) annulated to obtain polycyclic aromatic compounds A, (b) oxidized to introduce hydroxyl- or oxo-functional groups, preferably yielding quinone compounds A, (c) sulfonated to introduce one or more sulfonyl functional groups and (d) optionally further derivatized, to introduce further functional groups of interest. These sub-steps (a)-(d) may be conducted in any suitable order (indicated by forward and backward arrows) and may each be preceded or anteceded by a suitable isolation/purification step to preferably obtain, optionally substituted, quinone compounds.

Preferably, lignin-derived process stream A is used to obtain, optionally substituted, quinone compounds characterized by General Formula (1), (2) or (3):

General Formula (1)

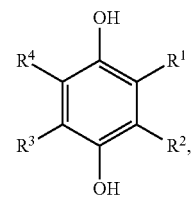
(a)

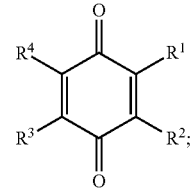
(b)

General Formula (2)

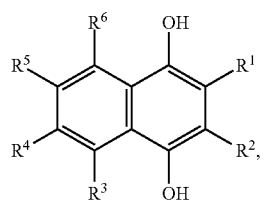
(a)

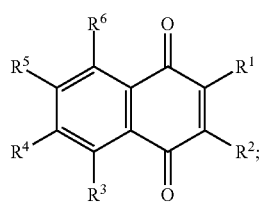
(b)

General Formula (3)

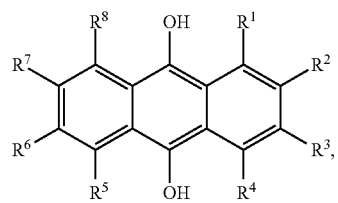
(a)

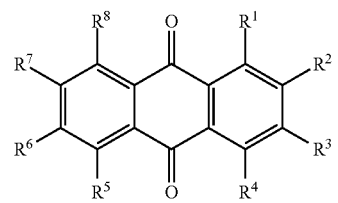
(b)

wherein each of $R^1$-$R^4$ in formula (1); $R^1$-$R^6$ in formula (2); and/or $R^1$-$R^8$ in formula (3)

is independently selected from hydrogen; hydroxyl; carboxy; optionally substituted $C_{1-6}$ alkyl optionally comprising at least one heteroatom selected from N, O and S, including —$C_nH_{2n}OH$, —$C_nH_{2n}NH_2$ and —$C_nH_{2n}SO_3H$, wherein n is an integer selected from 1, 2, 3, 4, 5, or 6; carboxylic acids; esters; halogen; optionally substituted $C_{1-6}$ alkoxy, including methoxy and ethoxy; optionally substituted amine, including primary, secondary, tertiary and quaternary amines, in particular —$NH_2/NH_3^+$, —$NHR/NH_2R^+$, —$NR_2/NHR_2^+$ and —$NR_3^+$, where R is H or optionally substituted $C_{1-6}$alkyl optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$; amide; nitro; carbonyl; phosphoryl; phosphonyl; cyanide; and sulfonyl (—$SO_3H$), wherein preferably at least one of $R^1$-$R^4$ in formula (1); $R^1$-$R^6$ in formula (2); and/or $R^1$-$R^8$ in formula (3) is selected from —$SO_3H$; —$C_nH_{2n}SO_3H$ optionally comprising at least one heteroatom selected from N, O and S, wherein n is an integer selected from 1, 2, 3, 4, 5, or 6, optionally substituted amine, in particular —$NH_2/NH_3^+$, —$NHR/NH_2R^+$, —$NR_2/NHR_2^+$ and —$NR_3^+$, where R is H or optionally substituted $C_{1-6}$alkyl optionally comprising at least one heteroatom selected from N, O and S, including —$C_nH_{2n}OH$, —$CH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$; and optionally substituted $C_{1-6}$ alkoxy, preferably methoxy.

According to a different annotation, and without changing the scope of the invention, the quinone compounds according to General Formula (1), (2) and (3) may be defined as follows:

General Formula (1)

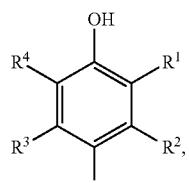
(a)

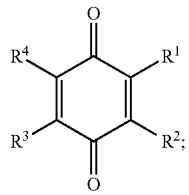
(b)

General Formula (2)

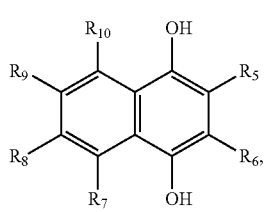
(a)

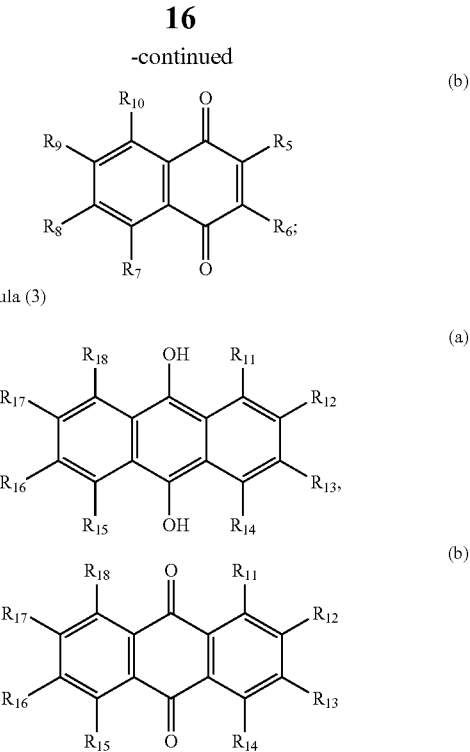

General Formula (3)

wherein $R^1$-$R^{18}$ are each independently selected from hydrogen; hydroxyl; carboxy; optionally substituted $C_{1-6}$ alkyl optionally comprising at least one heteroatom selected from N, O and S, including —$CH_{2n}OH$, —$C_nH_{2n}NH_2$ and —$C_nH_{2n}SO_3H$, wherein n is an integer selected from 1, 2, 3, 4, 5, or 6; carboxylic acids; esters; halogen; optionally substituted $C_{1-6}$ alkoxy, including methoxy and ethoxy; optionally substituted amine, including primary, secondary, tertiary and quaternary amines, in particular —$NH_2/NH_3^+$, —$NHR/NH_2R^+$, —$NR_2/NHR_2^+$ and —$NR_3^+$, where R is H or optionally substituted $C_{1-6}$ alkyl optionally comprising at least one heteroatom selected from N, O and S, including —$CH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$; amide; nitro; carbonyl; phosphoryl; phosphonyl; cyanide; and sulfonyl (—$SO_3H$), wherein preferably at least one of $R^1$-$R^{18}$ is selected from —$SO_3H$; —$C_nH_{2n}SO_3H$ optionally comprising at least one heteroatom selected from N, O and S, wherein n is an integer selected from 1, 2, 3, 4, 5, or 6, optionally substituted amine, in particular —$NH_2/NH_3^+$, —$NHR/NH_2R^+$, —$NR_2/NHR_2^+$ and —$NR_3^+$, where R is H or optionally substituted $C_{1-6}$ alkyl optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$; and optionally substituted $C_{1-6}$ alkoxy, preferably methoxy.

Therein, "$R^1$-$R^4$ of General Formula (1)" correspond to $R^1$-$R^4$. "$R^1$-$R^6$ of General Formula (2)" correspond to $R^5$-$R^{10}$. "$R^1$-$R^8$ of General Formula (3)" correspond to $R^{11}$-$R^{18}$.

Further process streams (B, C, D . . . ) may be separated from the main process stream A, preferably the lignin-derived process stream A, to provide further valuable end products (not shown). These further process streams may be processed either simultaneously, or in a time-staggered manner with regard to the lignin-derived process stream A. The present invention is thus inter alia based on the idea to provide a method that makes use of both the cellulose- and the lignin-derived process streams originating from a pulping process, wherein the lignin-derived process stream is inter alia used to provide low molecular weight aromatic lignin-derived compounds, preferably low molecular weight aromatic lignin-derived quinone compounds, more preferably sulfonated low molecular weight aromatic lignin-derived compounds.

Figure 3:
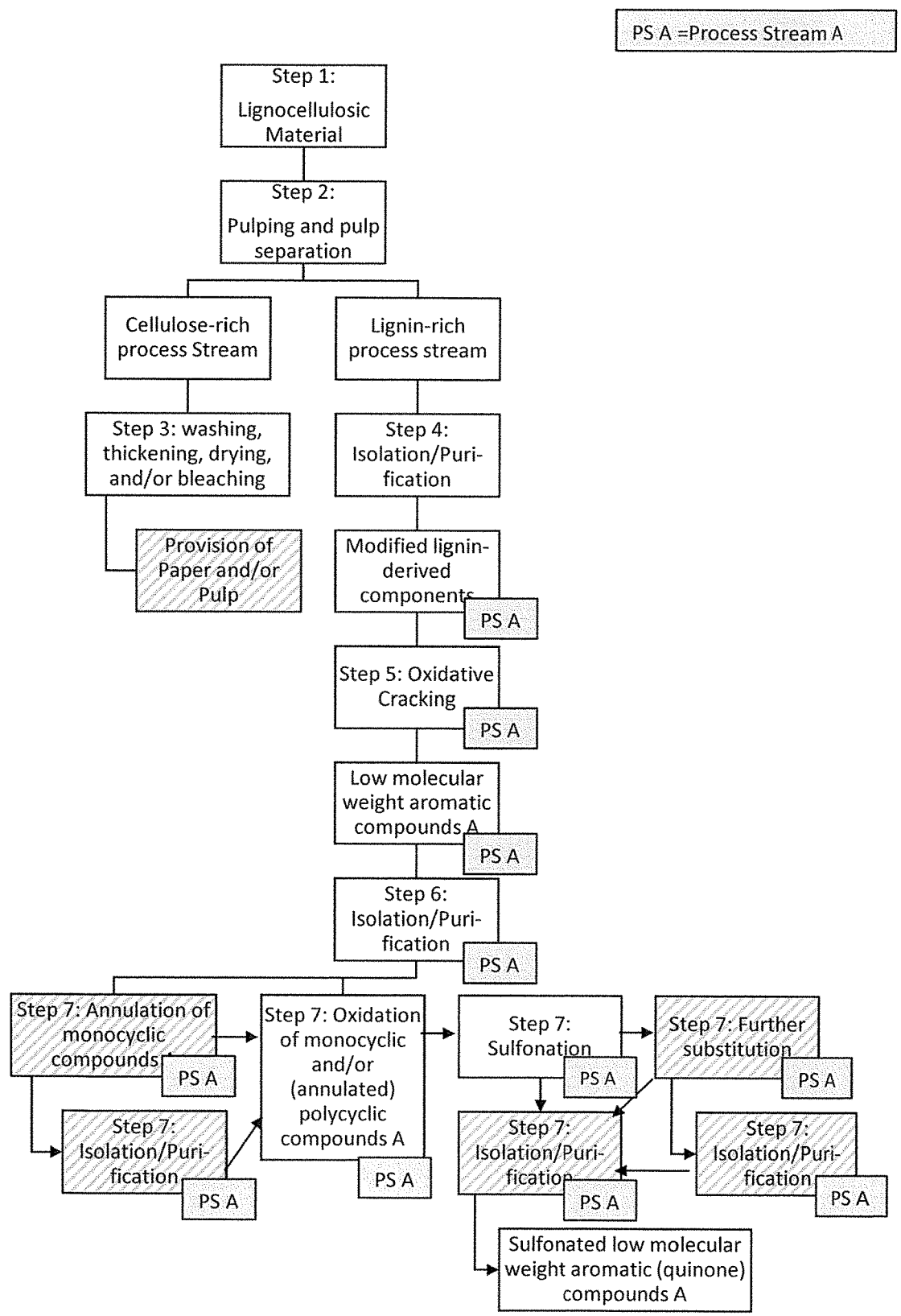
FIG. 3 shows a preferred sequence of method steps according to the inventive method. In step 1), lignocellulosic material is provided and optionally prepared as described herein. In step 2), the (prepared) lignocellulosic material is subjected to a pulping process and pulp separation step. Step 2) is preferably used to separate the cellulose fraction from the lignin fraction in the main process stream A. Thereby, the pulping process preferably yields a cellulose-derived process stream A (left) and a lignin-derived process stream A (right).

FIG. 3 shows the preferred downstream processing of lignin-derived process stream A, wherein low molecular weight aromatic lignin-derived compounds are (optionally) subjected to annulation, oxidation and substitution followed by isolation/purification in step 7) to obtain substituted (preferably sulfonated) low molecular weight aromatic lignin-derived quinone compounds.

Accordingly, the inventive method comprises the following steps:

1) providing and optionally preparing a process stream A comprising lignocellulosic material;
2) subjecting said process stream A comprising lignocellulosic material to a pulping step and a separation step, thereby obtaining two separate process streams: at least one cellulose-derived process stream A, and at least one lignin-derived process stream A;
3) further processing said at least one cellulose-derived process stream A, optionally by subjecting said cellulose-derived process stream to one or more of the following sub-steps: washing, delignification, bleaching, chemical transformation, manufacturing of paper or paperboard, or any combination thereof.
4) subjecting said at least one lignin-derived process stream A to at least one isolation and/or purification step, thereby obtaining at least one process stream A comprising modified lignin-derived components;
5) subjecting said at least one lignin-derived process stream A comprising modified lignin-derived components to a chemical decomposition step, wherein the chemical decomposition step comprises oxidative cracking, reductive cracking or electro-oxidation of said modified lignin-derived components, thereby obtaining at least one lignin-derived process stream A comprising low molecular weight aromatic lignin-derived compounds;
6) subjecting said at least one lignin-derived process stream A comprising modified lignin-derived compounds to an isolation and/or purification step, thereby obtaining at least one lignin-derived process stream A of low molecular weight aromatic lignin-derived compounds.

Preferably, the inventive method may comprise an additional step of:

7) subjecting said at least one lignin-derived process stream A comprising low molecular weight aromatic lignin-derived compounds to a chemical transformation reaction, said chemical transformation reaction including at least one annulation, oxidation or substitution reaction, or any combination thereof, thereby obtaining a process stream A of optionally substituted low molecular weight aromatic lignin-derived quinone compounds.

The low molecular weight aromatic lignin-derived compounds obtained from lignin-derived process stream A are preferably characterized by any one of General Formulas (1), (2) or (3), as defined above.

Each of the method steps of the inventive method will be described in greater detail below.

Further methods according to the invention may not include step 3) of cellulose processing, but may rather include steps 1), 2), 4), 5), 6) and optionally 7) and 8) as described herein for lignin-derived process stream A, and preferably additionally include at least one step of separating and processing at least one further lignin-derived process streams (B, C, D . . . ) as described herein.

Step (1): Provision of Lignocellulosic Material

In step (1) of the inventive method, lignocellulosic material is provided and optionally prepared.

Lignocellulosic Material

"Lignocellulosic material", understood to be the starting material for the method of the present invention, may be provided as any form of plant biomass, which naturally comprises cellulose, lignin and hemicellulose. Therein, cellulose (a polysaccharide consisting of a linear chain of several hundred to many thousands of beta(1→4) linked D-glucose units) typically forms a scaffold of fibers together with hemicellulose. Lignin (as defined above) is typically embedded within this scaffold, typically without being covalently linked to cellulose and/or hemicellulose. "Hemicellulose" is any of several heteropolymeric polysaccharides, which include xylan, glucuronoxylan, arabinoxylan, glucomannan, and xyloglucan. It is typically present along with cellulose in almost all plant cell walls. In contrast to cellulose, hemicellulose usually has a random, amorphous structure with little strength.

The lignocellulosic material may be derived from any appropriate plant origin, e.g. wood, fiber crops or waste paper origin. Accordingly, suitable lignocellulosic material to be treated according to the inventive method includes, without limitation, wood, fiber crops, bagasse and waste paper. Waste paper, e.g. newspaper paper, processed according to the inventive method is preferably of lower paper quality, and comprises higher amounts of residual lignin, in contrast to higher quality paper, which is typically lignin-free. Field crop fiber or agricultural residues (instead of wood fiber) may be preferred as being of more sustainable nature. "Bagasse" is the fibrous residue that remains once plant material (such as sugar cane) has been crushed and juice or sap have been extracted. However, wood is the preferred renewable source, with about 90 percent of pulp originating from wood plantations or reforested areas. Non-wood fiber sources may be employed by the inventive method as well (as far as it is for global pulp production), for a variety of reasons, including seasonal availability, problems with chemical recovery, brightness of the pulp etc. Non-wood pulp processing, however, usually requires more water and energy than wood pulp pressing.

Lignocellulosic material of known and invariant character may be preferred, such that the inventive method's downstream products remain essentially unaltered. It may be preferred to employ lignocellulosic material with a lignin content of at least 15%, more preferred of at least 20%, most preferred of 20 to 35%.

Accordingly, the lignocellulosic material provided in step 1) of the inventive method is preferably selected or derived from soft- or hardwoods. More preferably, said lignocellulosic material may be selected or derived from wood of low silica and resin content, even more preferably from northern woods, most preferably from beech, pine, birch, eucalyptus or spruce.

Preparation of Lignocellulosic Material

Step 1) of the inventive method may further preferably include the preparation of the provided lignocellulosic material for further downstream processing. Preparing the lignocellulosic material may preferably comprise debarking, depithing, chopping, grinding, crushing, milling, cleaning, refining and/or screening said lignocellulosic material. Any suitable combination of these preparation methods may be employed. Preferably, the lignocellulosic material may be chopped and be provided, e.g., in the form of wood chips.

"Wood chips" are understood as a medium-sized solid material made by cutting, or chipping, larger pieces of wood. Characteristic values (such as water content, ash content, particle size distribution, bulk density, nitrogen content, chlorine content) are preferably chosen such that they fulfil generally accepted provisions, such as the European Standard EN 14961. Wood chips as typically used for chemical pulping processes are preferably used for the inventive method as well as they are usually relatively uniform in size and substantially free of bark. The optimum size may vary with the wood species. Preferred sizes of the main fraction are about 3 to 45 mm with a fine fraction, defined as particles below 1 mm, of preferably less than 5%. Common wood chips used in pulp production, which are preferred in the method of the present invention, are on average 12-25 mm (0.47-0.98 in) long and 2-10 mm (0.079-0.394 in) thick. Damage of the wood fibers is preferably avoided, as fibers free of physical defects are advantageous for the pulp properties. For roundwood it is most common to use disk chippers. Therein, "roundwood" is understood as industrial roundwood, which is commonly defined, e.g., in the FAO Forest Products Yearbook to include all industrial wood (e.g. sawlogs and veneer logs, pulpwood and other industrial roundwood) and marketed forms, such as chips, particles or wood residues.

Advantageously, wood chips can be used both for preparing pulp and paper on the one hand, and valorized lignin-derived products on the other hand, in the inventive method.

Accordingly, "preparing" the lignocellulosic material in step 1) of the inventive method may preferably include debarking, chopping, grinding, crushing, milling, cleaning, refining and/or screening said lignocellulosic material.

Step (2): Pulping

Pulping Process

In step (2) of the inventive method, the lignocellulosic material is subjected to a pulping process. Generally, the terms "pulping" or "pulping process" as used herein refer to a process of essentially separating cellulose, hemicellulose and lignin components of lignocellulosic material, preferably by chemically and/or mechanically disjoining cellulose fibres from other constituents of the lignocellulosic starting material, such as any wood, fibre crops or waste paper. Any "pulping process" is typically aimed at the disintegration of wood into fibrous cellulosic material, lignin and hemicellulose products. That is achieved by breaking covalent bonds of the 3-dimensional polymeric lignin macromolecules, in particular carbon-oxygen (C—O) bonds which are generally less stable than carbon-carbon (C—C) bonds under the reaction conditions of the pulping process.

By deploying conventional pulping processes, the inventive method may employ existing plants for pulp production. In most paper mills, where pulping processes are commonly applied to obtain precursor materials for the production of paper and paper products, lignin-derived process streams are either discarded, or burned as fuel. In contrast, the inventive method advantageously envisages an integrated process of using both process streams—one rich in cellulose, one in lignin—to obtain valuable products.

The inventive method therefore provides for the unprecedented use of both the cellulose- and the lignin-derived process stream emerging from commonly known pulping processes for the production of valuable materials and compounds. Advantageously, the inventive method thereby enables the valorization of lignin as an abundantly available and renewable natural material in parallel to the production of paper and pulp. If desired, part of the lignin-derived process stream may be used as an energy source for the plant.

The pulping process employed may generally be any pulping process known in the art and preferably commonly used by the paper and pulp industry.

Typical pulping processes that may be used in step 2) of the inventive method include chemical pulping processes preferably selected from the Kraft process; sulphite process; organosolv process; or other chemical pulping processes known in the art.

Particularly preferred pulping processes in the context of the present invention include the Kraft process and the sulphite process, both of which are described in greater detail elsewhere herein. The choice of a particular pulping process of may depend on the type of lignocellulosic material on the one hand, and on the desired products to be obtained from the inventive method on the other hand.

Accordingly, the pulping process in step 2) of the inventive method is preferably selected from a chemical pulping process, including kraft (sulphate) pulping, sulphite pulping, and organosolv pulping. The Kraft process and the sulphite process being particularly preferred pulping processes in the context of the present invention.

(a) Kraft Process

The "Kraft process" is by far the most prevalent pulping process worldwide. It is typically a high pH pulping process in aqueous solution containing one or more of salt or non-salt agents selected from sulphide, sulfhydryl and polysulphide; and further typically a sulphate salt. The Kraft process is versatile in terms of the lignocellulosic starting material, which is treated in aqueous solution at elevated temperature and pressure. It is energy efficient and recycles most of the employed reactive agents, such as reactive agents required for the pulping process. Typically, the modified lignin-derived components (Kraft lignin) obtained from the Kraft process have a molecular weight of about 2.000 to 5.000 Da, preferably 2.000 to 3.000 Da. They may be components of the natural 3-D lignin polymers, and may potentially be chemically functionalized.

The Kraft process may preferably comprise following sub-steps, which are discussed in greater detail further below:

(i) optionally pre-steaming the (preferably chopped) lignocellulosic material, wherein the (preferably chopped) lignocellulosic material is advantageously wetted and preheated with steam;

(ii) adding (preferably chopped) lignocellulosic material to an aqueous alkaline solution comprising Kraft pulping agents, one or more of the agents preferably being selected from the group consisting of a sulphide salt, a sulfhydryl agent (in particular a sulfhydryl compound or salt), a polysulphide salt (and, typically, at least one sulphate salt is additionally comprised by the alkaline solution as well);

(iii) cooking the (preferably chopped) lignocellulosic material, which is provided (e.g. suspended and/or dispersed)) in said aqueous alkaline solution; and optionally (iv) sulfonating the lignocellulosic material in the presence, e.g. of sulfuric acid solution and/or sulphur trioxide.

Sub-Step (i): Pre-Steaming

In sub-step (i) of the Kraft process, lignocellulosic material—which is preferably provided in chopped form, e.g. in the form of wood chips—may be pre-treated with hot steam. In doing so, preferably chopped lignocellulosic material is wetted and heated. Thereby, cavities of fresh wood are typically filled with fluids and/or air, which is caused to expand by steam pre-treatment. About 25% of the air and/or other fluids naturally occupying the cavities is thereby expelled from these cavities.

Lignocellulosic material treated in such a way may thus preferably more readily adsorb treatment solutions as applied by subsequent sub-step (ii).

Sub-Step (ii): Impregnation

In sub-step (ii) of the Kraft process, the optionally pre-treated, i.e. pre-steamed and preheated, preferably chopped lignocellulosic material is treated, preferably at elevated temperatures, with an aqueous alkaline solution ("treatment solution").

The treatment solution typically comprises at least one chemically reactive agent and may be referred to as "white liquor". Chemically reactive agents in the treatment solution may function to adjust the pH and/or provide nucleophilic sulphide ($S^{2-}$) and/or bisulphide ($HS^-$) ions and/or moieties. Typically, said treatment solution comprises a mixture of chemically reactive agents generally used for Kraft pulping to provide nucleophilic sulphide and/or bisulphide ion or moiety for rupturing the embedment of lignin in the cellulose scaffold of natural lignin. The reactive sulphur containing agents are usually provided as (dissolved) salts, but they may also be provided as non-salt agents, e.g. as (dissolved) organic compounds, which comprise one or more sulphur or sulphur-based chemical functionalities. Generally, any suitable reactive agent known in the art for use in the impregnation and cooking step of the Kraft process may be employed according to the present invention. Other than the sulphur containing reagents, further agents added to the solution in lower amounts are typically one or more of sodium carbonate, sodium sulphate, sodium thiosulphate, sodium chloride, and calcium carbonate.

Preferably, either of the sulphide and/or sulphate salt comprised in the alkaline solution used in the Kraft process according to (a) is a salt with a cationic counter ion preferably selected from the group consisting of sodium, calcium, magnesium and ammonium. The sulfhydryl and/or polysulphide agent employed by the Kraft process according to (a) is preferably an organic, non-salt agent.

Sub-step (ii) of the Kraft process typically involves adding the preferably chopped lignocellulosic material to a treatment solution as described herein. Thereby, the lignocellulosic material is typically initially saturated with the aqueous alkaline solution, e.g. with the fresh ("white liquor") treatment solution or with its recycled equivalent ("black liquor"). The treatment solution preferably penetrates into the capillary structure of the chopped lignocellulosic material, and preferably starts to react with the lignocellulosic material. The step is preferably designated as the "impregnation step", and may be performed before the (impregnated) lignocellulosic material is subjected to sub-step (iii) of the Kraft process. Typically, the lignocellulosic material is not heated or exposed to elevated temperatures, or is only heated gently, in sub-step (ii) of the Kraft process.

Impregnation of the lignocellulosic material in sub-step (ii) may preferably support subsequent reactions during the "cooking" step and homogeneity, yielding higher amounts of soluble "Kraft lignin". Usually, about 40-60% of all alkaline pulping liquor may be consumed for the continuous type Kraft process in its initial impregnation step.

The treatment solution ("liquor") used for impregnation may be used in sub-step (iii) (cooking) as well (as a "cooking liquor").

The treatment solution may comprise additional reactive agents to improve the Kraft impregnation of e.g. the employed wood chips with the cooking liquor. Anthraquinones may be added to act as redox catalysts by oxidizing cellulose and reducing lignin, thereby preferably protecting cellulose from degradation and increasing water-solubility of lignin components. Emulsion breakers may be added in an optional soap separation step to expedite and improve the separation of soap, e.g. rosin soap (a common by-product of the Kraft process) from the cooking liquors by flocculation. The soap typically floats at the surface of the aqueous liquid and has to be skimmed off. The collected soap may be further processed to tall oil. Defoamers may be employed to remove eventually formed foam and foster the pulp production process. Drainage of washing equipment gives cleaner pulp. Dispersing agents, detackifiers and/or complexing agents preferably allow to keep the process vessels cleaner and to reduce the number of maintenance operations. Fixation agents may be used to allow finely dispersed material to be deposited on the fibers, thereby allowing such material to be readily eliminated.

Preferably, the pH of the aqueous alkaline solution in sub-step (ii) of the Kraft process according to (a) is >10. More preferably, the pH in sub-step (ii) of the Kraft process according to (a) is >12. The temperature of the aqueous alkaline solution in sub-step (ii) of the Kraft process according to (a) is typically less than 100° C., e.g. in the range from 70° C. to 90° C.

Sub-Step (iii): Cooking

In sub-step (iii) of the Kraft process, the preferably chopped and pre-treated ("impregnated") lignocellulosic material is "cooked" in the treatment solution.

During the "cooking" sub-step (iii), internal lignin ether bonds are preferably disrupted by nucleophilic attack of sulphide ($S^{2-}$) and/or bisulphide ($HS^-$) ions or moieties. The function of sulphide in the Kraft process may be two-fold and include (1) initiation and acceleration of the cleavage of ether bonds between neighbouring lignin building blocks and (2) reduction of undesirable condensation. The reaction conditions are typically chosen to provide satisfying yields, while still ensuring overall process efficiency.

Preferred reaction conditions during sub-step (iii) of the Kraft process may encompass one or more of the following: Duration: at least 2 hours, typically between 3-9 hours; Temperature: at least 150° C., preferably between 150° C. to 190° C., more preferably 170° C. to 180° C.; Pressure: at least 4 bar, preferably between 5 and 10 bar in a pressurized vessel ("digester").

Preferably, sub-step (iii) of the Kraft process (a) is carried out for several hours, more preferably for 2 to 24 hours, even more preferably 3 to 9 hours, most preferably for 3 to 5 hours. The duration of the "cooking" sub-step (iii) typically depends on the reaction conditions, i.e. the pH, pressure and temperature, and may further depend on the type and strength of the employed chopped lignocellulosic material.

Preferably, sub-step (iii) of the Kraft process according to (a) is carried out in a pressurized vessel ("digester") for at least 2 hours at a temperature of at least 150° C. Under such conditions, pulp and modified lignin-derived components may be separated from each other. Sub-step (iii) of the Kraft process according to (a) is preferably carried out at a pressure of at least 4 bar in the pressurized vessel, preferably at 5 to 10 bar.

Preferably, sub-step (iii) of the Kraft process is carried out at a temperature of 150° C. to 190° C., preferably 170° C. to 180° C. Such temperatures typically provide higher yields (by improved separation of the lignin and the cellulosic fraction) and process efficiency. Increasing the temperatures significantly beyond 200° C., in particular in combination with the applied overpressure may lead to undesired excessive degradation of the lignin and/or the cellulosic fraction and is unfavourable in terms of the energy consumption involved.

Sub-step (iii) of the Kraft process may be carried out either in a batch mode or in a continuous mode. For the continuous mode, the lignocellulosic starting material is fed into a digester at a rate, which allows the pulping reaction to be complete by the time the materials exit the reactor. The continuous mode is preferred to ensure higher throughput and improved efficiency. Digesters producing 1.000 tons or more of pulp per day are common and may be used according to the inventive method.

During the "cooking" sub-step (iii) of the Kraft process, lignin polymers and hemicellulose are preferably degraded to lower molecular weight degradation products, which are released from the cellulose scaffold as a result of the cooking step. Such lower molecular weight degradation products are typically more soluble in (strongly) basic solution than the polymers of the lignocellulosic starting material.

The modified lignin-derived components obtained from sub-step (iii) of the Kraft process according to (a) are commonly known as "Kraft lignin". These components are essentially unsulfonated or at least less sulfonated than "lignosulfonate" resulting from the sulphite process according to (b). Typically, they are more soluble in aqueous alkaline solution, preferably at a pH of greater than about 9 and reasonably soluble in strongly polar organic solvents. The average molecular weight of the lignin-derived components is generally between 1.000 and 4.000 Da, preferably 2.000 to 3.000 Da.

Average lignin-derived components obtained from sub-step (iii) of the Kraft process may comprise about 10 to 35 building blocks, preferably 10 to 25 building blocks, and thus, may have a "polymerization degree" of 10 to 35, preferably 10 to 25. The lignin-derived material typically exhibits a polydispersity of between 2 and 4, although it can be as high as 8 or 9. Material of such higher values of polydispersity may be typically employed for industrial grade applications, but does usually not allow its subsequent exploitation as basic material for the provision of a larger variety of organic target compounds as envisaged by the invention. Accordingly, polydispersity of the material obtained by sub-step (iii) of the Kraft process should not go beyond 6, preferably should be less than 5 or from 2 to 5. A "molecular formula" of $C_9H_85 O_2$ 1S0.1(OCH3)0.8(CO2H) 0.2 was previously reported for softwood Kraft lignin. About 4% by weight is typically free phenolic hydroxyl. (Lebo, S. E. et al, Lignin, Kirk-Othmer Encyclopedia of Chemical Technology, p. 18 of on-line version, (2001), John Wiley & Sons, Inc.). Kraft process-derived modified lignin-derived components typically also comprise biphenylic moieties, in particular when using lignocellulosic starting material being of spruce origin. Hence, spruce may be the preferred starting material for the inventive method, if dimeric biphenylic target products are desired.

Sub-Step (iv): Sulfonation

In optional sub-step (iv) of the Kraft process, the modified lignin-derived components obtained from sub-step (iii) may be sulfonated in order to increase their water-solubility over a wider pH range (i.e. in acidic or neutral solutions).

To that end, sulfonating agents known in the art, such as a solution of preferably concentrated sulfuric acid, may be added to the lignin-derived process stream. Aliphatic side chains are typically sulfonated, e.g. by the introduction of sulfonyl moieties as substituents of side chains of Kraft lignin. Sulfonation may occasionally also affect the aromatic rings of the Kraft lignin components.

By sulfonation of Kraft lignin, sulfonated modified lignin is obtained, which is herein understood as "sulfonated Kraft lignin".

Generally, sulfonation of sub-step (iv) confers increased solubility and surfactant properties to Kraft lignin. "Sulfonated Kraft lignin" shares characteristic structural or functional properties with "lignosulfonate" of the sulphite process, such as water solubility over a broader pH range. Both, Kraft process-derived "sulfonated Kraft lignin" and sulphite process-derived "lignosulfonate" are referred to as "sulfonated lignin". Kraft process-derived "sulfonated Kraft lignin" and sulphite process-derived "lignosulfonate" are generated under distinct chemical conditions resulting in structural distinct lignin-derived compositions. The average molecular weight of components of "sulfonated Kraft lignin" is typically lower than the average molecular weight of components of "lignosulfonate" resulting from the sulphite process. Accordingly, the molecular weight of the components of sulfonated Kraft lignin may typically be about 1.000 to 4.500 Da, preferably 2.500 to 3.500 Da.

For sulfonation according to sub-step (iv), overpressure and/or increased temperature may be applied. After a reaction period of preferably at least two hours, sulfonated Kraft lignin may be recovered, e.g., by water removal or by precipitation, e.g. with excess lime, as calcium lignosulfonates. As sulfonation confers improved water solubility properties to Kraft lignin, it makes such sulfonated lignin-derived material easier to separate in an aqueous environment from insoluble cellulosic material. In standard pulp and/or paper manufacturing plants operating under the Kraft process, additional sulfonation step (iv) (which may also be designated as "postsulfonation" for Kraft lignin) is therefore typically beneficially applied.

Sulfonation sub-step (iv) of the Kraft process (a) is preferably carried out at a temperature below 300° C., more preferably below 200° C. Such elevated temperatures preferably ensure both sufficiently high yields of sulfonated reaction products, while it avoids premature, i.e. uncontrolled thermal degradation of the lignin-derived Kraft lignin material. Thereby, it is ensured that the lower molecular weight (as compared to the natural lignin polymers) aromatic lignin-derived components remain intact (without uncontrolled degradation) for their further processing towards the inventive method's target compounds. Low molecular weight monomeric or dimeric target compounds are obtained by well-controlled decomposition of the modified lignin-derived components in downstream method step (3), followed by subsequent isolation (purification) in step (4). Accordingly, the largest portion of modified lignin-derived components possible resulting from step (2) shall be made available for controlled decomposition in downstream step (3). Otherwise, the yield of the target compound would be unfavorably reduced.

(b) Sulphite Process

Alternatively, the "sulphite process" (or: sulfite process) may be employed as a pulping process in step (2) of the inventive method. The sulphite process is the second most prevalent pulping process worldwide. It is typically a low pH pulping process in aqueous solution containing one or more of salt or non-salt agents exhibiting one or more of sulphite or bisulphite groups or anions. For the sulphite process, the lignocellulosic starting material is treated in aqueous solution at elevated temperature and pressure. The process yields "lignosulfonate", which is more water-soluble than "Kraft lignin". Sulphite pulping is generally less destructive than Kraft pulping, i.e. the natural lignin polymer is degraded to modified lignin-derived components being larger than the corresponding components in Kraft pulping. Thus, "lignosulfonate" typically has a molecular weight of about 3.000 to 100.000 Da, preferably 5.000 to 20.000 Da.

The sulphite process may preferably comprise the following sub-steps which are described in greater detail below:

(i) optionally pre-steaming the (preferably chopped) lignocellulosic material, wherein the (preferably chopped) lignocellulosic material is advantageously wetted and pre-heated with steam;

(ii) adding the (preferably chopped) lignocellulosic material to an aqueous, preferably acidic solution comprising a sulphite and/or bisulphite salt; and (iii) cooking the (preferably chopped) lignocellulosic material, which is provided (e.g. dispersed or and/or suspended) in said aqueous, preferably acidic, solution.

Step (i): Pre-Steaming

Optional sub-step (i) of the sulphite process is typically conducted under the same conditions as described for sub-step (i) of the Kraft process (see above).

Step (ii): Impregnation

In sub-step (ii) of the sulphite process, the lignocellulosic material is treated with an aqueous, preferably acidic sulphite and/or bisulphite containing solution used as a reactive agent (or "liquor").

The salt anions in the liquor may either be present as sulphites ($SO_3^{2-}$), and/or bisulphites ($HSO_3^-$), depending on the pH. At lower pH, i.e. under stronger acidic conditions, such as less than pH 2.5, the sulphite is typically provided as $HSO_3^-$. Counter cations may be sodium ($Na^+$), calcium ($Ca^{2+}$), potassium ($K^+$), magnesium ($Mg^{2+}$) or ammonium ($NH_4^+$). Particularly divalent (e.g. earth alkali) cations, such as calcium and/or magnesium, may be used as the counter cation. Sulphite pulping is preferably carried out under acidic conditions, preferably at a pH below 5, preferably from pH 1.5 to 5 or 1.5 to 4. The (acidic) pH may be adapted depending on the nature of the counter cation for the sulphite (bisulphite) anion.

Preferably, the sulphite or bisulphite salt comprised in the aqueous (preferably acidic) solution in step (ii) is a salt with a cationic counter ion preferably selected from the group consisting of sodium, calcium, magnesium and ammonium. The preferred salt is calcium bisulphite.

The preferred salt is calcium bisulphite, which may advantageously be employed, if the selected pH value for the sulphite process is 2.5 or less. Higher pH sulphite pulping (at a pH above pH 2.5 or, more specifically, above pH 4) generally employs monovalent ions, such as sodium or ammonium, as counter cations. However, it is not excluded that sulphite pulping may be carried out over a wider pH range, including alkaline conditions of about pH 7 to 12.

The "liquor" used in sub-step (ii) of the sulphite process may be provided as follows: Sulphur may be oxidized (burnt) with the stochiometrically adequate amount of oxygen to yield sulphur dioxide. Sulphur dioxide is preferably added, e.g. as a gas, to water to give sulphurous acid, which may be further diluted for its use as "pulping liquor".

In sub-step (ii) of the sulphite process, the pH of the aqueous preferably acidic solution is preferably 1 to 5 and more preferably 1.5 to 4. The temperature of the aqueous (preferably acidic) solution in sub-step (ii) of the sulphite process according to (b) is also typically less than 100° C., e.g. from 70° C. to 90° C. The lignocellulosic material may be brought into contact with the liquor for more than three hours, preferably 4 to 14 hours.

Step (iii): Cooking

In sub-step (iii) of the sulphite process, the preferably chopped and pre-treated ("impregnated") lignocellulosic material is "cooked" in the treatment solution.

Preferred reaction conditions during sub-step (iii) of the sulphite process may encompass one or more of the following: Duration: 2 to 24 hours, preferably 4 to 6 hours; Temperature: at least 120° C., preferably between 120° C. and 170° C., more preferably between 130° C. and 160° C.; Pressure: at least 4 bar, preferably between 5 and 10 bar in a pressurized vessel ("digester").

Preferably, sub-step (iii) of the sulphite process is carried out for 2 to 24 hours, preferably 4 to 6 hours.

Preferably, sub-step (iii) of the sulphite process is carried out at a temperature of at least 120° C., preferably between 120° C. and 170° C., more preferably between 130° C. and 160° C. The employed temperature may typically depend on the chosen reactive agents and their concentration.

Preferably, sub-step (iii) of the sulphite process is carried out in a pressurized vessel ("digester") preferably at a pressure of at least 4 bar, more preferably at 5 to 10 bar.

Preferably, sub-step (iii) of the sulphite process is carried out in a pressurized vessel at a pressure of at least 4 bar for at least 3 hours at a temperature of at least 120° C. Under such conditions, pulp and modified lignin-derived components may be separated from each other.

Sub-step (iii) of the sulphite process according to (b) may be carried out either in a batch mode or in a continuous mode. For the continuous mode, the lignocellulosic starting material is fed into a digester at a rate, which allows the pulping reaction to be complete by the time the materials exit the reactor. The continuous mode is preferred to ensure higher throughput and improved efficiency. Digesters producing 1.000 tons or more of pulp per day are common and may be used according to the inventive method.

The modified lignin-derived components resulting from the sulphite process are generally referred to as "lignosulfonate". Due to the nature of the sulphite process, "lignosulfonate" typically contains significant amounts of sulphur-based moieties (typically in the form of sulfonate groups), for example, in the aliphatic side chains of the modified lignin-derived components.

"Lignosulfonate" is thus a complex (heterogeneous) mixture of modified lignin-derived components, i.e. water-soluble anionic lignin-derived polyelectrolytes, which carry —$SO_3H$ functional groups. Lignosulfonate typically exhibits by its heterogeneous components a broad molecular weight range (broader than observed for Kraft lignin). Lignosulfonate is polydisperse with a polydispersity being typically higher than that of the Kraft process (about 4 to 9). As the sulphite process is less destructive than Kraft pulping, it does not degrade lignin to the same extent as the Kraft process. Thus, sulphite process-derived lignosulfonate typically has a higher average molecular weight than Kraft lignin as described herein. A maximum molecular weight of 140.000 Da is reported for softwood lignosulfonates, while maximum values for hardwoods are usually lower, e.g. lower than 50.000 Da. The typical range of the molecular weight for lignosulfonate polymers is about 5.000 to 50.000 Da, preferably about 5.000 to 20.000 Da (Brogdon, B. N., Dimmel, D. R. J. Wood Chem. Technol. 1996, 16, 297). Usually, it comprises about 10 to 300 building blocks, preferably 20 to 200, most preferably 25 to 150 building blocks, and thus, may have a "polymerization degree" of 10 to 300, preferably 20 to 200, most preferably of 25 to 150. It typically exhibits a higher sulfur content (about 3% to 8% w/w) than (unsulfonated) Kraft lignin (having a sulfur content of typically less than 1% w/w). Lignosulfonates are used in the art as low-value chemicals in tanning leather, making concrete, drilling mud and drywall, such as binders or additives for building material. Lignosulfonates are typically soluble in water over essentially the entire pH range. Sulphite process-derived lignosulfonate may also be soluble in highly polar organic and amine solvents. Its approximate "molecular formulas" are described as $C9H8.5O2.5(OCH3)0.85(SO_3H)0.4$ for softwood or as $C9H7.5O2.5 (OCH3)1.39 (SO_3H)0.6$ for hardwood, respectively, as starting material for sulphite process-derived lignosulfonate. Sulphite process-derived lignosulfonate may comprise biphenylic moieties for some of the components of the larger number of components representing the "lignosulfonate" fraction. That holds specifically for lignocellulosic material of spruce origin. Hence, spruce may be the preferred starting material for the inventive method, if biphenylic precursor or target compounds are desired.

(c) Further Pulping Methods

Organosolv Process, Alcell Process

Step (2) of the inventive method may alternatively include pulping by using the organosolv process.

The organosolv process typically involves treatment of wood or bagasse with various organic solvents.

The "Alcell process" is one of the most commonly applied organosolv processes and includes dissolution of lignin in either ethanol or ethanol/water mixtures.

Advantageously, organosolv processes allow to automatically generate separate process streams of cellulose, hemicelluloses, and lignin and individual processing thereof. Organosolv processes are further environmentally attractive, as it does not employ aggressive reactive agents (e.g. sulphides) and harsh conditions as used in the Kraft or sulphite processes.

The organosolv process typically yields "organosolv lignin" as modified lignin-derived components. Organosolv lignin It has a low molecular weight of about 1.000 to 2.000 Da. It is typically low in sulphur content and also of higher purity than the modified lignin-derived components obtained from other pulping processes. A disadvantage of the organosolv process are the costs of solvent recovery.

Steam Explosion Process

Another pulping process, which may be employed by the present invention, is the "steam explosion process" involving steam impregnation under pressure followed by rapid pressure release, which separates the lignocellulosic constituents. Covalent linkages of 3D lignin are ruptured as well, such that a complex mixture of lignin derived fragments is obtained. Typically, wood or bagasse is exposed to steam at overpressure and elevated temperature, such as a total pressure of 1.38 to 3.45 MPa and a temperature from about 180° C. to about 230° C. for about 1-20 min before rapid pressure release. The molecular weight distribution of the lignin fragments obtained by the steam explosion process is typically similar to the organosolv process.

Other Methods

Several other methods for isolating (modified) lignin from wood or plant biomass or starting material are described in the art as well, including the "ammonia fiber explosion" (AFEX) process and the "hot water process", which may also be employed as step (1.2). Finally, the "dilute acid process" as a further option for sub-step (1.2) of the inventive method may ensure effective separation of lignin from other biomass components. It may, however, provide lower yields. Corrosion of equipment (due to the acidic environment) may also be an issue. The "alkaline oxidation process" may use $O_2$ or $H_2O_2$ to degrade lignin. However, the process may suffer from slower delignification rates. The dilute acid process and alkaline oxidation process may both provide modified lignin-derived components with similar molecular weight (distributions) as organosolv lignin.

Separation of Celluose-Derived and Lignin-Derived Process Stream A

The pulping process preferably yields a process stream A that is subsequently separated to obtain a cellulose-derived process stream A and a lignin-derived process stream A. The process stream A originating from the pulping process contains preferably pure cellulosic fibrous material ("pulp"), which is typically non-dissolved, but dispersed or suspended in the consumed pulping liquor—which is enriched in modified lignin-derived material in dissolved, suspended and or dispersed form. The pulp may be separated from the consumed pulping liquor by mechanical means (e.g. sieving, centrifuging), yielding the pulp as the cellulose-derived process stream A, and the modified lignin-derived material dissolved, suspended and or dispersed in the consumed pulping liquor as the lignin-derived process stream A. Put differently, the main process stream A emerging from the pulping process typically comprises a lignin-derived fraction and a cellulose-derived fraction, which are separated to obtain a cellulose-derived process stream A and a lignin-derived process stream A.

Methods for separating the cellulose-derived process stream from the lignin-derived process stream are known in the art and include, without limitation, blowing, sieving, countercurrent flow, centrifugation, filtration, washing, stripping, ion-exchange, or any combination thereof, with blowing, sieving and/or washing being preferred.

A preferred method of separating the cellulose-derived process stream and lignin-derived process stream from the process stream originating from the pulping process is by "blowing" the cellulose scaffold into a collection tank ("blow tank"). The residual cellulosic scaffolds may be blown into a blow tank that usually operates at atmospheric pressure. This blowing typically releases steam and volatiles. Volatiles are understood herein as organic chemicals that have a high vapor pressure at ordinary room temperature. Typically, they are characterized by an individual odor. The volatile fraction may be condensed and collected. When employing "northern softwoods" as the lignocellulosic starting material for the inventive method, the volatile fraction typically encompasses raw turpentine.

Pulp separation may preferably further comprise a step of separating e.g. dispersed cellulose from the liquid fraction of the process stream originating from the pulping process. To that end, pulp separation may deploy sieving, screening and/or centrifugation techniques. For sieving of the process stream originating from the pulping process, sieves may typically be arranged in a multistage cascade-like assembly. Thereby, considerable amounts of pulp may preferably be sieved, and thus, separated from the liquid fraction of the process stream originating from the pulping process.

The main process stream originating from the pulping process (optionally subject to blowing, sieving and/or filtration) may also undergo one or more washing steps to separate cellulose (pulp)- and lignin-derived fractions. Thereby, (residual) dispersed cellulose fibers are separated from said process stream. Usually, a pulp mill encompasses 3-5 washing stages in series. Pulp washing as used herein is typically carried out by pulp washers using counter-current flow in between two subsequent stages such that the pulp moves in the opposite direction to the flow of washing water. While the washing water merges in the lignin-derived process stream, cellulose is effectively separated and ready for pulp and paper production. Various techniques may be involved in pulp washing, such as thickening/dilution, displacement and diffusion. The washing equipment may comprise, for example, pressure diffusers, atmospheric diffusers, vacuum drum washers, drum displacers and wash presses.

Accordingly, pulping and subsequent pulp separation preferably yields one (essentially pulp-free) lignin-derived process stream and one cellulose-derived process stream.

The terms "cellulose-derived process stream" and "lignin-derived process stream" are defined above. Briefly, the cellulose-derived process stream preferably comprises a mixture of (enriched) cellulose fibrous material. The lignin-derived process stream preferably comprises modified lignin-derived components, such as (sulfonated) "Kraft lignin" and/or "lignosulfonate", depending on the employed pulping process, and further optionally (consumed) chemical reactants, reaction products, by-products, impurities, catalysts, and usually also hemicellulose and/or its hydrolysis products (poly-, oligo and/or monosaccharides). Typically, the components in the lignin-derived process stream are dissolved, suspended or dispersed in the consumed pulping liquor. Preferably, the lignin-derived process stream is substantially pulp-free.

The cellulose- and lignin-derived process stream A obtained from step 2) of the inventive method may further be processed as single process streams or may each be separated to obtain at least two (partial) cellulose- and/or lignin-derived process streams B, C, D . . . .

In such a case (and in particular in case of liquid process streams, such as the preferably liquid lignin-derived process stream), the sum of the flow rates of the partial process streams is typically equal to the flow rate prior to process stream partitioning. The flow rate of each of the two or more partial process streams may correspond to e.g. up to 50%, 33%, and 25% etc. of the flow rate of the process stream prior to partition. Alternatively, one of the partial process streams may exhibit a higher flow rate than the other partial process stream(s). Typical percentile ratios of flow rates may be 5:95, 10:90, 15:85, 20:80, 25:75, 30:70, 35:65, 40:60 and 55:45. When partitioning a process stream e.g. into three partial process streams, each process stream may have a flow rate corresponding to one third of the flow rate of the process stream prior to partitioning. Alternatively, one or two partial process streams may have a flow rate higher or lower than the third process stream, provided that the sum of the flow rates of the partial process streams preferably equals the flow rate of the process stream prior to partitioning.

By separating e.g. the lignin-derived process stream A, a partial lignin-derived process stream may be used for (conventional) combustion as an energy source, a partial lignin-derived process stream may be processed via alternative routes, and a partial lignin-derived process stream may e.g. be used for storing. Thereby, process stream partitioning may provide a "buffer capacity" depending on the status of the plant and the turnover of the method as a whole, which adds versatility and efficiency to the method, preferably without generating extra waste.

Process stream separation may be carried out by technical means known in the field of fluid process technology. Preferably, the partitioning means are adjustable in such a way, that defined portions of the single process stream may be mechanically separated into two or more, three or more or four or more partial process streams. The means for separating may be selected from a flap, hatch, clack, lid, valve, damper or shutter or a combination thereof. Said means may operate electrically and/or hydraulically. Alternatively, the process stream may be separated into partial process streams by vacuum and/or pressurized gas, i.e. portions of the process stream may be sucked or blown into two or more passages. Therein, a passage is understood as any form of duct, which passes the respective process stream to its next stage. The partitioning means and/or of the passages conducting the partial process streams are typically made of non-corroding metal, preferably coated or non-coated stainless steel.

When using the Kraft process for pulping in step 2) of the inventive method, the (essentially pulp-free) lignin-derived process stream, is commonly designated as "black liquor" (due to its color). When using the sulphite process for pulping in step 2) of the inventive method, the (essentially pulp-free) lignin-derived process stream is commonly designated "brown liquor".

As discussed above, the (essentially pulp-free) lignin-derived process stream A typically comprises modified lignin-derived components and random fragments thereof (i.e. lignin-derived molecules formed during the pulping process, but having a lower molecular weight than the typical modified lignin-derived components) and hydrolysis products of hemicellulose. Hemicellulose is typically hydrolyzed in any pulping process, e.g. in acidic or alkaline medium, yielding smaller pieces of hemicellulose such as poly- or oligosaccharide fragments or even mono- or disaccharides thereof, which are all usually dissolved in the pulping liquor. Further, (in)organic salts as residual components of the reactive agents used for the pulping process may be comprised in the lignin-derived (essentially pulp-free) process stream, such as sodium carbonate and/or sodium sulphate.

Kraft pulping may be the pulping method of choice in step 2) of the inventive method. As discussed above, Kraft pulping in step 2) may preferably comprise: treating the lignocellulosic material with an aqueous alkaline solution comprising a Kraft pulping reactive agent selected from the group consisting of a sulfide agent, a sulfhydryl agent, and a polysulfide agent and a sulfate salt; cooking the lignocellulosic material in said aqueous alkaline solution; and optionally separating the cellulose-derived fraction and lignin-derived fraction to obtain at least one cellulose-derived process stream A ("brown liquor"), and at least one lignin-derived process stream A ("black liquor").

Step (3): Pulp Processing

Step 3) of the inventive method comprises at least one step of processing the cellulose-derived process stream. The cellulose-derived process stream may be subjected to any suitable technique that is preferably useful for providing a desired cellulose-derived product, such as a paper or paperboard product, or a valuable chemical product. The type of treatment will generally depend on the desired end product obtained from the cellulose-derived process stream.

After pulping, the obtained pulp may generally processed in wide variety of ways e.g. to remove residual undesired components, and/or to recover and recycle any residual pulping liquor retained in the pulp. Accordingly, step 3) of the inventive method may comprise subjecting the pulp to one or more of the following sub-steps:
(a) Washing;
(b) Delignification and/or bleaching; and/or
(c) Chemical transformation reactions.

The sub-steps may be performed in any suitable order. Each sub-step may optionally be repeated as desired. The sub-steps are discussed in greater detail below.

Washing

The cellulose-derived process stream may be subjected to at least one washing step before further downstream processing. Washing may be applied to clean the pulp from residual liquor used in the pulping process, or other impurities, by-products, catalysts and the like retained in the pulp.

During the washing step, residual pulping liquor is washed from the pulp, e.g. using pulp washers (such as "brown stock washers" for Kraft pulp and "red stock washers" for sulphite pulp. Efficient washing is critical to maximize the recycling of pulping liquor and to minimize carryover of the pulping liquor into downstream processing facilities, in particular bleach plants, because excess pulping liquor may increase consumption of bleaching chemicals (typically due to binding of the organic compounds dissolved in the liquor to the bleaching chemicals, thereby increasing their consumption).

Many different kinds of techniques are known and currently in use for the washing operation. Washing in step 3) of the inventive method may be accomplished using the following kind of equipment or techniques, which are described in greater detail in Miliander, Lars. "Equipment for Pulp Washing." *Pulping Chemistry and Technology*. Monica Ek et al. (Ed.). Berlin: De Gruyter, 2009. 176-188:

Vacuum filters or pressure filters;
High-heat washing in continuous digesters;
Atmospheric and pressure diffusers;
Horizontal belt washers;
Displacement or wash presses; and/or
Displacement filter washers.

Delignification and Bleaching

Chemical pulping typically does not completely remove lignin from the cellulose-derived process stream. Pulp obtained from chemical pulping still comprises small amounts of lignin, usually in the order of 2-5%, depending on the type of lignocellulosic starting material and the chosen process parameters. The residual lignin or lignin components present in the pulp contain chromophores causing a dark brown colour. However, many paper products that are the desired end products of pulp processing, such as printing and writing paper, require bright pulps.

Accordingly, step 3) of the inventive method may preferably comprise at least one step of delignification and/or bleaching of the pulp in order to remove the residual lignin and provide high purity cellulose. To that end, the pulp may typically be treated with oxidizing agents in order to oxizide, and thereby decompose, solubilize and finally remove residual lignin from the cellulose fibers. As an additional advantage, bleaching and delignification may not only increase the brightness of the pulp, but also its purity by removing impurities, extractives and bacteria which may in particular be importance if the resulting cellulose is intended for producing food or liquid board.

A variety of different chemically reactive agents may be used and optionally be applied in a stepwise fashion within a treatment sequence in step 3) of the inventive method. Preferably, the pulp may be subjected to one or more oxidation treatments, optionally followed by a washing step or treatment with an alkaline agent (typically sodium hydroxide) for extraction of lignin dissolved lignin and/or remove chemically reactive agents, reaction products, by-products, impurities or catalysts from the cellulose (typically in preparation of the next processing step). The chemically reactive agents chosen and the sequence in which they are used depend on a number of factors, such as the relative cost of the bleaching chemicals, type and condition of the pulp, desired brightness of the pulp, and sometimes in response to environmental guidelines and regulations. Suitable oxidizing agents for use in bleaching in step 3) of the inventive method include chlorine gas, chlorine dioxide, sodium hypochlorite, hydrogen peroxide, and oxygen. Some chemically reactive agents may be primarily used for delignification, or for bleaching, or for both, depending on the sequence of treatment steps and the process parameters under which they are employed. However, said agents are commonly referred to as "bleaching agents" or "oxidizing agents" herein. The chemically reactive bleaching agents (usually dissolved in a suitable solvent, optionally in combination with further suitable stabilizing and buffering agents) used for bleaching are commonly referred to as the "bleaching liquor".

Generally, bleaching of the pulp may be accomplished by a series of alternating oxidation and extraction treatments, as described in detail in Gellersted, Göran "Chemistry and Bleaching of Pulp". *Pulping Chemistry and Technology*. Monica Ek et al. (Ed.). Berlin: De Gruyter, 2009. 202-237.

Without wishing to be bound by specific theory, it is thought that chemically reactive bleaching agents may exert their function by oxidizing aromatic lignin units having a free hydroxyl group, thereby forming a phenoxy radical that readily reacts with superoxide radicals or oxygen molecules and finally yields an organic hydroperoxide. Hydroperoxides may, in particular in the presence of transition metals, decompose, resulting in the formation of highly reactive hydroxyl and superoxide radicals. Hydroxyl radicals are known as powerful oxidants which readily react with lignin or carbohydrates, thereby forming further organic radical intermediates that further react with lignin or carbohydrates. Particularly the oxidative cleavage of aromatic lignin units may lead to the formation of acidic acid groups, rendering the resulting lignin-derived compounds more hydrophilic und thus more easy to dissolve and remove from the pulp.

As described above, several bleaching stages may be combined to achieve efficient bleaching. Each treatment stage is assigned a capital letter. Typically, bleaching sequences are identified by the combination of letters indicating the particular sequence of steps used. E.g., a CED sequence includes treatment with chlorine (C) in the first stage, followed by alkaline extraction (E) in the second stage and chlorine dioxide (D) in the third stage. Parentheses indicate that two bleaching agents are used together in the same stage. For instance (CD) indicates that chlorine and chlorine dioxide are used in the same stage. Generally, the use of parenthesis may indicate that the chemicals are charged simultaneously or sequentially in the same step. A plus between the letters (e.g. (C+D)) specifically indicates simultaneous loading. The chemically active agent that is used in higher quantities is typically written first.

Oxygen (Pre-)Bleaching (O-Stage)

Oxygen may preferably be used in a first treatment step ("O-stage") directly after pulping and isolating the pulp ("oxygen pre-bleaching"). Oxygen may, however, also be used between and/or after other bleaching steps described herein. Advantageously, oxygen treatment preferably reduces pollution, increases pulp strength and reduces bleaching consumption and bleaching cost. Under some conditions oxygen bleaching may also increase pulp yield.

Step 3) of the inventive method may thus preferably comprise subjecting the pulp to oxygen treatment, preferably for delignification and/or (pre)bleaching. Thereby, the pulp is preferably contacted with gaseous oxygen at an alkaline pH. The reaction typically requires a high oxygen pressure. Therefore, oxygen is preferably provided at a pressure of at least about 0.6 MPa. Preferably, the pH may be above about 9, more preferably between about 10-11. The reaction is preferably carried out at elevated temperatures of at least about 80° C., at least about 90° C. or at about 100° C., preferably at between about 90-100° C. The reaction time may typically be about 60 minutes or less, such as about 60-30 minutes. The reaction may take place under constant mixing or stirring.

Chlorine Prebleaching (C-Stage)

Chlorine ($Cl_2$) has for a long time been the preferred bleaching chemical in the first bleaching step due to its low cost, high bleaching efficacy and very high selectivity towards lignin. However, environmental concerns regarding the generation of chlorinated organic compounds during chlorine bleaching halted its use.

Nevertheless, chlorine bleaching as a highly efficient bleaching method is still applied today and is generally also envisaged in the context of the present invention.

Step 3) of the inventive method may thus preferably comprise subjecting the pulp to chlorine treatment, preferably for delignification and/or (pre)bleaching. Thereby, the pulp is preferably contacted with chlorine ($Cl_2$) and/or hypochlorous acid (HOCl)/hypochlorite ($OCl^-$) at acidic pH. Preferably, the pH may be below about 3, more preferably the pH may be about 2. The reaction is preferably carried out at ambient temperature of at least about 10° C., preferably between about 10-40° C. The reaction time may typically be about 60 minutes.

Chlorine Dioxide and/or Chlorine Prebleaching ($D_0$-Stage)

A combination of chlorine and chlorine dioxide may advantageously increase delignification of the pulp during pre-bleaching. Alternatively, chlorine dioxide may be used alone. Chlorine dioxide and/or chlorine pre-bleaching may be either accomplished directly on the unbleached pulp, or on the pulp after a preceding step of oxygen bleaching ("O-stage"). In the latter case, the predominant function of the chlorine dioxide and/or chlorine is delignification with little or no brightening effect on the pulp. However, chlorine dioxide may also used as an efficient brightening agent at the end of a bleaching sequence, which is of particular use in the preparation of fully bleached kraft pulp.

Step 3) of the inventive method may thus preferably comprise subjecting the pulp to chlorine dioxide treatment ($D_0$-stage) treatment, preferably for delignification and/or pre-bleaching. Thereby, the pulp is preferably contacted with chlorine dioxide at acidic pH. The reaction is typically conducted at atmospheric pressure. Preferably, the pH may be about 4 or less, more preferably about 3 or less, most preferably between 2-3. The reaction is preferably carried out at elevated temperatures of at least about 30° C., more preferably at least about 40° C., even more preferably between about 40-70° C., and most preferably between about 65-75° C. The reaction time may typically be about 60 minutes or less, preferably about 30-60 minutes, more preferably about 45-60 minutes. Optionally, chlorine dioxide may be combined with chlorine. To that end, preferably chlorine dioxide pre-bleaching is conducted (preferably as described above), followed by a bleaching step where a combination of chlorine and chlorine dioxide is added.

Final Bleaching with Chlorine Dioxide ($D_1$/$D_2$-Stage)

Final bleaching of pulp is often carried out with one or two chlorine dioxide bleaching steps. The conditions used in these two D-stages ($D_1$, $D_2$) are different to the conditions used in the $D_0$-stage.

Step 3) of the inventive method may thus preferably comprise subjecting the pulp to chlorine dioxide treatment ($D_1$-stage, $D_2$-stage), preferably for delignification and/or bleaching. Thereby, the pulp is preferably contacted with chlorine dioxide at acidic pH. The reaction is typically conducted at atmospheric pressure. In the $D_1$-stage, the pH may be about 5 or less, more preferably about 4 or less, most preferably between 3-4. The reaction is preferably carried out at elevated temperatures of at least about 40° C., more preferably at least about 50° C., most preferably between about 55-75° C. The reaction time may typically be at least about 60 minutes, more preferably between 1-3 hours. In the $D_2$-stage, the pH may be about 5.5 or less, more preferably about 4.5 or less, most preferably between 3.5-4.5 The reaction is preferably carried out at elevated temperatures of at least about 50° C., more preferably at least about 55° C., most preferably between about 65-85° C. The reaction time may typically be at least about 60 minutes, more preferably between 1-3 hours.

Extraction Stage (E-Stage)

Bleaching of pulp with any of the methods described herein may preferably be followed by an alkaline extraction stage ("E-stage"). Without wishing to be bound by specific theory, it is envisaged that the E-stage increases the water-solubility of oxidized lignin components by neutralizing carboxyl groups. That is of particular importance in chlorine dioxide and chlorine bleaching, which are conducted under acidic conditions.

Step 3) of the inventive method may thus comprise subjecting the pulp to an alkaline treatment ("E-stage"), preferably for lignin dissolution and removal Thereby, the pulp is preferably contacted with an alkaline extraction agent, preferably sodium hydroxide. The reaction time may typically be about 60 minutes. The reaction temperature may preferably be between about 55-110° C., more preferably between about 70-95° C. Preferably, an oxidant like oxygen, hydrogen peroxide or both may be added in order to preferably further increase the extent of delignification.

Ozone Bleaching (Z-Stage)

Ozone reacts rapidly and more or less instantly with the pulp and advantageously is capable of efficiently removing extractives, resulting in decreased odour and taste in the pulp, and hexenuronic acids, which improves the brightness stability of the pulp and reduces the consumption of final bleaching agents.

Step 3) of the inventive method may thus preferably comprise subjecting the pulp to ozone treatment ("Z-stage"), preferably for delignification and/or (pre)bleaching. Thereby, the pulp is preferably contacted with gaseous ozone at an acidic pH. The reaction may typically be conducted at atmospheric pressure or a pressure of at least 5-10 bar. Preferably, the pH may be about 4 or less, more preferably about 3 or less, most preferably between 2-3. The reaction is preferably run at temperatures of about 70° C. or less, preferably about 60° C. or less, more preferably between about 30-60° C. The reaction time may typically be about a few seconds or more, preferably up to 1 minute.

A sequential effect can be achieved by combining the ozone stage with chlorine dioxide bleaching. Thereby, a certain amount of chlorine dioxide can be replaced by the use of ozone.

Chelating Stage (Q-Stage)

For some bleaching stages, and in particular hydrogen peroxide bleaching, the metal ion content in the pulp is an important variable for efficient bleaching. All pulps contain metal ions which may cause decomposition of hydrogen peroxide and a reduced bleaching efficacy. That particularly holds true for manganese, copper and iron ions. However, some metal ions may even be beneficial for bleaching, such as magnesium and calcium ions, and their presence in the pulp may be acceptable or even desired during bleaching.

Step 3) of the inventive method may thus include the removal of metal ions either by an acidic treatment at a pH of about 2, or by adding a chelating agent to the pulp at neutral pH ("Q-stage"). In either case, the treatment may preferably followed by a subsequent washing step. Suitable chelating agents are preferably capable of forming stable complexes with the undesired metal ions (Fe, Mn, Cu) that can be removed by the following washing step, and may preferably be selected from EDTA and DTPA. The pulp may thus preferably be contacted with a suitable chelating agent. The pH is preferably chosen depending on the particular chelating agent used and may be acidic to neutral from about 4-7 or 9-10 in alkaline Q stages. The reaction is preferably carried out at elevated temperatures of at least about 40° C., more preferably at least about 50° C., even more preferably between about 50-80° C. The reaction time may range from about 5 minutes or more to about 2 hours. EDTA and DTPA are preferred chelating agents and may be added in an amount of about 0.2-0.4 wt %.

Hydrogen Peroxide Stages (P-Stage)

Hydrogen peroxide bleaching may be applied as a final stage of a bleaching sequence for increased bleaching of the pulp, or may be added in the beginning of the sequence mainly for delignification. Hydrogen peroxide may also be used as a reinforcement of the extraction stage and the oxygen stage.

Step 3) of the inventive method may thus preferably comprise subjecting the pulp to hydrogen peroxide treatment ("P-stage"), preferably for delignification and/or (pre) bleaching. Thereby, the pulp is preferably contacted with hydrogen peroxide at alkaline pH. Hydrogen peroxide may preferably be added in a concentration of about 0.5-4 wt %, more preferably about 1-2 wt %. The reaction is typically conducted at a pressure of between about 3-8 bar. Preferably, the pH may be about 9 or more, more preferably about 10 or more, most preferably between about 10.5-11. The reaction is preferably carried out at elevated temperatures of at least about 70° C., more preferably at least about 80° C., most preferably between about 80-110° C. The reaction time may typically be about 60 minutes or more, preferably about 1-3 hours.

Subsequently, the (pre-treated) pulp may preferably be contacted with a bleaching liquor comprising hydrogen peroxide, optionally in combination with sodium silicate as a stabilizing and buffering agent, in an alkaline solution. Pulp may be contacted with the hydrogen peroxide bleaching liquor at a temperature of about 100° C. or less, such as about 60-70° C. In particular, kraft pulp may require higher temperatures of around 100° C. for efficient alkaline hydrogen peroxide bleaching.

Peracid Treatment (T-Stage)

Peracids or peroxy acids containing perhydroxide groups (OOH) other than hydrogen peroxide may also be used for pulp treatment. Preferred peracids in this context include peracetic acid ($CH_3COOH$), performic acid ($CH_2O_3$) and peroxy-monosulfuric acid ($H_2SO_3$). These peroxidizing acids are stronger acids than hydrogen peroxide and may be used at milder conditions. Usually, peracid treatment is used in combination, optionally simultaneously, with other bleaching treatments to achieve extra high brightness.

Step 3) of the inventive method may thus preferably comprise subjecting the pulp to peracidic acid treatment ("T-stage"), preferably for delignification and/or (pre) bleaching. Thereby, the pulp is preferably contacted with peracetic acid at acidic to neutral pH. The pH may be about 7 or less, more preferably about 6 or less, most preferably between 4-6. The reaction is preferably carried out at elevated temperatures of at least about 50° C., more preferably at least about 60° C., most preferably between about 60-80° C. The reaction time may typically be at least about 1 hour or more, preferably between 1-3 hours. In the T-stage, the peracid, e.g. peracetic acid, may be used in a concentration of between 0.5-1.0 wt %.

Further Agents

Further agents that may be used for pulp treatment include dimehyldioxirane; oxygen in combination with polyoxometalates (POMs) such as $[PMo_{(12-n)}V_nO_{40}]^{(3+n)-}$ or $[X^{n+1}VW_{11}O_{40}]^{8-n)-}$ where $X(n+1)=Al^{3+}$, $Si^{4+}$ or $P^{5+}$; or oxidative enzymes such as lignin peroxidases, manganese peroxidases, and/or laccases, optionally in combination with 1-hydroxybenzotriazole and oxygen.

Step 3) of the inventive method may thus further comprise a step of treating the pulp by contacting the pulp with any of the aforementioned agents. The agents may optionally be used in combination with each other, or added during any of the treatment steps described herein.

Typically, step 3) of the inventive method includes a combination of delignification and/or bleaching sub-steps (or "stages") as described in the foregoing. The number of stages is usually between 3-5. The sequence of steps and conditions used for achieving delignification and/or bleaching of the pulp may depend on the lignocellulosic starting material, the pulping method and the desired end product of the pulp processing step (e.g. high quality paper versus low quality paper versus cellulose-derived chemicals).

Often, so called ECF (elemental chlorine free)- or TCF (totally chlorine free)-sequences may be preferred for environmental reasons.

Typical (partial) treatment sequences that may be employed in step 3) of the inventive method in particular for treating kraft pulps include the following:

D(EO); D(EO)D; OQPTP; OQ(PO)DD; O(EOP)Q(PO)Q (PO)Q(PO), (OO)Q(EP)Q(PO); OQ(PO); QQPD(EOP)D (e.g. for softwood kraft pulps); OQPD (e.g. for hardwood kraft pulps).

Sulphite pulps are typically different from kraft pulps in that they are brighter and easier to bleach to full brightness. That is due to the fact that residual lignin in sulphite pulps is usually sulfonated and thus more hydrophilic. Furthermore, sulphite pulps typically exhibit less strong bonds between phenylpropane lignin building blocks and contain fewer or nor hexuronic acids.

Thus, typically fewer bleaching stages and/or less bleaching chemicals are requires to achieve bleaching of sulphite pulps. Typical (partial) treatment sequences that may be employed in step 3) of the inventive method in particular for treating sulphite pulps include the following: (EOP)Q(PO); ZEP; or (EO)P.

Chemical Transformation

The pulp may be used to manufacture a large variety of derivatives, esters and ethers. A larger proportion of cellulose is typically used to produce regenerated cellulose, e.g.

as Rayon fibres, Cellophane and Lyocell. To that end, washed and preferably bleached pulp may be subjected to at least one chemical transformation step. The processing of cellulose for production of regenerated cellulose of cellulose derivatives typically requires a cellulose of high purity, which is also referred to as dissolving pulp. "Dissolving pulp", or "dissolving cellulose", is bleached pulp that has a high cellulose content (>90%). Such high purity cellulose is typically obtained by choosing the parameters of the pulping process (in particular Kraft or sulphite pulping) appropriately such that the amount of hemicellulose in the fibres is reduced to a minimum. Furthermore, the obtained pulp is preferably washed and bleached to high brightness in order to remove all residual lignin. Alternatively, the steam explosion process described above may be used for pulping as it degrades most of the hemicellulose fibres into low molecular weight sugars and oligosaccharides.

Step 3) of the inventive method may thus preferably include a sub-step of subjecting the pulp to at least one chemical transformation reaction. The type of chemical transformation(s) and process parameters is suitably chosen depending on the desired end product. Preferred sub-steps for manufacturing cellulose-based products as an integral part of the inventive method are discussed in the following.

Regenerated Cellulose

Preferably, the pulp may be subjected to washing and bleaching as described above. Subsequently, the pulp may be treated with strong alkali (mercerisation), preferably in order to adjust the degree of polymerization, followed by reaction with carbon disulphide ($CS_2$).

In the mercerisation step, cellulose I may preferably be converted to cellulose II. Treatment with carbon dioxide preferably converts the cellulose II to c. Subsequently, the cellulose xanthate is preferably treated with an alkaline reagent, typically aqueous sodium hydroxide. Finally, the cellulose xanthate is contacted with a solution of sulfuric acid, which preferably regenerates the cellulose as fine filaments resulting in rayon fibres.

Accordingly, step 3) of the inventive method may include the following sub-steps for the preparation of rayon fibres from pulp:

(a) provision of preferably washed and bleached pulp;

(b) treatment of pulp with alkaline agent, preferably sodium hydroxide (mercerisation);

(c) optionally beating the pulp;

(d) contacting the pulp with carbon dioxide, thereby preferably obtaining a so-called "viscose solution" of cellulose xanthate;

(e) contacting the cellulose xanthate obtained from step (d) with an alkaline agent, preferably aqueous sodium hydroxide;

(f) optionally filtering, deaerating and/or ripening of the cellulose xanthate obtained from step (e)

(g) treatment with sulfuric acid, optionally by extrusion through a spinnerette into a HCl solution; and (h) obtaining rayon fibres.

Preferably, the steps may be conducted in alphabetical order (a)-(h) and each step is performed on the intermediate product obtained from the preceding step.

The formation of sodium cellulose xanthate (bottom) starting from cellulose (top) according to the above method is shown in the reaction scheme below:

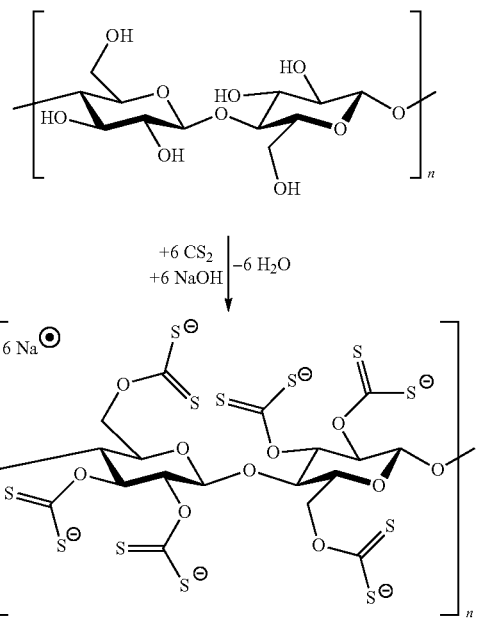

Cellulose Derivatives

Alternatively or additionally (if in step 3) the pulp is separated into several cellulose-derived process streams), optionally after washing and/or bleaching, the pulp can be used to prepare cellulose derivatives such as carboxymethylcellulose (CMC), ethylhydroxyethylecellulose (EHEC), cellulose acetate or cellulose nitrate and their derivatives.

CMC can advantageously finds use in a variety of applications in the food, pharmaceutical and cosmetic industry as a taste- and smell-free non-toxic thickening agent, stabilizer or disperging agent.

CMC may generally be obtained by subjecting the pulp to mercerisation, followed by reaction with sodium monochloroacetate to form an ether linkage. After neutralisation, washing and beating, the product is dried as its sodium salt.

Accordingly, step 3) of the inventive method may include the following sub-steps for the preparation of carboxymethylcellulose:

(a) provision of preferably washed and bleached pulp;

(b) optionally beating the pulp;

(c) treatment with an alkaline agent, preferably sodium hydroxide (mercerisation);

(d) treatment with sodium monochloroacetate ($ClCH_2COOH$), preferably for etherification and obtaining carboxymethylcellulose;

(e) neutralization, optionally with an acidic agent such as HCl;

(f) optionally washing, beating and/or drying; and (g) obtaining CMC, preferably sodium-CMC.

Preferably, the steps may be conducted in alphabetical order (a)-(g) and each step is performed on the intermediate product obtained from the preceding step.

Preferably, the CMC obtained by sub-steps (a)-(g) of step 3) of the inventive method described above may be characterized by General Formula (4) below:

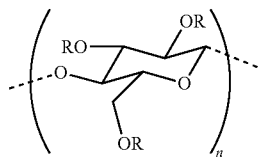

R = H or CH$_2$CO$_2$H (4)

EHEC forms colloidal solutions in water that are useful for water retention in cement and other applications in the construction industry. Furthermore, EHEC finds use as a thickening and disperging agent and stabilizer in water-based latex paints.

EHEC may generally be obtained by subjecting the pulp to mercerisation, followed by reaction with ethylenoxide to form hydroxyl-polyhydroxy ether groups.

Accordingly, step 3) of the inventive method may include the following sub-steps for the preparation of ethylhydroxyethylcellulose:

(a) provision of preferably washed and bleached pulp;
(b) optionally beating the pulp;
(c) treatment with an alkaline agent, preferably sodium hydroxide (mercerisation);
(d) treatment with ethylenoxide (C$_2$H$_4$O) (first alkylation step);
(e) treatment with CH$_3$CH$_2$Cl (second alkylation step);
(f) optionally washing and/or drying; and
(g) obtaining obtaining EHEC.

Preferably, the steps may be conducted in alphabetical order (a)-(g) and each step is performed on the intermediate product obtained from the preceding step.

Preferably, the EHEC obtained by sub-steps (a)-(g) of step 3) of the inventive method described above may be characterized by General Formula (5) below:

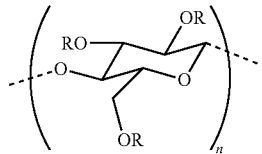

R = H or CH$_2$CH$_3$ or CH$_2$CH$_2$OH (5)

Cellulose acetate (CA) is used in lacquers, fibres, photographic films and fabrics. CA also finds application as a frame material for eyeglasses, and in cigarette filters.

CA may generally be obtained by reacting the pulp with acetic acid and acetic anhydride in the presence of sulfuric acid, followed by a controlled, partial hydrolysis to remove the sulphate and a sufficient number of acetate groups to give the product the desired properties. The anhydroglucose unit is the fundamental repeating structure of cellulose and has three hydroxyl groups which can react to form acetate esters. The most common form of cellulose acetate fibre is cellulose diacetate with an acetate group on approximately two of every three hydroxyl groups. This cellulose diacetate is known as secondary acetate, or simply as "acetate".

After it is formed, cellulose acetate may be dissolved in acetone into a viscous resin for extrusion through spinnerets to produce cellulose acetate filaments. As the filaments emerge, the solvent may be evaporated via dry spinning, producing fine cellulose acetate fibres.

Accordingly, step 3) of the inventive method may include the following sub-steps for the preparation of cellulose acetate:

(a) provision of preferably washed and bleached pulp;
(b) optionally beating the pulp;
(c) treatment with glacial acetic acid and acetic anhydride in the presence of a suitable catalyst such as sulfuric acid;
(d) treatment with aqueous solution of acetic acid (CH$_3$COOH) for (partial) hydrolysis; and
(e) obtaining cellulose acetate; and optionally
(f) extruding cellulose acetate through spinnerette and dry spinning to obtain cellulose acetate fibres.

Preferably, the steps may be conducted in alphabetical order (a)-(g) and each step is performed on the intermediate product obtained from the preceding step.

Preferably, the CA obtained by sub-steps (a)-(g) of step 3) of the inventive method described above may be characterized by General Formula (6) below:

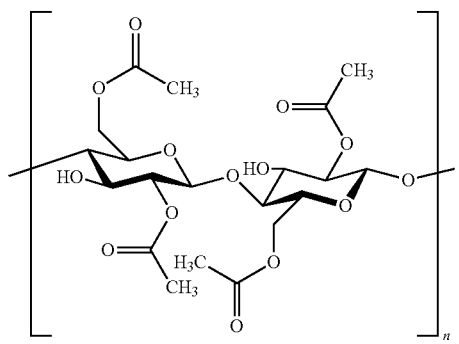

(6)

Cellulose nitrate is inter alia used to prepare plastics, lacquers, adhesives and explosives.

Cellulose nitrate may generally be obtained by treating the pulp with a mixture of nitric acid and sulfuric acid. The crude produce is preferably washed with water and subsequently treated with boiling sodium carbonate solution in order to adjust the degree of polymerization ("stabilization"). Finally, a beating and/or dewatering step is conducted to prepare the final product.

Accordingly, step 3) of the inventive method may include the following sub-steps for the preparation of cellulose nitrate:

(a) provision of preferably washed and bleached pulp;
(b) optionally beating the pulp;
(c) treatment with nitric acid and sulfuric acid (HNO$_3$+ H$_2$SO$_4$);
(d) washing, preferably with water;
(e) treatment with boiling sodium carbonate (Na$_2$CO$_3$) for stabilization; and
(f) optionally beating, washing and dewatering; and
(g) obtaining cellulose nitrate.

Preferably, the steps may be conducted in alphabetical order (a)-(g) and each step is performed on the intermediate product obtained from the preceding step.

Preferably, the cellulose nitrate obtained by sub-steps (a)-(g) of step 3) of the inventive method described above may be characterized by General Formula (7) below:

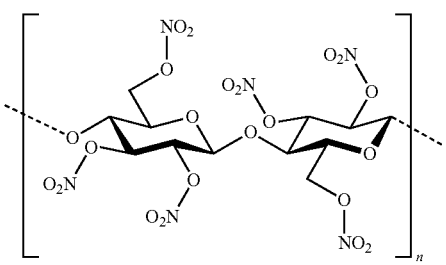

(7)

Manufacturing of Paper and/or Paperboard Products

Alternatively or additionally (if in step 3) the pulp is separated into several cellulose-derived process streams), optionally after washing and/or bleaching, the pulp can be used to prepare paper and/or paperboard products.

The manufacture of paper and/or paperboard products may typically include the following general steps. In a first step, the paper stock is prepared by pulp beating. Mechanical squeezing and pounding of cellulose fibre preferably permits water to penetrate its structure, causing swelling of the fibre and making it flexible. Mechanical action, furthermore, separates and frays the fibrils, submicroscopic units in the fibre structure. Beating further preferably reduces the rate of drainage from and through a mat of fibres, producing dense paper of high tensile strength, low porosity, stiffness, and rattle.

To that end, pulp is put into a beater, e.g. a Hollander beater consisting of an oval tank containing a heavy roll that revolves against a bedplate. Pulp is put into the beater, and water is added to facilitate circulation of the pulp mass. As the beating proceeds, the revolving roll is gradually lowered until it is riding full weight on the fibres between it and the bedplate. This action splits and mashes the fibres, creating hairlike fibrils and causing them to absorb. The beaten fibres will then drain more slowly on the paper machine wire and bond together more readily as more water is removed and the wet web pressed. Much of the beating action results from the rubbing of fibre on fibre. Long fibres will be cut to some extent.

During the beating step, other materials such as sizing, fillers, and dyes may be added and mixed with the fibres. By mounting a perforated cylinder that can rotate partially immersed in the beater stock, water may be continuously removed from the beater, and the stock therefore can be washed.

In large production modern mills, beaters were replaced by various types of continuous refiners, such as Jordan refiners. Like the beater, the Jordan refiner has blades or bars, mounted on a rotating element, that work in conjunction with stationary blades to treat the fibres. The axially oriented blades are mounted on a conically shaped rotor that is surrounded by a stationary bladed element (stator).

Like other refiners, the disk refiner consists of a rotating bladed element that moves in conjunction with a stationary bladed element. The disk refiner's plane of action, however, is perpendicular to the axis of rotation, simplifying manufacture of the treating elements and replacement. Since the disk refiner provides a large number of working edges to act upon the fibre, the load per fibre is reduced and fibre brushing, rather than fibre cutting, may be emphasized.

In mills that receive baled pulp and use refiners, the pulp is typically defibred in pulpers. While there are a number of variations in basic design, a pulper consists essentially of a large, open vessel, with one or more bladed, rotating elements that circulate a pulp-water mixture and defibre or separate fibres. The blades transform the pulp or wastepaper into a smooth mixture. Unlike beaters and refiners, pulpers do not reduce freeness and cause fibrillation in the fibres.

Manufacturing of paper and/or paperboard products may involve the addition of additives to the paperstock. Additives envisaged in the context of the present invention include sizing solutions, (coloured) pigments, fillers, dyes, strengthening and coupling agents, which are discussed in detail below.

Sizing solutions are preferably used to prevent aqueous solutions, such as ink, from soaking into the paper and/or paperboard product. A typical sizing solution consists of a rosin soap dispersion mixed with the stock in an amount of 1 to 5 percent of fibre. Further, sizing solutions preferably comprise suitable coupling agents, e.g. alum (aluminum sulfate) to allow the rosin dispersion to attach firmly to the fibre surface.

Paper intended for writing or printing usually contains white pigments or fillers to increase brightness, opacity, and surface smoothness, and to improve ink receptivity.

Suitable pigments include clay (aluminum silicate), often referred to as kaolin or china clay, titanium dioxide ($TiO_2$) and calcium carbonate ($CaCO_3$), which is also used as a filler to impart improved brightness, opacity, and ink receptivity to printing and magazine stocks.

Other suitable fillers are zinc oxide, zinc sulfide, hydrated silica, calcium sulfate, hydrated alumina, talc, barium sulfate, and asbestos. Since most fillers do not readily bind to fibres, coupling agents such as alum are typically used in combination therewith. The amount of filler used may vary from 1 to 10 percent of the fibre.

Soluble dyes or coloured pigments may be added to impart colour to paper. Many so-called direct dyes with a natural affinity for cellulose fibre are highly absorbed, even from dilute water solution. The so-called basic dyes have a high affinity for groundwood and unbleached pulps.

Strengthening agents are added to paper stock to enhance or to modify the bonding and coherence between fibres. To increase the dry strength of paper, the materials most commonly used are starch, polyacrylamide resins, and natural gums such as locust bean gum and guar gum. The most common type of starch currently used is the modified type known as cationic starch. When dispersed in water, this starch assumes a positive surface charge and thus preferably readily binds to negatively charged fibre surface.

Paper machines may employ interrelated mechanisms operating in unison to receive paper stock from the beater, form it into a sheet of the desired weight by filtration, press and consolidate the sheet with removal of excess water, dry the remaining water by evaporation, and wind the traveling sheet into reels of paper.

Traditionally, paper machines have been divided into two main types: cylinder machines and Fourdrinier machines. The former consists of one or more screen-covered cylinders, each rotating in a vat of dilute paper stock. Filtration occurs by flow action from the vat into the cylinder, with the filtrate being continuously removed. In the Fourdrinier machine a horizontal wire-screen belt filters the stock. In recent years a number of paper machines have been designed that depart greatly from traditional design. These machines are collectively referred to as "formers." Some of these formers retain the traveling screen belt but form the sheet largely on a suction roll. Others eliminate the screen belt and use a suction cylinder roll only. Still others use two screen belts with the stock sandwiched between, with drainage on both sides.

The paper or paperboard product produced by the paper machine may undergo a number of operations referred to as converting or finishing. There are two distinct types of paper conversion. One is referred to as wet converting, in which paper in roll form is coated, impregnated, and laminated with various applied materials to improve properties for special purposes. The second is referred to as dry converting, in which paper in roll form is converted into such items as bags, envelopes, boxes, small rolls, and packs of sheets.

Coatings may be applied to paper or paperboard products to achieve uniformity of surface for printing inks, lacquers, and the like; to obtain printed images without blemishes visible to the eye; to enhance opacity, smoothness, and gloss of paper or paperboard; and to achieve economy in the weight and composition of base paper stock by the upgrading effect of coating. For coating, a water dispersion containing pigment, which may be clay, titanium dioxide, calcium carbonate, satin white, or combinations of these, dispersants to give uniformity to the mixture or the "slip"; and an adhesive binder such as starch or latex, to give coherence to the finished coating may be applied to the paper.

Accordingly, step 3) of the inventive method may include the following steps for manufacturing a paper and/or paperboard product:

(a) provision of preferably washed and bleached suspended pulp;

(b) separating the cellulose fibres by beating or refining ("paper stock");

(c) optionally adding additives to the paper stock, preferably selected from sizing solutions, (coloured) pigments, fillers, dyes, strengthening and coupling agents;

(e) filtering the paper stock to preferably form a matted sheet of fibre;

(f) pressing and/or drying the wet sheet;

(g) optionally further converting, compressing, rolling, coating, impregnating and/or cutting the dry sheet; and (h) obtaining a paper or paperboard product.

Preferably, the steps may be conducted in alphabetical order (a)-(g) and each step is performed on the intermediate product obtained from the preceding step.

The differences among various grades and types of paper are typically determined by: (1) the type of fibre or pulp, (2) the degree of beating or refining of the paper stock, (3) the addition of various materials to the stock, (4) formation conditions of the sheet, including basis weight, or substance per unit area, and (5) the physical or chemical treatment applied to the paper after its formation.

Step (4): Isolation and/or Purification of Modified Lignin-Derived Components

In step 4) of the inventive method, the lignin-derived process stream(s) are subjected to an isolation and/or purification step, to obtain at least one process stream(s) of modified lignin-derived components.

As used herein, the term "isolation" refers to the controlled removal of desired compounds from a composition or crude mixture, preferably also encompasses purification of said desired compounds by removing undesired components such as by-products, catalysts, impurities and the like, thereby further preferably concentrating the desired compounds.

The present invention envisages at least the provision of one lignin-derived process stream A for the production of low molecular weight aromatic lignin-derived compounds, preferably sulfonated low molecular weight aromatic lignin-derived quinone compounds (preferably in parallel to the product(s) obtained from the cellulose-derived process stream(s)). All intermediates and products obtained from said lignin-derived process stream are may also be labelled with the letter "A", to indicate their origin from that particular process stream.

As a derivative of natural lignin, the "modified lignin-derived component" is a lignin molecule, which underwent a pulping process, such as "Kraft lignin" or "lignosulfonate". A "modified lignin-derived component" typically has a lower molecular weight than natural lignin, from which it is derived. However, the "modified lignin-derived component" is larger than the low molecular weight lignin-derived compound, preferably having a molecular weight of at least 1.000 Da. The nature (and the actual molecular weight) of the "modified lignin-derived component" may vary largely depending, e.g., on the starting material, on the (pulping) method, by which the modified lignin-derived component is obtained, and on the reaction conditions applied by the inventive method. However, it is common to the modified lignin-derived components that they are composed of $C_8$ or $C_9$ building blocks after, e.g., a pulping process, as they occur in natural lignin.

It follows from natural lignin's complex and somewhat random chemical structure that lignin-derived components, such as products of the pulping process, are typically heterogeneous. The pulping process provides a larger variety of lignin-derived components, which may typically contain from 8 to 150 building blocks. Moreover, lignin-derived components of the same number of building blocks are also diverse in terms of their chemical nature, as they reflect individual portions of the heterogeneous natural lignin polymer. That chemical and structural heterogeneity of lignin-derived material obtained from e.g. the pulping process traditionally impeded the preparation of homogeneous and/or high quality products by prior art methods, such that adequate economic exploitation of lignin-derived material was difficult to achieve in the art. That prior art issue is overcome by the inventive method.

Pulping processes, nevertheless, typically yield "modified" lignin-derived components based on $C_8$ or $C_9$ building blocks, wherein some or all of the building blocks may be modified. Modifications preferably occur at the linking groups of those building blocks of natural lignin, which are dissociated by the pulping process, and/or at substitution sites of the building blocks, in particular at the aromatic ring system of a building block, e.g. by side chain modification or e.g. by sulfonation. Accordingly, the molecular weight of the modified building blocks of lignin-derived components may typically be slightly higher than the molecular weight of the building blocks of the natural lignin polymer.

Typically, "modified lignin-derived components" as used herein are present as a fraction of a (process) "stream". Such a stream may comprise residual or waste material and the solvent and/or dispersant from which the intermediate of interest is preferably isolated. Typically, the solvent and/or dispersant accounts for at least 50% (w/w) of the total weight of material forwarded as a "stream" to the next method step, or at least 60% (w/w), preferably for at least 70% (w/w), or at least 80% (w/w). The solvent and/or dispersant is typically an aqueous medium, but may alternatively be an organic solvent, depending on the pulping process. Generally, the stream flows unidirectionally, from the preceding method step to the more downstream method steps. Valves, pumps and/or gravity-assisted means may typically be employed to facilitate the required flow of the stream downwards to the final step of the method of the present invention.

Typically, pulping breaks the lignin in the lignocellulosic material into smaller molecules (in particular modified lignin-derived components), which are more soluble in the pulping liquor. Pulping thus typically yields a lignin-derived process stream typically comprising modified lignin-derived components and occasionally lignin, dissolved or dispersed in the pulping liquor, as well as by-products, impurities, catalysts and residual amounts of cellulose and hemicellulose. In particular, pulping may degrade (and thereby optionally solubilize) cellulose, at least to a minor degree, but individual cellulose fibres may also detach from the chopped lignocellulosic material during the pulping process and be present in the pulping liquor in dissolved or dispersed form. These cellulose fibres may be present as fibre scaffolds, or individually.

After the pulping process in step 2) of the inventive method, at least one or more (partial) lignin-derived process stream(s) may be provided. It is thus envisaged that in step 4) of the inventive method, modified lignin derived components may be isolated and/or purified from one or from several or from each of the (partial) lignin-derived process stream(s) (B, C, D . . . ) emerging from the pulping process. The provision of several partial lignin-derived process stream(s) in step 2) of the inventive method preferably adds flexibility to the control of the yield envisaged for the fractions comprised in the lignin-derived process stream(s). Modified lignin-derived components are thus either isolated from the single process stream, or from at least one of the partial lignin-derived process streams obtained from pulping in step 2) of the inventive method.

The isolation of modified lignin-derived components as described herein may be applied to one or more of the (partial) lignin-derived process stream(s) A (B, C, D . . . ) obtained by the pulping process in step 2) of the inventive method. In other words, isolation and/or purification of modified lignin-derived components as described below may be accomplished from a single lignin-derived process stream or from one of several (partial) lignin-derived process streams, which may preferably be provided after pulping in step 2) of the inventive method by separating (or dividing) the resulting lignin-derived process stream into two or more (partial) process streams. This allows to control the amount of the modified lignin-derived components further processed according to the inventive method. Hence, stream separation is a tool to fine tune the inventive method when determining its flow rate and turnover of the process. By dividing the lignin-derived process stream into two or more partial lignin-derived process streams, the supply of modified lignin-derived components according to downstream process step (5) may be controlled as well.

Modified lignin-derived components present in either a single lignin-derived process stream or in two or more (partial) lignin-derived process streams obtained from pulping in step 2) of the inventive method are preferably isolated from said process stream(s) as described below.

Isolation and/or purification may be controlled by the applied parameters and means, e.g. the amount of precipitation agent, pH, extraction or filtration characteristics. Isolation may be applied to all or part of the partial process streams (if present). Typically, the lignin-derived process stream(s) obtained by pulping in step 2) of the inventive method may be divided into two partial lignin-derived process stream(s), with one of them being subjected to isolation of modified lignin-derived components and further processing to preferably provide low molecular weight aromatic lignin-derived compounds as described herein, and the other partial lignin-derived process stream(s) being used for combustion and/or to prepare other target compounds.

Isolation and/or purification of the modified lignin-derived components may be accomplished by any appropriate means typically employed in the field of solid-fluid or fluid-fluid separation. The isolation may, for example, involve filtration, extraction, counter current flow separation and precipitation.

It may be preferred to isolate modified lignin-derived components as dry matter from the solvent and/or dispersant of the process stream, and subsequently dissolve or disperse said components in a suitable solvent or dispersant, e.g. an aqueous solvent or dispersant, before further processing in the subsequent method step. Alternatively, modified lignin-derived components may be enriched, e.g. by reducing the solvent and/or dispersant content of the modified lignin-derived components, such that a concentrated solution or dispersion of modified lignin-derived components is provided.

Isolation and/or purification of modified lignin-derived components in step 4) of the inventive method may preferably be achieved by filtration, such as ultra- and/or nano-filtration, extraction, countercurrent flow, stripping, ion-exchange, precipitation by di- or multivalent cations, such as calcium cations (which may e.g. be provided as calcium hydroxide), precipitation by $CO_2$ in acidic solution, or any combination of thereof.

(a) Filtration

Preferably, isolation in step 4) of the inventive method is carried out by any type of extraction or filtration, preferably ultrafiltration and/or nanofiltration.

"Filtration" is hereby understood as a physical purification or enrichment method involving membrane technology by permeable membranes. Membranes are characterized by their nominal pore size. It typically describes the maximum pore size distribution. As that parameter provides only vague information about the retention capacity of the membrane, the "cut-off" is typically used as the parameter to characterize separation properties of membrane-associated filtration. The exclusion limit or "cut-off" of the membrane is usually specified in the form of NMWC (nominal molecular weight cut-off, or MWCO, molecular weight cut off, with units in Dalton). It is commonly defined as the minimum molecular weight of a globular molecule that is retained to 90% by the membrane. In practice, the MWCO of the membrane should be at least 20% lower than the molecular weight of the molecule that is to be separated. For example, a 1 kDa filter is suitable to let pass a small molecule with a molecular weight of, e.g., 500 Da, while the larger modified lignin-derived components of a molecular weight of, e.g., 2.000 Da are not able to pass.

Preferably, filtration is used herein to isolate, the dispersed or suspended modified lignin-derived components obtained from the pulping process in step 2) of the inventive method. The filter cut-off is set in such a way, that it is suitable to discriminate the molecular weight of the target modified lignin-derived components and of other components in the process stream. The other components may be larger (e.g. residual natural lignin and/or fragments thereof having a higher molecular weight than the modified lignin-derived components) or smaller (e.g. reactive agents of the pulping process, hydrolyzed hemicellulose) than the target components. If the target modified lignin-derived components are of a larger molecular weight than all other components in the process stream, the filter is selected to have a cut off such that the target components are typically retained in the filter. Otherwise, if other components are larger—in terms of molecular weight—than the modified lignin-derived components, the cut-off may typically be selected such that the target components may typically be found in the filtrate.

Typically, the filtration in isolation step 4) of the inventive method may be a combination of (different) filtration steps. Therein, for example, in one step the cut off of the filter is selected to be higher than the molecular weight of the modified lignin-derived components. Accordingly, other components with a higher molecular weight are kept in the filter and the modified-lignin-derived components remain in the filtrate, i.e. in the residual process stream. In another step, the residual process stream may be subjected to a second filtration, wherein the cut-off is selected to be lower than the molecular weight of the modified lignin-derived components. Accordingly, the target modified lignin-derived components are retained in the filter and, thereby, isolated from the residual process stream. Thereby, the target components may be obtained as dry matter and may subsequently be dissolved for further processing.

The more the different fractions within the process stream (s) differ in terms of their molecular weight, the more effective may the isolation by filtration be carried out. For example, as the Kraft process typically yields modified lignin-derived components (Kraft lignin) of lower molecular weight than the sulphite process, filtration may be very preferred to separate Kraft lignin from lignin-derived material of higher molecular weight, such as non-modified or re-polymerized lignin-derived material or other debris.

Ultrafiltration and/or (depending on the size of the lignin-derived components to be isolated) nanofiltration may be preferably employed in step 4). Ultrafiltration typically employs a pore size of 2-100 nm and a molecular weight cut-off value of about 5 kDa. Nanofiltration typically refers to a filtration mode based on a pore size of 1-2 nm and a molecular weight cut-off value of 0.1-5 kDa. Accordingly, ultrafiltration is typically employed to separate or isolate larger lignin-derived components (e.g. larger than 5.000 Da, larger than 8.000 Da or larger than 10.000 Da) from the process stream (containing components of whatever e.g. the lignin-derived fraction or residual cellulosic fraction or the hemicellulosic fraction of a molecular weight of less than 5.000 Da). That isolated larger molecular weight fraction may be subject to further separation in order to separate larger isolated components of distinct fractions, e.g. to isolate the lignin-derived components from residual cellulosic degradation products or hemicellulosic components.

Also, the remaining components of the lignin-derived fraction in the process stream having a molecular weight lower than the cut-off level chosen for initial ultrafiltration may be isolated from other components in the process stream. E.g. the (partial) process stream may be subjected to another filtration step with a lower cut-off level than chosen for the initial ultrafiltration step, e.g. by additional lower cut-off level ultrafiltration and/or nanofiltration. Thereby, the lignin-derived components of a molecular weight lower than the cut-off-level of the first filtration step and larger than the cut-off level of the second filtration step may be isolated. That retained lignin-derived fraction may be subject to further isolation to separate the lignin-derived component fraction from components of similar size of other fractions (e.g. from hemicellulosic degradation products of similar size). Accordingly, the inventive method may be set up such that components of the lignin-derived fraction are isolated, which fall within the individually desired smaller molecular weight range of e.g. between 1.000, 2.000, 3.000, 4.000, 5.000 or 6.000 Da (cut-off level of the second filtration step) and 5.000, 6.000, 8.000 or 10.000 Da (cut-off level of the first filtration step). Thereby or by any other method known in the art to separate by molecular weight or by other physico-chemical parameters, a more homogeneous lignin-derived fraction may be forwarded to decomposition step (3).

Accordingly, two ultrafiltration steps or ultrafiltration and nanofiltration, respectively, may e.g. be combined to arrive at a modified lignin-derived fraction of a defined molecular weight range (e.g. 5.000 to 10.000 or 1.000 to 5.000 Da, respectively for Kraft lignin). Whenever isolation from the process stream of the sulphite process-derived lignosulfonate is concerned, such isolation may preferably be performed by employing suitable isolation methods, e.g. as described by Lebo et al. (Lebo, Stuart E. Jr.; Gargulak, Jerry D.; McNally, Timothy J. (2001). "Lignin". Kirk-Othmer Encyclopedia of Chemical Technology. Kirk Othmer Encyclopedia of Chemical Technology. John Wiley & Sons, Inc.), which is incorporated herein by reference. "Lignosulfonate" (due to the larger molecular weight of its components) will preferably be based on two ultrafiltration steps resulting e.g. in a molecular weight range of the isolated lignin-derived components of between 6.000 Da and 15.000 Da or 8.000 Da and 12.000 Da.

Ultra- and/or nanofiltration may typically employ membranes, which are preferably tubular membranes exposing solvent resistance, i.e. which are preferably resistant at high and low pH values. Ultra- and/or nanofiltration is typically performed at elevated pressure, preferably above 5 bar, more preferably above 10 bar, most preferably at a pressure of 10-15 bar. Further, the applied temperature for the filtration step is typically higher than room temperature (25° C.) to facilitate isolation of the fraction of modified lignin-derived components. Usually, the temperature is chosen such that degradation of the components to be isolated is essentially avoided. The temperature may be at least 40° C., preferably at least 50° C., most preferably about 60-65° C.

Hence, the preferred membrane's cut-off size of the employed ultra- or nanofiltration may depend on the expected molecular weight of the target modified lignin-derived components. For example, Kraft lignin being of a relatively small molecular weight may require a membrane cut-off of about 2 to kDa or from 2 to 8 kDa, while larger lignosulfonate may require a membrane cut-off of about 5 to 50 kDa or even up to 100 kDa. Typically, the cut-off size for membranes to isolate lignosulfonate may be about 1 to 20 kDa.

If ultra- and/or nanofiltration is applied, it may preferably be preceded by a pre-filtration step to separate larger debris, e.g. insoluble or poorly soluble polymers and/or fragments thereof. Thereby, efficiency may be increased as excessive blockade of the ultra- and/or nanofiltration membrane may be avoided, when isolating the fraction of modified lignin-derived components. Accordingly, the pre-filter typically has a larger pore size and/or molecular weight cut-off than the ultra- and/or nanofiltration membrane.

Whether filtration is applied or not may depend on whether the modified lignin-derived components are dissolved in the fluid phase or suspended as solid components. Filtration is preferably used for separation of suspended or dispersed solid, i.e. preferably dispersed particles of a size of about >1 μm. By filtration, oversize solid particles are typically retained by the membrane with the yield depending on the character of the modified lignin components, their particle size and the filter's cut off.

Preferably, isolation and/or purification step 4) of the inventive method thus comprises filtration and/or extraction, preferably ultrafiltration and/or nanofiltration by an ultrafiltration and/or nanofiltration cell, preferably having a prefiltration section. Filtration may preferably be carried out in a ultrafiltration and/or nanofiltration cell comprising at least one molecular weight cut-off unit, preferably at least two molecular weight cut-off units, wherein the at least one molecular weight cut-off unit has a cut-off level preferably of 0.5 kDa to 2 kDa.

(b) Extraction

Alternatively, isolation and/or purification step 4) may encompass extraction e.g. by means of an organic solvent. As used herein, "extraction" is typically a separation process comprising the separation of a desired substance from its environment. It may include liquid-liquid extraction and/or solid phase extraction. Extraction may use two immiscible phases to separate dissolved modified lignin-derived components from the original phase into another. By extraction, organic compounds are extracted by an organic solvent from the aqueous phase. Common solvents for extraction are classified by their polarity from ethyl acetate (lowest polarity) to water (highest polarity): ethyl acetate<acetone<ethanol<methanol<acetone:water (7:3) <ethanol:water (8:2)<methanol:water (8:2)<water, in the order of the Hildebrand solubility parameter. The solution containing the extracted fraction (i.e. the components) may be dried, e.g. by using a centrifugal evaporator or a freeze-drier.

For example, Kraft lignin may be extracted by step 4) from the process stream, if less soluble in an aqueous medium than in appropriate organic solvents (such as methanol, ethanol, acetone and aqueous mixtures thereof known in the art).

Alternative extraction techniques may include supercritical carbon dioxide extraction, ultrasonic extraction, heat reflux extraction, microwave-assisted extraction, instant controlled pressure drop extraction (DIC), and perstraction. Amongst them, perstraction may be preferred. Typically, "perstraction" includes two liquid phases, with only one phase including a solvent for extraction. Perstraction may advantageously be more gentle, faster and cheaper than traditional biphasic extraction techniques. "Stripping" may be employed as another gentle extraction alternative, which allows the fraction of modified lignin-derived components may be isolated from the process stream. "Stripping" is generally a physical separation process, wherein one or more components are removed from a liquid stream by a vapor stream. In industrial applications, the liquid and vapor streams may be employed co-currently or flow countercurrent. Stripping is usually carried out in either a packed or trayed column.

(c) Countercurrent Exchange

Isolation and/or purification of modified lignin-derived components in step 4) of the inventive method may also be achieved by countercurrent flow, with the flow forwarded in opposite directions. For the inventive method the concentration of dissolved modified lignin-derived components along the concentration gradient may be envisaged. The counter-current exchange method may maintain the gradient of the two flows essentially stable for the entire contact zone. Hence, countercurrent flow is particularly suitable to isolate dissolved modified lignin-derived components and may be less preferred for dispersed modified lignin-derived components.

(d) Precipitation

Isolation and/or purification of modified lignin-derived components in step 4) of the inventive method may also be achieved by precipitation. Precipitation preferably allows a solid fraction to be isolated from solution. Precipitation may also be employed to control the amount of precipitated modified lignin (within a given time window) by the choice of the added amount of precipitation agent and/or the pH. Preferably, precipitation may be conducted by means of the addition of a cation, preferably a di- or multivalent cation, most preferably of calcium.

Precipitation may be in particular preferred for lignosulfonate or, equivalently, for sulfonated Kraft lignin. Precipitation by pH is less preferred, e.g. for lignosulfonate, as it is generally soluble in water over the entire pH range and may not be readily isolated by pH modification. However, precipitation by calcium salt addition may be preferred. E.g., excess lime (i.e. a calcium-containing inorganic material, in which carbonates, oxides and hydroxides typically predominate) may be added to the process stream, such that calcium lignosulfonate may precipitate. This process is generally known as Howard process. It is the most straight-forward recovery method known. Typically, up to 95% of the stream's lignosulfonate may be isolated by precipitation. Modified lignin resulting from the Kraft process ("Kraft lignin") may be sulfonated in step (1) and thereafter subjected to, e.g., lime precipitation.

The remainder of modified lignin-derived components, which are not further employed by the present invention, may be channeled to the paper manufacturing process or may serve for other applications such as energy provision, or may be stored for later use or may be discarded.

Step (5) Chemical Decomposition

In step 5) of the inventive method, the process stream of modified lignin-derived components A obtained from isolation step 4) is subjected to chemical decomposition. Process stream A may be treated in a variety of ways in step 5), depending e.g. on the chosen pulping method and characteristics of the obtained modified lignin-derived components A, as well as the nature desired target compounds A. Process stream A is particularly envisaged for providing low molecular weight aromatic lignin-derived compounds A, preferably sulfonated low molecular weight aromatic lignin-derived quinone compounds A characterized by any one of General Formulas (1), (2) or (3), and the type and parameters of chemical decomposition may preferably be chosen accordingly to steer the processing of process stream A into the desired direction.

As discussed above, further lignin-derived process streams B, C, D . . . may be separated from the main process stream A. These further process stream(s) may (in part) be subjected to the same method step(s), for instance the same chemical decomposition step(s) 5), as the main process stream A. However, it will be understood that processing of the further lignin-derived process streams B, C, D . . . may typically diverge from the processing of the main process stream A at some point to obtain different valuable products therefrom.

"Chemical decomposition" is typically understood as the provision of a plurality of lower molecular weight compounds by chemical and/or physical degradation of higher molecular weight starting material. Typically, such a reaction yields compounds comprising fragments or moieties of the higher molecular weight starting material. Chemical decomposition may be studied by chemical analysis, e.g. by mass spectrometry, gravimetric analysis, and thermogravimetric analysis. Preferably, decomposition according to the inventive method is carried out by catalytic reaction, or alternatively, electrolytically. Thermal decomposition may be employed as well according to the invention, but is less preferred, as it usually yields an even broader spectrum of diverse low molecular weight lignin-derived compounds. A larger fraction of these compounds following decomposition is of aromatic nature reflecting aromatic ring systems of the building blocks of the natural lignin polymer provided in step (1).

Decomposition may result in a heterogeneous ensemble of lignin-derived products comprising (modified) lignin-derived building blocks, i.e. "monomers" or "dimers", preferably biphenylic dimers. Preferably, the resulting modified lignin-derived products herein essentially consist of monomers and dimers, i.e. the resulting lignin-derived products of step (2) do preferably not comprise larger (oligomeric) modified lignin-derived fragments but only modified lignin-derived monomers and dimers. Higher molecular weight modified lignin-derived components converted by chemical decomposition, preferably chemically modified lignin polymers (such as lignosulfonate and Kraft lignin), decompose in a controllable manner at elevated temperatures, preferably below the pyrolytic temperature of, e.g. 1000° C., such as at least 300° C., preferably at least 400° C., more preferably 400 to 500° C. and in the presence of a suitable catalyst (e.g. in a oxidative cracking/reductive cracking reaction) and/or when subjected to electro-oxidation.

In the context of the present invention, chemical decomposition reactions may be referred to as "cracking" reactions. In general, "cracking" means any type of molecular dissociation under the influence of, e.g., heat, catalysts, electric currents and/or solvents. Preferably, "cracking" refers to catalyzed reactions of breaking or dissociating larger molecules into their smaller fragments by dissociation of covalent bonds of the larger molecule. Cracking includes the (preferably catalyzed) decomposition reactions occurring via oxidation ("oxidative cracking") or reduction ("reductive cracking") of target molecules.

Cracking kinetics and reaction products typically depend on the reaction temperature and/or the catalysts used. In addition, the ensemble of products resulting from cracking is dependent on the nature of the lignin-derived compounds used as starting material for the decomposition reaction. Accordingly, modified lignin-derived components, e.g. Kraft lignin or lignosulfonate, may be subjected to a catalytic reaction at a temperature significantly lower than pyrolytic temperature or to electric current, preferably by electro-oxidation.

Generally, cracking makes use of a reactor and a regenerator for regenerating the catalytic material. For instance, modified lignin-derived components as starting material for the chemical decomposition reaction may be injected onto preferably hot, fluidized catalysts. The resulting vapor-phase products may be separated from the catalytic materials and fractionated into various product or product fragment fractions by condensation. The catalyst may typically be introduced into a regenerator, wherein air or oxygen is preferably used to separate any residual components by an oxidation reaction, such that the surface of the catalyst is freed from any by-products, which are formed as a result of the cracking process. The hot regenerated catalyst may then be recycled to the reactor to complete its cycle. Originally, cracking was developed for petrochemistry to disrupt larger e.g. gasoil molecules into smaller gasoline molecules and olefins. Advantageously, analogous cracking reactions may be applied to modified lignin-derived components in step 5) of the inventive method.

Preferably, modified lignin-derived components A are processed according to the present invention to ultimately yield derivatized, preferably sulfonated, low molecular weight aromatic lignin-derived quinone compounds A as target compounds.

In step 5) of the inventive method, modified lignin-derived components are subjected to chemical decomposition, which may be carried out by (a) oxidative cracking; (b) reductive cracking; or (c) electro-oxidation. As discussed above, chemical decomposition is preferably used to disrupt larger, polymeric lignin-derived components, thereby converting high(er) molecular weight modified lignin-derived components to low(er) molecular weight lignin-derived compounds.

"Oxidative cracking" preferably refers to chemical decomposition reactions wherein the "cracked" components lose electrons, e.g. by the introduction of electronegative functional groups such as OH-groups and/or by replacing less electronegative functional groups (e.g. OH) with more electronegative functional groups (e.g. oxo, =O).

"Oxidative cracking" in step 5) of the inventive method preferably involves the treatment of modified lignin-derived components with an oxidizing agent, preferably in the presence of a suitable catalyst.

"Reductive cracking" preferably refers to chemical decomposition reactions wherein the "cracked" components gain electrons.

"Reductive cracking" in step 5) of the inventive method preferably involves the treatment of modified lignin-derived components A with a reductive agent, i.e. an agent which "donates" electrons to another species, in the presence of a suitable catalyst.

Catalysts employed in oxidative or reductive cracking may be heterogenous (i.e. have the same phase as the reactant(s)) or homogenous (i.e. have a phase that is different from the phase of the reactant(s), e.g. being dissolved in the reaction solution), or a combination thereof.

The nature and process parameters of a chosen chemical decomposition reaction used in step 5) of the inventive method typically influences the type and nature of compounds obtainable from that step. As discussed elsewhere herein, the present invention envisages the processing of at least one process stream of modified lignin-derived components A, which is preferably used to prepare derivatized, preferably sulfonated, low molecular weight lignin-derived quinone compounds A, more preferably characterized by General Formula (1), (2) or (3). However, further process streams of modified lignin-derived components B, C, D . . . may also be provided, and they may be treated in the same or different ways as process stream A in step 5) of the inventive method.

(a) Oxidative Cracking of Modified Lignin-Derived Components

Preferably, chemical decomposition of modified lignin-derived components A (and optionally B, C, D . . . ) in step 5) of the inventive method may be achieved by oxidative cracking.

Preferred oxidizing agents for oxidative cracking of modified lignin-derived components A (and optionally B, C, D . . . ) in step 5) of the present invention include air, $O_2$ or $H_2O_2$, preferably air.

Preferred catalysts for oxidative cracking of modified lignin-derived components A (and optionally B, C, D . . . ) in step 5) of the present invention may be heterogenous catalysts, e.g. wherein the modified lignin-derived components A (and optionally B, C, D . . . ) may be provided in dissolved form and the catalyst may be provided in solid form, or homogenous catalysts.

Preferred catalysts for oxidative cracking of modified lignin-derived components A (and optionally B, C, D . . . ) may comprise or consist of metal ions, preferably selected from Co(II), Cu(II), Fe(II) and Fe(III), more preferably Fe(III), or metalloid elements, or combinations thereof. Preferred "metalloid elements" include boron, silicon, germanium, arsenic, antimony, tellurium, aluminum, and selenium, or combinations thereof and may more preferably be selected from B(III), Si(IV) and/or Al(III), or combinations thereof. Metal ions or metalloid elements may be provided in the form of coordination complexes, oxides, or salts. A "coordination complex" means a compound or ion with a central usually metallic or metalloid atom or ion ("coordination center") combined by coordinate bonds with a definite number of surrounding ions, groups, or molecules ("ligands", "complexing agents").

Further catalysts for oxidative cracking of modified lignin-derived components A (and in particular B, C, D . . . ) in step 5) of the present invention may be selected, without limitation, from catalysts comprising or consisting of metals or metal oxides, the metals preferably being selected from, without limitation, platinum (Pt), nickel (Ni), iron (Fe), rhenium (Re), titanium (Ti), manganese (Mn), or combinations thereof, such as Cu—Ni—Ce or Cu—Mn. Alternatively, electrocatalysis may be applied, where modified lignin-derived components A are oxidized at the surface of an electrocatalyst (e.g. a Pt, Au, Cu, or Ni electrode) in a suitable solvent such as methanol. Further catalysts for oxidative cracking of modified lignin-derived components A include homogenous catalysts selected from, without limitation, metalloporphyrins such as TPP, TMP, TF5PP or TPPS complexing Fe, Co or Ru; Schiff-base catalysts such as Co(salen) (where Salen=[N,N'-bis(salicylidene)ethane-1,2-diaminato]); nonporphyrinic catalysts such as tetraamido macrocyclic ligand (TAML), manganese-1,4,7-trimethyl-1,4,7-triazacyclononane (TACN) and manganese 1,2-bis-(4,7-dimethyl-1,4,7-triazacyclonon-1-yl)ethane (DTNE); polyoxometalates (POMs); simple metal salts such as CuO, $CuSO_4$, $FeCl_3$ or combinations thereof; or others such as zeolites.

Accordingly, step 5) of the inventive method may preferably include oxidative cracking of modified lignin derived-components A, preferably in the presence of a heterogeneous or homogeneous catalyst or a combination of catalysts. Typically, oxidative cracking may be carried out in the presence of an oxidizing agent such as air, $O_2$ or $H_2O_2$, preferably air, and preferably a catalyst or a combination of preferably heterogenous catalysts.

For instance, oxidative cracking of lignin-derived components A may be accomplished using boron as a catalyst. Oxidative cracking may then involve a hydroboration-oxidation anti-Markovnikov reaction, which is preferably a two-step organic reaction.

Oxidative cracking may preferably be carried out under elevated temperature and/or pressure conditions. In particular, oxidative cracking may be carried out at a temperature of between about 30° C. to about 400° C., preferably of between about 100° C. to about 350° C. Preferably, the temperature is at least about 150° C., more preferably at least about 170° C. Preferably, the chosen temperature is below the pyrolytic temperature so as to involve pyrolytic reactions. Accordingly, reaction temperatures for oxidative cracking are preferably lower than 1000° C., more preferably lower than 800° C., even more preferably lower than 500° C.

Oxidative cracking may preferably be carried out in a single reaction vessel.

Some exemplary preferred oxidative cracking conditions and reactions are described below.

In some cases, oxidative cracking (for instance using $O_2$ as an oxidizing agent) may be performed in a fluidized bed reactor, particularly a reactor comprising a sand bed. Under such conditions, the temperature may be set to at least 250° C., preferably to at least 300° C. Thereby, the oxidation rate may advantageously be increased and the formation of undesired by-products may be reduced. The reaction may be carried out in solution under constant stirring, e.g. above 500, 600, 700, 800, 900 or 1.000 rpm.

In some cases, oxidative cracking may be accomplished using air as the oxidizing agent in combination with a suitable catalyst. To that end, the pH value of the process stream of modified lignin-derived components A is adjusted to an alkaline (e.g. pH=9) or acidic pH, as desired, and a metal and/or metalloid catalyst is added. The reaction solution may be heated to a temperature of at least 150° C., preferable to a temperature of 150 to 300° C., more preferably 160-170° C. The pressure may be at least 5 atm, preferably from 10 to 12 atm.

In some cases, oxidative cracking may be accomplished using oxygen as the oxidizing agent in combination with a suitable catalyst. To that end, oxidative cracking is conducted in an oxygen-enriched environment, more preferably under increased pressure, in particular increased oxygen partial pressure. The pH value of the process stream of modified lignin-derived components A is adjusted to an alkaline (e.g. pH=9) or acidic pH, as desired, and a metal and/or metalloid catalyst is added under oxygen-enriched reaction conditions. Under alkaline conditions, the oxygen partial pressure may be at least 3 bar $p(O_2)$, more preferably 4 to 5 bar $p(O_2)$. Under acidic conditions, the oxygen partial pressure may be at least 10 bar $p(O_2)$, sometimes at least 20 bar $p(O_2)$. An alcohol, e.g. methanol, may be added to the reaction to avoid re-polymerization of "cracked" lignin-derived components. The alcohol may be added in an amount of at least 5%, at least 10%, preferably at least 20%, more preferably at least 30%, most preferably at least 40% with respect to the total reaction volume.

In accordance with the above, in step 5) of the inventive method, modified lignin-derived components A (and optionally B, C, D . . . ) may be subjected to oxidative cracking for chemical decomposition. Oxidative cracking may preferably be carried out in the presence of an oxidizing agent, preferably air, and a catalyst comprising or consisting of (a) a metal ion selected from Co(II), Cu(II) and Fe(III); or (b) a metalloid component selected from B(III), Si(IV) and Al(III); preferably at a temperature of 30-400° C., more preferably 100-350° C.

(b) Reductive Cracking of Modified Lignin-Derived Components

Alternatively, chemical decomposition of modified lignin-derived components A in step 5) of the inventive method may be achieved by reductive cracking.

Preferred reducing agents for reductive cracking include hydrogen or an alcohol as H-donor.

Suitable catalysts are preferably bifunctional, combining a support active in cracking, which may typically consist of zeolites or amorphous silica-alumina with various compositions, with a (noble) metal such as nickel, platinum, palladium, ruthenium, rhenium, gold, cobalt or tungsten for the hydrogenation reaction. Particularly, suitable catalysts may be selected, without limitation, from H-ZSM-5; H-Y; silicalite; silica; $Pt/Al_2O_3$—$SiO_2$; sulfided Ni—W/$SiO_2$—

Al$_2$O$_3$, Ni—Mo/SiO$_2$—Al$_2$O$_3$; optionally sulfided Co—Mo/Al$_2$O$_3$; supported or non-supported Pt-modified superacid catalysts, such as Pt/SO$_4^{2-}$/ZrO$_2$, Pt/WO$_4^{2-}$/ZrO$_2$, or Pt/SO$_4^{2-}$/TiO$_2$.

In the inventive method, modified lignin-derived components A are typically provided in solution and the catalyst is usually provided as a heterogenous catalyst in solid form. The catalyst may preferably provided on the surface of a support material preferably selected from the group consisting of active carbon, silica, titaniumoxide and/or aluminumoxide. Thereby, the lignin-derived components may be subject to e.g. hydrogen-based "lysis" by cleavage of carbon-carbon or carbon-heteroatom single bonds (hydrogenolysis).

Some exemplary preferred reductive cracking conditions and reactions are described below.

In some cases, reductive cracking of modified lignin-derived components A may be carried out by means of a catalyst comprising nickel, e.g. supported on activated carbon (Ni/C). The reaction may involve a fragmentation-hydrogenolysis process of modified lignin-derived components A into lower molecular weight compounds, e.g. di- or monomeric phenolic target compounds, in alcoholic solvents over nickel-based catalysts may be performed. The alcohol typically acts as the source of active hydrogen as the reducing agent.

In some cases, reductive cracking of modified lignin-derived components A may be accomplished in the presence of Ruthenium deposited on a carbon catalyst (Ru/C) in an organic solvent, such as methanol, under a reducing atmosphere, e.g. H$_2$ atmosphere, preferably at elevated temperatures. Such a reaction may preferably yield phenol-rich lignin oil comprising more than 50% (w/w) of phenolic monomers and 10% to 25%, preferably less than 20% (w/w) phenolic dimers. The phenolic monomers typically comprise syringol, in particular 4-n-propylsyringol, 4-ethylphenol, and guaiacol, in particular 4-ethylguaiacol and 4-n-propylguaiacol.

In some cases, lignocellulosic material may be delignified through simultaneous solvolysis and catalytic hydrogenolysis of the lignin material in one single step. Combined solvolysis and catalytic hydrogenolysis may preferably be carried out in the presence of Ruthenium preferably deposited on a carbon catalyst (Ru/C), preferably in an organic solvent, such as methanol, under a reducing atmosphere, such as an H$_2$ atmosphere. The reaction is preferably carried out at elevated temperatures. The resulting product of combined solvolysis and catalytic hydrogenolysis may be further processed as described herein to obtain low molecular weight aromatic lignin-derived (mono- or dimeric) compounds.

In accordance with the above, in step 5) of the inventive method, modified lignin-derived components A may be subjected to reductive cracking for chemical decomposition. Reductive cracking may preferably be carried out in the presence of a reducing agent, preferably hydrogen or a hydrogen donor such as alcohol, and a catalyst comprising or consisting of a metal, preferably nickel, platinum, palladium, ruthenium, rhenium or gold, optionally provided on the surface of a support material, preferably selected from the group consisting of active carbon, silica, titaniumoxide and aluminumoxide. Further, an alcohol, preferably methanol, may be added to the reaction to avoid re-polymerisation of the lignin-derived components. The alcoholic ingredient may be added in an amount of at least 5%, preferably at least 10%, more preferably at least 20%, at least 30%, most preferably at least 40% with respect to the total reaction volume.

(c) Electro-Oxidation of Modified Lignin-Derived Components

Alternatively, decomposition of modified lignin-derived components A in step 5) of the inventive method may be achieved by electro-oxidation.

"Electro-oxidation" is defined as an electrochemical process, wherein the oxidation reaction occurs by applying an electric field between two electrodes, e.g. a working electrode and a counter electrode, typically in an electrochemical cell such as a galvanic cell or a flow cell. The "working electrode" (electrode in an electrochemical system, on which the reaction of interest takes place) is cathodic or anodic, respectively, depending on whether the reaction on the electrode is reduction or oxidation. Common working electrodes may comprise inert metals, such as gold, silver or platinum, or inert carbon, such as glassy carbon or pyrolytic carbon, or mercury drop and film electrodes. The working electrode employed by the present invention may alternatively also be a nickel electrode. The counter electrode may be a platinum electrode, in particular whenever the working electrode is a nickel electrode. The electrodes may be, for example, sintered electrodes. Electro-oxidation advantageously allows instant operation on demand ("on/off"), does not use toxic chemicals, is specific (i.e. reduces the production of undesired by-products), can be operated at low reaction temperatures and requires low energy input.

"Electro-oxidation" preferably involves the oxidation of modified lignin-derived components A at the surface of an electrode and/or in an electrical (electrochemical) cell. A solution containing modified lignin-derived components A may be provided as the anolyte (i.e. the electrolyte under direct influence of the anode) or the catholyte (i.e. the electrolyte under direct influence of the cathode), preferably as the anolyte. A suitable electrolyte is preferably provided under the influence of the respective counter electrode (e.g. NaOH solution as the catholyte). Further, the modified lignin-derived components in solution may serve as anolyte and catholyte at the same time. Ions or salts (e.g. alkali salt, may be added to the electrolyte, e.g. a sodium salt, preferably sodium sulphate) may or may not be added to balance the charges of the reduction and oxidation reactions occurring under the influence of both electrodes. The use of acidic or alkaline electrolyte solutions may obviate the need for salts.

Electro-oxidation may preferably be performed under constant current in an alkaline solution, more preferably galvanostatically at pH 10 to 14. Alternatively, electro-oxidation may be conducted under acidic conditions.

(d) Enzymatic Degradation

Alternatively, decomposition of modified lignin-derived components A in step 5) of the inventive method may be achieved by enzymatic degradation.

Enzymatic degradation of modified lignin-derived components A may be accomplished with microbial or fungal enzymes under appropriate reaction conditions. Preferred enzymes may for instance be obtained from white-rot fungi such as *Phanerochaete* sp., *Pleurotus* sp., *Phlebia* sp., or bacterial species such as *Rhodococcus* sp., *Streptomyces* sp., *Pseudomonas* sp., *Amycolatopsis* sp., *Sphingobium* sp. and *Novosphingobium* sp., and include, without limitation, fungal extracellular lignin peroxidases, Mn peroxidases and laccases, and bacterial dye-decolorizing peroxidases (DyP), laccases and beta-etherase enzymes.

Further preferred bacterial enzymes for lignin conversion are disclosed in Bugg and Rahmanpour Curr Opin Chem Biol. 2015; 29: 10-7. Wong Appl Biochem Biotechnol 2009, 157:174-209 discloses further preferred fungal lignolytic enzymes.

Step (6) Isolation and Optional Purification of Low Molecular Weight Lignin-Derived Compounds Isolation and Purification Techniques In step 6) of the inventive method, the low molecular weight lignin-derived compounds (A) obtained from the chemical decomposition step 5) are isolated and/or purified.

Although the reaction conditions for the chemical decomposition step 5) of the inventive method are preferably chosen to avoid or minimize the formation of undesired by-products or re-polymerization, such reactions may not be entirely avoided.

The isolation and/or purification step 6) of the inventive method is preferably used to separate and thereby purify the low molecular weight lignin-derived compounds A from such re-polymerized or non-degraded higher molecular weight fragments, by-products, impurities, reactive agents, and so on. High(er) molecular weight fragments may include fragments of modified lignin-derived components derived from the pulping process that were not (sufficiently) decomposed, or re-polymerized, after chemical decomposition in step 4) of the inventive method. Fragments typically comprise or consist of tri- or n-mers of the building blocks of the modified lignin-derived components obtained by pulping in step 2) of the inventive method. Accordingly, such fragments typically exhibit a higher molecular weight than the desired low molecular weight lignin-derived compounds obtained from chemical decomposition, but exhibit a lower molecular weight than the modified lignin-derived components obtained from pulping in step 2). Such fragments typically do not fall within the definition of low molecular weight lignin-derived compounds as used herein.

In step 6) of the inventive method, the process stream of low molecular weight lignin-derived compounds A is preferably subjected to filtration and/or extraction.

The methods and process parameters chosen for isolation of the desired low molecular weight lignin-derived compounds A in step 6) of the inventive method typically depends on the type and nature of low molecular weight lignin-derived compounds. In the following, typical methods and process parameters suitable for isolating low molecular weight lignin-derived compounds A (which are preferably low molecular weight aromatic lignin-derived compounds as described in detail below) are discussed, which may however also be applicable to the isolation of other low molecular weight lignin-derived compounds B, C, D . . . .

Filtration may include ultrafiltration and nanofiltration, or combinations thereof. Filtration may preferably be carried out by using an ultrafiltration and/or nanofiltration cell, preferably having a pre-filtration section for increasing the efficiency of the filtration step (e.g. avoidance of membrane blockade, e.g. by higher molecular weight lignin-derived components). Stirred ultrafiltration cells as described by Duval et al. (Holzforschung 2015, 69, 127-134) may be applied as well. Preferably, the ultrafiltration and/or nanofiltration cell comprises at least one molecular weight cut-off unit, preferably at least two molecular weight cut-off units that enable the isolation of low molecular weight lignin-derived compounds within the desired molecular weight range, typically from 150 Da to 1.000 Da or from 150 to 500 Da. Preferably, a cascade of cut-off units (e.g. starting with one or more ultrafiltration cell(s) and one or more subsequent nanofiltration cell(s) with preferably decreasing cut-off values may be employed to fractionate the low molecular weight lignin-derived compounds obtained from chemical decomposition in step 4). Said compounds are usually fractionated in solution or may be isolated as dried matter and be re-dissolved thereafter, if required.

Preferably, step 6) of the inventive method thus comprises filtration and/or extraction of low molecular weight lignin-derived compounds A, preferably ultrafiltration and/or nanofiltration. Preferably, filtration is carried out in an ultra- and/or nanofiltration cell, preferably comprising at least one molecular weight cut-off unit, preferably at least two molecular weight cut-off units, wherein the at least one molecular weight cut-off unit has a cut-off level preferably of 1 kDa to 1.5 kDa; and optionally a pre-filtration section.

Step 6) of the inventive method may further comprise additional purification steps to further increase the purity of the low molecular weight lignin-derived compounds A. These purification steps are preferably performed after the isolation step described above. For instance, diafiltration against water may be used to remove residual sugars and reactive agents.

Alternatively, the low molecular weight lignin-derived compounds A may be isolated by extraction, optionally followed by fractional distillation.

The remaining lignin-derived fragments, or by-products, impurities, chemically reactive agents or catalysts from which the low molecular weight lignin-derived compounds A are separated in step 6) of the inventive method may be discarded, burned or recycled, e.g. in further rounds of chemical decomposition.

The isolated and purified low molecular weight lignin-derived compounds A may be obtained in step 6) in the form of a composition comprising or preferably (essentially) consisting of said low molecular weight lignin-derived compounds A, which is (essentially) free from higher molecular weight lignin-derived components, lignin-derived fragments, and other by-products, impurities, chemically reactive agents or catalysts.

Typically, the composition obtained after isolation and optionally purification in step 6) if the inventive method may preferably comprise several species (i.e. a mixture) of distinct low molecular weight lignin-derived compounds A as described below.

In step 6) of the inventive method, preferably low molecular weight aromatic lignin-derived compounds A are obtained. Said compounds are preferably monomers comprising one (typically monocyclic) aromatic ring system or dimers comprising typically two (non-annulated, typically monocyclic) aromatic rings linked to each other by a linker moiety, preferably an aliphatic linker, or by a bond. Typically, such compounds comprise or consist of benzene-derived, optionally substituted aromatic ring systems, preferably (optionally substituted) phenyl or biphenyl groups. The low molecular weight aromatic lignin-derived compounds A obtained from step 6) of the inventive method typically exhibit a molecular weight of less than 1.000 Da, preferably less than 700 Da, more preferably less than 500 Da, most preferably of about 100 to 500 Da, e.g. 200 to 400 Da.

Preferably, such compounds are based on a monomer or, alternatively, a homo- or heterodimer of the polymeric natural lignin, which may have been modified in the pulping process of step (1) of the inventive method. "Monomers" essentially correspond to the (repetitive) building blocks of polymeric natural lignin. A "monomer" may be any building block of the natural lignin polymer, which may be modified in step (1). "Monomers" of the natural lignin polymer are typically of aromatic nature (e.g. contain an aromatic ring system), but may be diverse in terms of their specific chemical character.

Low molecular weight aromatic lignin-derived compounds A obtained from isolation step 6) may be monomers characterized by General Formula (a):

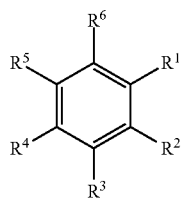

(a)

wherein
each of $R^1$-$R^5$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl; and $R^6$ is selected from the group consisting of hydrogen; hydroxy; linear or branched, optionally substituted, $C_{1-6}$ carboxyl; linear or branched, optionally substituted, $C_{1-6}$ aldehyde; and linear or branched, optionally substituted, $C_{1-6}$ alcohol.

Low molecular weight aromatic lignin-derived compounds A obtained from isolation step 6) may be dimers, wherein two aromatic monomers are directly connected by a bond or a (optionally aliphatic) linker group to form a homo- or heterodimer. A "heterodimer" comprises two aromatic ring systems with individual (distinct) substitution patterns. Heterodimers may preferably comprise two (optionally substituted) aromatic ring systems directly linked by a bond, thereby forming a biphenyl. Dimeric low molecular weight aromatic lignin-derived compounds A obtained from isolation step 6) may be characterized by General Formula (b):

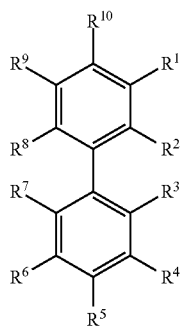

(b)

each of $R^1$-$R^9$ each of $R^1$-$R^9$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl: linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl; wherein $R^5$ is preferably hydroxy or optionally substituted $C_{1-6}$ alkoxy; and $R^{10}$ is selected from the group consisting of hydrogen; hydroxy; linear or branched, optionally substituted, $C_{1-6}$ carboxyl; linear or branched, optionally substituted, $C_{1-6}$ aldehyde; and linear or branched, optionally substituted, $C_{1-6}$ alcohol.

Low molecular weight aromatic lignin-derived compounds A obtained from isolation step 6) preferably comprise or consist of monomeric aromatic ring systems, and may more preferably be characterized by General Formula (a). Such compounds may be classified as (optionally substituted) benzenes or derivatives thereof, including phenols. Monomeric low molecular weight aromatic lignin-derived compounds A are typically derived from a monomer of the modified lignin-derived component obtained from step 4) of the inventive method.

Alternatively, low molecular weight aromatic lignin-derived compounds A obtained from isolation step 6) may comprise or consist of dimeric aromatic ring systems optionally forming a biphenyl group, and may more preferably be characterized by General Formula (b). Such a biphenylic system typically comprises phenylbenzene or 1,1'-biphenyl as essential chemical structure. Biphenylic moieties are typically formed by 5-5-linkage of natural lignin monomers. Such a bond occurs more frequently in softwood than in hardwood. For example, spruce may comprise more than 15%, preferably more than 20%, even more preferred more than 25% biphenylic moieties among its phenyl-propane units making up its natural lignin. Whenever biphenylic precursor compounds are envisaged, it may be preferred to use spruce wood as a lignocellulosic starting material in step (1) of the inventive method. Biphenylic precursor compounds may be further processed by chemical reactions, e.g. in further oxidizing reactions, in order to provide e.g. redox active compounds for multiple beneficial uses.

Alternatively, low molecular weight aromatic lignin-derived compounds A obtained from isolation step 6) may comprise or consist of multicyclic, optionally annulated aromatic ring systems.

The aromatic ring(s) of the compound A obtained from isolation step 5) is/are preferably substituted in at least one, preferably in at least two positions by a functional group, wherein the at least one functional group is preferably alkoxy or hydroxyl. A monocyclic compound A may typically be substituted in at least two positions by a functional group, wherein the functional group is preferably alkoxy or hydroxyl. A bicyclic and in particular biphenylic compound A may typically be substituted in at least one position per aromatic ring by a functional group, wherein the functional group is preferably alkoxy or hydroxyl. Preferably, in bicyclic and in particular biphenylic compounds A, each ring system exhibits its individual substitution pattern being different from the other substitution pattern of the other ring system.

Preferably, the at least one low molecular weight aromatic lignin-derived compound A may be selected from the group consisting of phenolic derivatives of biphenyl, benzylalcohol, benzalde-hydes and benzoic acid, preferably derivatives of p-hydroxy benzylalcohol, p-hydroxy benzaldehydes and p-hydroxy benzoic acid, or more preferably vanillin, guaiacol, eugenol, syringol, phenol, syringaldehyde, and derivatives or combinations thereof.

Preferably, the at least one low molecular weight aromatic lignin-derived compound A may be characterized by any one of the following chemical structures or corresponding esters thereof:

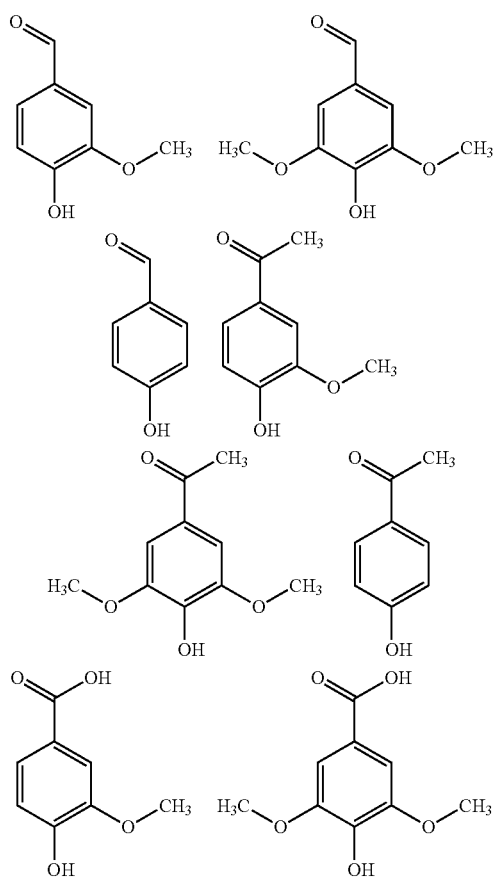

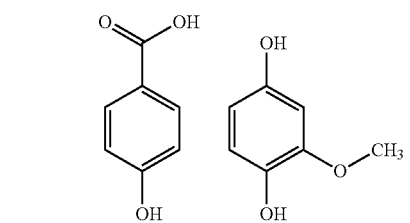

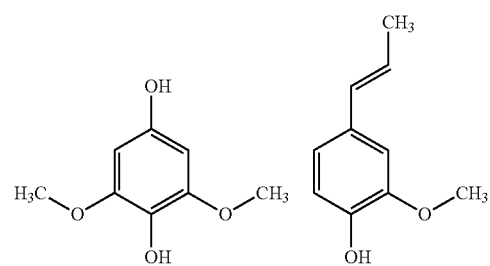

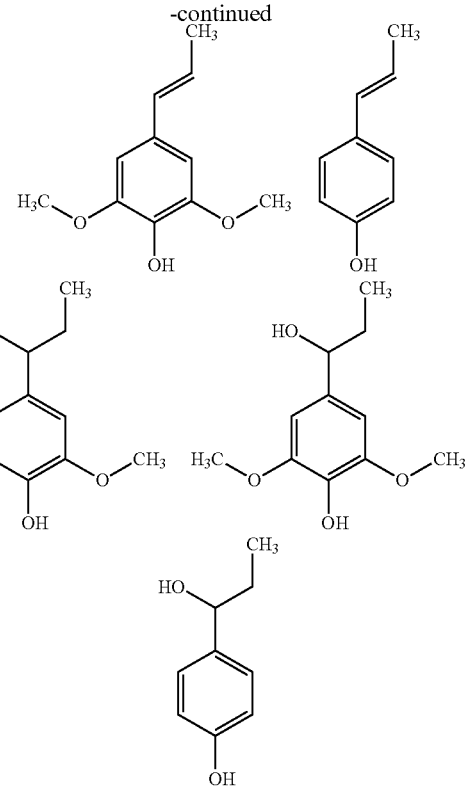

Step (7) Chemical Transformation

The preferably monomeric or dimeric low molecular weight aromatic lignin-derived compounds A obtained from step 6) of the inventive method may preferably further be subjected to at least one chemical transformation step.

A "chemical transformation reaction" includes any chemical reaction whereby substrates are modified with regard to their oxidation state, functional groups or chemical structures. By subjecting low molecular weight aromatic lignin-derived compounds A to such a chemical transformation reaction, altered substitution patterns or ring structures may for instance be introduced. "Chemically transformed" low molecular weight aromatic lignin-derived compounds A may thus be equipped with additional functional groups, be reduced or oxidized, and/or annulated to comprise bi-, tri- or multicyclic annulated aromatic ring systems.

It will be understood that the type and process parameters chosen for the chemical transformation reaction(s) depend on the low molecular weight aromatic lignin-derived compounds used as starting material, and on the desired end products obtained via the one or more chemical transformation reactions.

As discussed elsewhere herein, lignin-derived process stream A is preferably envisaged for the provision of low molecular weight aromatic lignin-derived quinone compounds A, which are preferably derivatized, more preferably sulfonated. Such compounds A are, inter alia, particularly useful as redox flow battery electrolytes.

The following paragraphs describe preferred chemical transformation reactions for preparing these compounds from lignin-derived process stream A. These reactions may however also be applied to other lignin-derived process streams (B, C, D . . . ) as well. Further chemical transformation reactions for obtaining other valuable lignin-derived compounds from lignin-derived process streams are described thereafter.

Annulation

Low molecular weight aromatic lignin-derived compounds A derived from step 6) of the inventive method may be subjected to an annulation reaction.

In annulation reactions, monocyclic low molecular weight aromatic lignin-derived compounds A can be reacted to annulated aromatic compounds comprising at least two annulated aromatic rings (also referred to as a "polycyclic" compound herein), which may preferably be bi-, tri-, tetra- or pentacyclic.

Said reaction type is typically known as annulation, which serves in organic chemistry as a chemical reaction, which allows to anneal two aromatic (mono-, di- or n-aromatic) ring systems. Preferably, the two or more precursor molecules of the annulation reaction are both or all e.g. monomeric or dimeric target compounds.

Annulation may be, for example, achieved by a Diels-Alder reaction or a Friedel-Crafts acylation. Preferably, low molecular weight aromatic lignin-derived compounds A may be subjected in step 7) of the inventive method to an annulation reaction, yielding lignin-derived low molecular weight aromatic lignin-derived bi-, tri- or polycyclic annulated compounds optionally characterized by any one of General Formulas (c), (d) or (e):

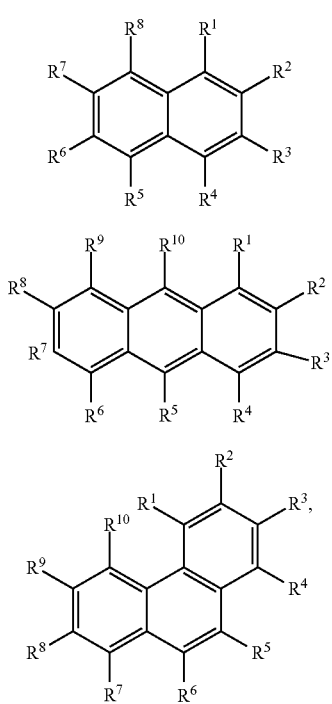

wherein
each of $R^2$, $R^3$, $R^5$-$R^8$ of Formula (c) is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy; linear or branched, optionally substituted, $C_{1-6}$ aldehyde; carboxylic acids; esters; oxo or carbonyl, wherein preferably at least one of $R^2$, $R^3$, $R^5$-$R^8$ is hydroxy or $C_{1-3}$ alkoxy, and $R^1$ and $R^4$ of Formula (c) is/are selected from the group consisting of hydrogen; hydroxy; linear or branched, optionally substituted, $C_{1-6}$ carboxyl; linear or branched, optionally substituted, $C_{1-6}$ aldehyde; and linear or branched, optionally substituted, $C_{1-6}$ alcohol, each of $R^1$-$R^{10}$ of Formula (d) is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde: carboxylic acids; esters; oxo or carbonyl, wherein preferably at least one of $R^2$, $R^5$, $R^6$ and $R^8$ is hydroxy or $C_{1-3}$ alkoxy, and $R^1$, $R^4$, $R^9$ and $R^{10}$ of Formula (d) is/are preferably selected from the group consisting of hydrogen; hydroxy; linear or branched, optionally substituted, $C_{1-6}$ carboxyl; linear or branched, optionally substituted, $C_{1-6}$ aldehyde; and linear or branched, optionally substituted, $C_{1-6}$ alcohol, each of $R^2$, $R^3$ and $R^7$-$R^{10}$ of Formula (e) is independently selected from hydrogen; hydroxy; carboxy; linear or branched, optionally substituted, $C_{1-6}$, alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters, oxo or carbonyl, wherein preferably at least one of $R^2$, $R^3$ and $R^7$-$R^{10}$ is hydroxy or $C_{1-3}$ alkoxy, and $R^1$, $R^4$, $R^5$ and $R^6$ of Formula (e) is selected from the group consisting of hydrogen, hydroxy, linear or branched, optionally substituted $C_{1-6}$ carboxyl, linear or branched, optionally substituted, $C_{1-6}$ aldehyde, and linear or branched, optionally substituted, $C_{1-6}$ alcohol.

Friedel-Crafts Acylation

Preferably, low molecular weight aromatic lignin-derived compounds A obtained from step 6) of the inventive method may be subjected to a Friedel-Crafts acylation for annulation.

Friedel-Crafts acylation reactions include the acylation of aromatic rings with an acyl chloride using a strong Lewis acid catalyst. Friedel-Crafts acylation is also possible with acid anhydrides. This reaction typically involves the acylation of an aromatic ring with an alkyl halide using a strong Lewis acid catalyst, e.g. an anhydrous ferric chloride as a catalyst.

The applicability Friedel-Crafts acylations to low molecular weight aromatic lignin-derived compounds obtained from step 6) of the inventive method came as a surprise; as these reaction are typically used in petrochemistry.

Diels-Alder Reaction

Alternatively, low molecular weight aromatic lignin-derived compounds A obtained from step 6) of the inventive method may be subjected to a Diels-Alder reaction for annulation.

In the context of the present invention, a Diels-Alder reaction is understood as an organic chemical reaction, typically a [4+2] cycloaddition, between a conjugated diene and a substituted alkene, commonly termed the dienophile, to form a substituted, preferably aromatic, cyclohexene system. The Diels-Alder reaction is particularly useful in synthetic organic chemistry as a reliable method for forming 6-membered systems with good control over regio- and stereochemical properties.

For example, through the conduction of a Diels-alder reaction, monocyclic low molecular weight aromatic lignin-derived compounds A obtained from step 6) of the inventive method may be extended to polycyclic, e.g. bicyclic, tricyclic, tetracyclic or even higher n-cyclic, compounds A. Without wishing to be bound by specific theory, it is believed that polycyclic compounds A (e.g., anthracenes) are particularly useful precursors for providing redox active compounds (e.g. anthraquinones).

By selecting an appropriate diene, benzoquinone structures can be converted to naphthacenes, anthracene and/or phenanthrenes. The fusion of a benzene ring onto an existing monocyclic compound A, preferably an oxidized compound such as quinone, may be accomplished on a ring which has two adjacent positions unsubstituted or substituted. However, unsubstituted positions are generally preferred due to higher yields. Hence, it is preferred in the context of the present invention that if a compound of more than one aromatic ring is desired, compounds are preferably subjected to further substitution reactions only after the annulation reaction was performed. It may be further advantageous in large-scale reactions to add one or more polymerization inhibitors known in the art. The Diels-alder reaction may be catalysed by any suitable catalyst known in the art, preferably by one or more metallic chlorides and/or zeolites. The subsequent oxidation step may or may not be necessary. If a reduced catalyst is still present from earlier reaction steps, the newly annulated ring may be instantly oxidized and aromatized, yielding in a multi-ring quinone. Alternatively, aeration in alkaline solution may be used, e.g., to obtain an anthraquinone derivative.

The condensation is preferably carried out prior to the optional downstream oxidation, and/or prior to derivatization in order to avoid, e.g. steric hindrance, and, in consequence, lower yields in condensed and derivatized product.

Oxidation

Low molecular weight aromatic lignin-derived compounds A obtained from step 6) (which may optionally have been annulated as described above) of the inventive method may be subjected to an oxidation reaction.

Said oxidation reaction preferably involves the treatment of (optionally annulated) low molecular weight aromatic lignin-derived compounds A with an oxidizing agent in the presence of a suitable catalyst.

Preferred oxidizing agents may be selected from $H_2O_2$, $O_2$ and air.

Preferred catalysts may be selected from heterogenous catalysts comprising or consisting of metal ions or metalloid elements. Alternatively, a homogenous catalyst comprising NaOH may be employed.

The choice of suitable catalysts may steer the oxidation reaction in a desired direction. E.g., it is envisaged that low molecular weight aromatic lignin-derived compounds A are preferably converted to sulfonated quinones A.

Accordingly, oxidation of low molecular weight aromatic lignin-derived compounds A may be accomplished using Co(II) complexes which have a high selectivity towards quinones. For example, (pyr)Co(II)salen may be employed in the presence of $O_2$ at overpressure, e.g. at least 3 bar. Such a reaction may preferably be conducted at room temperature in an organic solvent such as MeOH. Other preferred catalysts are Co(3-methoxysalen) and Co(N—N-Me salpr). In the latter case, the preferred organic solvent may be $CH_2Cl_2$.

Preferably, the oxidation of low molecular weight aromatic lignin-derived compounds A yields at least one quinone or hydroquinone as illustrated by the reaction schemes below:

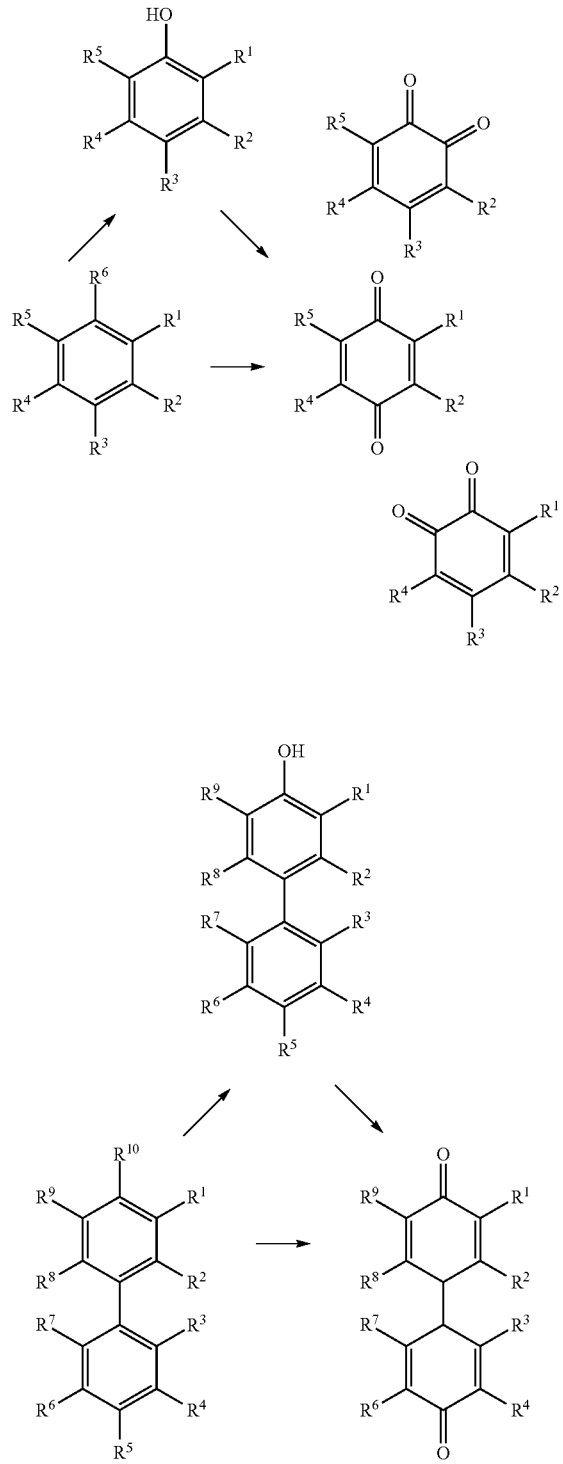

Accordingly, the oxidation of monocyclic low molecular weight aromatic lignin-derived compounds A may preferably yield at least one hydroquinone compound A characterized by General Formula (f):

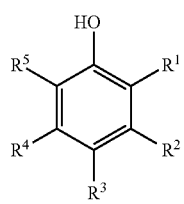

(f)

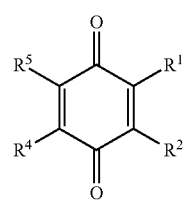

(h)

wherein each of $R^1$-$R^5$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy; linear or branched, optionally substituted, $C_{1-6}$ aldehyde; carboxylic acids; esters; oxo or carbonyl, and wherein one of $R^1$, $R^3$ and $R^5$ is hydroxy;

or by General Formula (g):

wherein each of $R^1$-$R^2$ and $R^4$-$R^5$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl; or

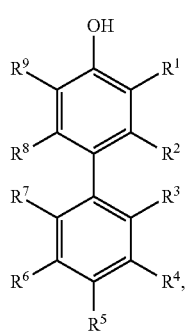

(g)

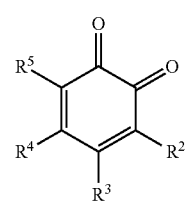

(i)

wherein each of $R^1$-$R^9$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl; and wherein $R^5$ is preferably hydroxy The obtained hydroquinone compound A may preferably be a redox active compound, which may be beneficial in a variety of uses. In particular, hydroquinone compounds A may be subjected to a further oxidation step and/or subjected to a sulfonation reaction, wherein the resulting sulfonated redox active (hydro-)quinone compound (A) is useful as a redox flow battery electrolyte.

Oxidation of Monocyclic Precursor Compounds to Quinones

More preferably, the oxidation of low molecular weight aromatic lignin-derived compounds A—under harsher reaction conditions than as described under (a) above—yields at least one quinone A characterized by the General Formulas below as illustrated by the reaction schemes depicted above.

Accordingly, the oxidation of monocyclic low molecular weight aromatic lignin-derived compounds A may preferably yield at least one quinone compound A characterized by General Formulas (h)-(k) or (l) below:

wherein each of $R^2$-$R^5$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl; or

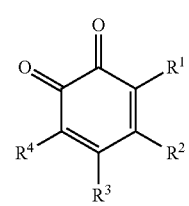

(j)

wherein each of $R^1$-$R^4$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl; or (k)

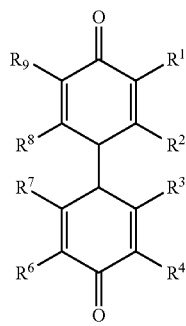

wherein each of $R^1$-$R^4$ and $R^6$-$R^9$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters, oxo or carbonyl.

Quinones characterized by any of the General Formulas above may either be provided by directly oxidizing the low molecular weight aromatic lignin-derived compounds (shown above) or via the intermediate of hydroquinones. E.g., said quinones may be provided by oxidizing the at least one hydroquinone, for instance, in the cell stack of a battery or by an oxidant, optionally in the presence of a heterogeneous catalyst. Usually, the provision of redox active hydroquinones A may be sufficient. Said hydroquinones A are particularly envisaged as redox flow battery electrolytes as described herein, and the chemical equilibrium between reduced (hydroquinone) and oxidized (quinone) forms will typically be established during the course of the redox reactions in the flow battery.

Preferably, oxidative cracking of modified lignin-derived components A and oxidation of low molecular weight aromatic lignin-derived compounds A may be accomplished in one step (also referred to as "combined cracking and oxidation" herein), such that the modified high(er) molecular weight lignin-derived components A are preferably chemically decomposed to yield low(er) molecular weight lignin-derived compounds (A), which are (instantaneously or concurrently) oxidized to quinone compounds A. Furthermore, reactive agents may be added to induce the concurrent introduction of further substituents in a one-pot reaction.

Combined cracking and oxidation may be achieved by electro-oxidation or catalyzed oxidation as described in the context of chemical decomposition in step 4) of the inventive method. For instance, a solution comprising modified lignin-derived components (A) may be diluted to a concentration below 20% (w/w), preferably below 10% (w/w), more preferably below 5% (w/w), even more preferably below 2% (w/w) and be subjected to electro-oxidation, and the pH optionally be adjusted to acidic conditions, or alternatively to alkaline conditions (pH 11-14, preferably at least pH 13). Electro-oxidation may preferably be conducted in a flow cell, wherein the flow is at least corresponding to 1 ml/min, preferably 10 ml/min or 50 ml/min, more preferably at least 200 ml/min, but may be up-scaled to significantly higher flows. Electro-oxidation may preferably be conducted galvanostatically, i.e. by applying a constant current of preferably at least 0.5 mA/cm², more preferably 1 mA/cm², even more preferably at least 5, 10 or 100 mA/cm2. Preferably, electro-oxidation may be performed for at least 10 min, preferably at least 30 min, alternatively for at least 1 hour, preferably for at least 4 hours.

Advantageously, combined cracking and oxidation may save time and resources, including reactants, reactive agents and/or process equipment. Combined cracking and oxidation may therefore be used in economic and simple methods for producing quinone compounds A by the inventive method.

Exemplary preferred quinone compounds A obtained by oxidation of low molecular weight aromatic lignin-derived compounds A include the following:

(I)

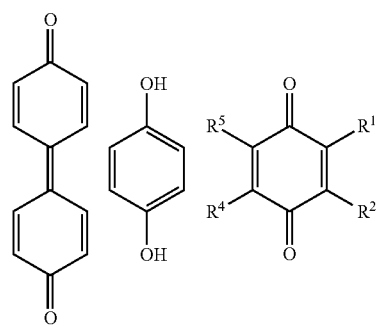

wherein in the compound according to General Formula (1) above, $R^1$, $R^3$, $R^5$ are independently selected from H, OH oder $C_1$-$C_6$ methoxy, preferably methoxy.

Oxidation of Annulated Polycyclic Low Molecular Weight Aromatic Lignin-Derived Compounds to (Hydro-) Quinones The above considerations with regard to monocyclic low molecular weight aromatic lignin-derived compounds are equally applicable to (annulated) polycyclic low molecular weight aromatic lignin-derived compounds. It is thus equally preferred that (annulated) polycyclic precursor compounds obtained from an annulation reaction or directly from step 6) of the inventive method are further subjected to an oxidation reaction. Said oxidation reaction is preferably accomplished in the presence of (i) an oxidizing agent selected from the group consisting of $H_2O_2$, $O_2$ and air, and (ii) a heterogeneous catalyst comprising a metal ion or a metalloid, or a homogeneous catalyst in the presence of NaOH (in which case, usually no catalyst comprising a metal ion or a metalloid is required). Said oxidation reaction preferably yields at least one quinone and/or hydroquinone compound characterized by any of General Formulas (d), (e) or (f) below:

(c)

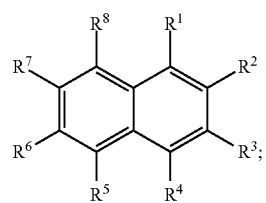

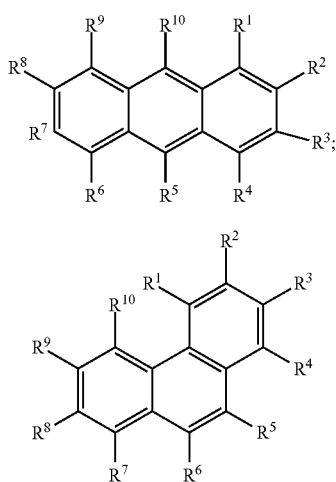

wherein each of $R^1$-$R^8$ with regard to Formula (c) and/or each of $R^1$-$R^{10}$ with regard to Formula (d) and (e) is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl;

wherein at least one of $R^8$ and $R^5$ or $R^1$ and $R^4$ of Formula (c) are hydroxy or oxo, or at least one of $R^9$ and $R^6$, $R^{10}$ and $R^5$, or $R^1$ and $R^4$ of Formula (d) are hydroxy or oxo, or at least one of $R^{10}$ and $R^7$ or $R^1$ and $R^4$ of Formula (e) are hydroxy or oxo.

An exemplary compound obtained by oxidation of polycyclic compound(s) (A) is characterized by Structural Formula (m) below:

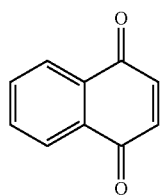

Isolation and/or Purification

Step 7) of the inventive method may further comprise one or more steps of isolating or purifying the obtained compounds.

Step 7) may include any isolation and/or purification method that allows the separation of desired compounds (either used as precursors for further processing or being desired target compounds) from the process stream. The isolation and/or purification steps may be conducted after any or each annulation, oxidation, reduction, derivatization reaction described herein.

For instance, an isolation and/or purification step may be conducted after optionally annulating and oxidizing low molecular weight aromatic lignin-derived compounds A to separate the resulting compounds A from undesired by-products, impurities, decomposition products, non-reacted products or catalysts.

Isolation and/or purification may preferably be accomplished by employing an extraction method, preferably precipitation, recrystallization, distillation, sublimation, solid phase extraction or fluid-fluid phase extraction as generally known in the art, with solid phase extraction, fluid-fluid phase extraction and precipitation being particularly preferred.

Substitution

Step 7) of the inventive method may further comprises subjection the low molecular weight aromatic lignin-derived compounds to a substitution reaction. As used herein the term "substitution" generally refers to a chemical reaction wherein one functional group in a chemical compound is replaced by another functional group.

Preferably, compounds A (or B, C, D . . . ) obtained from step 6) and optionally any of the chemical transformation reaction described herein under step 7) are subjected to a further substitution reaction in step 7) of the inventive method.

To that end, low molecular weight aromatic lignin-derived compounds A (or optionally B, C, D . . . ) may be treated with suitable chemically reactive agents to introduce at least one or more of the following functional groups: hydrogen; hydroxyl; carboxy; optionally substituted $C_{1-6}$ alkyl optionally comprising at least one heteroatom selected from N, O and S, including —$C_nH_{2n}OH$, —$C_nH_{2n}NH_2$ and —$C_nH_{2n}SO_3H$, wherein n is an integer selected from 1, 2, 3, 4, 5, or 6; carboxylic acids; esters; halogen; optionally substituted $C_{1-6}$ alkoxy, including methoxy and ethoxy; optionally substituted amino, including primary, secondary, tertiary and quaternary amines; amide; nitro; carbonyl; phosphoryl; phosphonyl; cyanide; and sulfonyl (—$SO_3H$), preferably in case of low molecular weight aromatic lignin-derived compounds A (or optionally B, C, D . . . ) at a position of the aryl structure other than those characterized by an oxo or hydroxyl group, wherein said group(s) is/are directly bound to the aryl structure or bound via an alkyl linker to the aryl structure, preferably via a methyl linker.

"Sulfonation" of low molecular weight lignin-derived compounds, preferably of low molecular weight aromatic lignin-derived quinone compounds A (obtained from the main process stream A) refers to the introduction of at least one sulfonyl group into the aryl structure of said compound. The sulfonyl group is preferably introduced into the compounds, in particular compounds according to any one of the Structural Formulas depicted herein, at a position of the aryl structure other than those characterized by an oxo or hydroxyl group, wherein said group(s) is/are directly bound to the aryl structure. The introduction of sulfonyl groups into the quinone compounds A obtained by step 7) of the inventive method preferably improves the solubility, electrochemical properties and/or stability of the resulting compounds. The resulting sulfonated lignin-derived low molecular weight aromatic quinone compounds are useful as redox active species in redox flow batteries.

Sulfonation may be carried out in the presence of concentrated aqueous sulfuric acid. Alternatively, sulphur trioxide may be mixed with inert gas, such as air, $N_2$ and/or $CO_2$, or complexed with a complexing agent such as pyridine, dioxane, $(CH_3)_3N$ or DMF. Typically, sulfonation is performed at increased temperatures of at least 50° C., preferably 100° C. to preferably increase the yield. Temperatures are preferably kept below 300° C., more preferably below 200° C. in order to avoid decomposition of the reactants by pyrolysis.

Sulfonation preferably includes (i) treatment of low molecular weight aromatic lignin-derived quinone compounds A (e.g. benzo-, naphtha-, anthraquinones) with $SO_3$, either from oleum or $SO_3$ gas. The reaction is preferably performed under atmospheric pressure or elevated pressure in concentrated sulfuric acid at a temperature of 40-300° C., preferably 60-120° C. for benzoquinones and 160-180° C. for anthraquinones. The reaction is performed within 1-6 hours, preferably 3 hours for benzoquinones and 4 hours for anthraquinones.

After the reaction, (i) the concentrated sulfuric acid may preferably be poured into water and partially neutralized. The preferred neutralizing agent is calcium hydroxide, the terminative sulfuric acid concentration is 5-30%, preferably 10-20%. After partially neutralizing the sulfuric acid, (iii) the precipitated sulphate may be filtered off. Subsequently, (iv) the resulting mixture may be directly concentrated, preferably under reduced pressure to yield a solution of 0.4-1.5 mol/L active material and 10-40% sulfuric acid. Alternatively, (v) the solution is completely neutralized either with the same or another neutralizing agent and the water is then evaporated under reduced pressure. Additional sulphates that eventually precipitate are filtered off such that the product precipitates. The remaining water is then evaporated and the solid is dried to yield a mixture of 30-90% sulfonated product mixed with sulphates.

Sulfonation typically yields a crude mixture of differently sulfonated low molecular weight aromatic lignin-derived quinone compounds (such as differently sulfonated benzo-, naphtha- or anthraquinones). The present inventors surprisingly discovered that this mixture of preferably differently substituted, e.g. sulfonated, quinone compounds may be instantly used as redox flow battery electrolytes. Thus, step 7) of the inventive method may preferably yield a lignin-derived composition comprising at least one sulfonated low molecular weight aromatic lignin-derived quinone compound. Said compound(s) are preferably redox active and may be used as redox flow battery electrolytes. Advantageously, even a composition A comprising a mixture of said compounds is useful as a redox flow battery electrolyte. The compound(s) and composition(s) described herein are advantageously obtainable from renewable sources (wood) and are moreover valorization products of lignocellulosic material which is otherwise treated as a waste material in the paper and pulp industry.

The obtained sulfonated low molecular weight aromatic lignin-derived quinone compounds may be subjected to any of the chemical transformation reactions or isolation/purification steps described under step 7) of the inventive method. In particular, isolation/purification of said sulfonated compound(s) may subsequently be carried out, for example, by filtration or salting out as described herein.

Step (8) Provision of Target Compounds

Preferably, the inventive method may comprise, optionally after step 3), 4) 5), 6) or 7) described herein, a step 8) of providing the desired cellulose- and lignin-derived target compounds A (or B, C, D . . . ) or compositions comprising the same. It will be understood that depending on the desired nature and characteristics of target compounds, the reaction products or isolates obtained after any one of steps 3), 4) 5), 6) or 7) may serve either as precursor compounds, or may be target compounds themselves.

The present invention envisages the provision of at least one type of target compounds, namely, preferably sulfonated quinones from lignin-derived process stream A. Said compounds may be provided in the form of pure target compounds, or mixtures of target compounds, or in the form of compositions comprising further components, e.g. solvents, additives, and the like.

Preferred ways of processing different process streams according to the inventive method are discussed below.
Process Streams
Cellulose-Derived Process Stream (Pulp)

The present invention envisages the processing of pulp into valuable chemical compounds and/or paper or paperboard products as described under step 3) of the inventive method.

Lignocellulosic material is provided and optionally prepared as described in the context of step 1) above. Subsequently, said lignocellulosic material is subjected to pulping as described in the context of step 2) above. The cellulose-derived process stream(s) obtained from pulping is subjected to pulp processing as described in the context of step 3) above.

Lignin-Derived Process Stream A: Provision of Quinone Compounds

In addition to the at least one pulp processing step 3) described above, the inventive method further comprises at least one step of processing a lignin-derived process stream A to yield valuable chemical products, more preferably sulfonated low molecular weight aromatic lignin-derived quinone compounds A.

Lignocellulosic material is provided and optionally prepared as described in the context of step 1) above. Subsequently, said lignocellulosic material is subjected to pulping, preferably to Kraft or sulphite pulping, as described in the context of step 2) above.

The lignin-derived process stream A obtained from pulping is subjected to isolation as described in the context of step 4) above. The process stream of modified lignin-derived components A obtained from isolation is subjected to chemical decomposition as described in the context of step 5) above. Preferably, modified lignin-derived components A may be subjected to oxidative cracking as described in the context of step 5) above, yielding a process stream of low molecular weight aromatic lignin-derived compounds A. Said compounds A are subjected to isolation and/or purification as described in the context of step 6) above. In a chemical transformation step 7), said low molecular weight aromatic lignin-derived compounds A are optionally annulated and/or oxidized, and sulfonated as described in the context of step 6) above, yielding sulfonated low molecular weight aromatic lignin-derived quinone compounds preferably characterized by Structural Formulas provided herein. The obtained sulfonated low molecular weight aromatic lignin-derived quinone compounds are preferably redox active compounds which are advantageously redox active and particularly useful as redox flow battery electrolytes.

Quinone compounds obtained from process stream A of the inventive method may preferably be subjected to at least one substitution reaction in step 7) (i.e., at least one of the "R" groups may be selected from a group which is different from H).

Substitution may preferably alter or confer important characteristics including solubility, stability, redox kinetics, toxicity, and potential or current market price.

Solubility may be particularly important for quinone compounds obtained from process stream A intended for use as redox flow battery electrolytes, because the mass transport limitation at high current density in a redox flow battery is directly proportional to the solubility. An increased solubility may advantageously increase the working concentration of the quinone compounds obtained from process stream A of the inventive method, reduce solvent costs and increase the energy density per unit volume/weight. The capacity of a redox flow battery depends on the effective concentration of redox active quinone compounds, which is the solubility multiplied by the number of electrons transferred in the redox reactions. Highly soluble redox active quinone compounds therefore preferably increase the energy capacity of the redox flow battery and are therefore preferred.

Quinone compounds obtained from process stream A of the inventive method may preferably be characterized by General Formula (1), (2) or (3), as defined above.

Said compounds may preferably be provided in aqueous solution for use in redox flow battery applications. Generally, unsubstituted quinone compounds may exhibit a limited solubility in water.

Water solubility may be enhanced by attaching polar groups such as ether, polyether, ester, sulfonyl or hydroxyl groups. Examples of such functional groups include, but are not limited to, —$SO_3H$/$SO_3^-$, —$PO_3H_2$/—$PO_3H^-$/—$PO_3^{2-}$, —COOH/—$COO^-$, —$OH$/—$O^-$, pyridinyl, imidazoyl, —$NH_2$/$NH_3^+$, $NHR$/$NH_2R^+$, $NR_2$/$NHR^{2+}$ and $NR_3^+$, wherein R is H or optionally substituted $C_{1-6}$ alkyl optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$. In step 7) of the inventive method, solubility-increasing groups may advantageously be introduced into quinone compounds obtained from process stream A in order to increase their solubility.

Stability is important not only to prevent chemical loss for long cycle life, but also because polymerization on the electrode can compromise the electrode's effectiveness. Stability against water and polymerization may be enhanced by replacing C—H groups (in particular those adjacent to C=O groups) with stable groups, e.g. selected from optionally substituted $C_{1-6}$ alkyl, optionally substituted $C_{1-6}$ alkoxy, hydroxyl, sulfonyl, amino, nitro, carboxyl, phosphoryl or phosphonyl.

Redox kinetics may be altered by adding electron-withdrawing groups (in order to preferably increase the standard reduction potential of the resulting substituted compound) or electron-donating groups (in order to preferably lower the standard reduction potential of the resulting substituted compound). Electron-withdrawing groups may be selected from —$SO_3H$/—$SO_3$, —$OH$/—$O^-$, —COR, —COOR, —$NO_2$, —$NR_3^-$, —$CF_3$, —$CCl_3$, —CN, —$PO_3H_2$/—$PO_3H^-$/—$PO_3^{2-}$, —COOH/—$COO^-$, —F, —Cl, —Br, —CHO, where R is H or $C_{1-10}$ alkyl. Electron-withdrawing groups may advantageously be introduced into quinone compounds obtained from process stream A in order to increase their standard reduction potential. The resulting redox active composition comprising such compounds (which may preferably be the first redox active composition of the inventive combination) may advantageously be used as the posilyte in the inventive redox flow batteries. In step 7) of the inventive method, electron-donating groups may be selected from $C_{1-6}$ alkyl, including methyl (—$CH_3$), ethyl (—$C_2H_5$), or phenyl, —$NH_2$, —NHR, —$NR_2$, —NHCOR, —OR, where R is H or $C_{1-10}$ alkyl. In step 7) of the inventive method, electron-donating groups may advantageously be introduced into quinone compounds obtained from process stream A in order to lower their standard reduction potential.

Preferred quinone compounds obtained from process stream A by the inventive method are preferably soluble in water, chemically stable and exhibit standard reduction potentials as defined elsewhere herein.

More preferably, quinone compounds obtained from process stream A by the inventive method are highly soluble in water, chemically stable in strongly acidic/basic solutions, and, when used in redox flow batteries, capable of providing high cell voltages of about 1 V, round-trip efficiencies >80%, and high discharge rates.

Accordingly, preferred quinone compounds obtained from process stream A by the inventive method may comprise electron-withdrawing or electron-donating groups for increasing or lowering the standard reduction potential (depending on whether the resulting composition is envisaged for use as a posilyte or negolyte, respectively) and optionally further substituents increasing their solubility in water. In principle, the said quinone compounds may comprise these substituents in any suitable combination.

Preferred (substituted) quinone compounds obtained from process stream A by the inventive method are specified below.

Preferably, in redox active compounds according to General Formula (1):

$R^1$ may be selected from —H, —$SO_3H$, optionally substituted $C_{1-6}$ alkyl and optionally substituted amine; $R^2$ may be selected from —H, —OH, —$SO_3H$, optionally substituted amine and $C_{1-6}$ alkoxy, preferably methoxy; $R^3$ may be selected from —H, —OH and $C_{1-6}$ alkoxy, preferably methoxy; and $R^4$ may be selected from —H, —$SO_3H$, optionally substituted $C_{1-6}$ alkyl, optionally substituted amine and halogen.

As indicated elsewhere herein, alkyl and alkoxy groups, in particular $C_{1-6}$ alkyl and alkoxy groups disclosed in connected with General Formulas (1), (2) and (3) herein, may be linear or branched, and optionally substituted or unsubstituted.

More preferably, in redox active compounds according to General Formula (1), $R^1$ and/or $R^4$ may be independently selected from substituted $C_{1-6}$, alkyl selected from —$R^5$—$SO_3H$, —$R^5$—$CO_2H$ and $R^5$—OH, wherein $R^5$ is $C_{1-6}$ alkyl optionally comprising at least one, optionally substituted, heteroatom selected from N, O or S; or $R^1$, $R^2$ and/or $R^3$ according to General Formula (1) may be selected from —$NH_2$/$NH_3^+$, —$NHR$/$NH_2R^+$, —$NR_2$/$NHR_2^+$ and —$NR_3^+$, where R is H or optionally substituted $C_{1-6}$ alkyl, optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$.

In particular, quinone compounds obtained from process stream A may be characterized one of the following Structural Formulas (1.1)-(1.10) (or the corresponding quinone forms thereof):

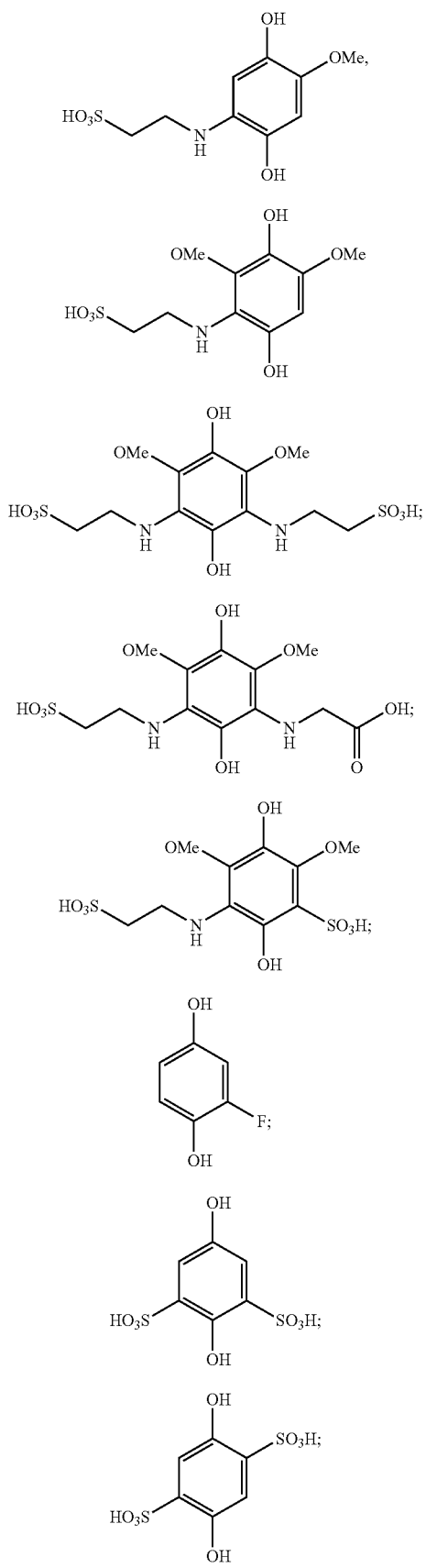

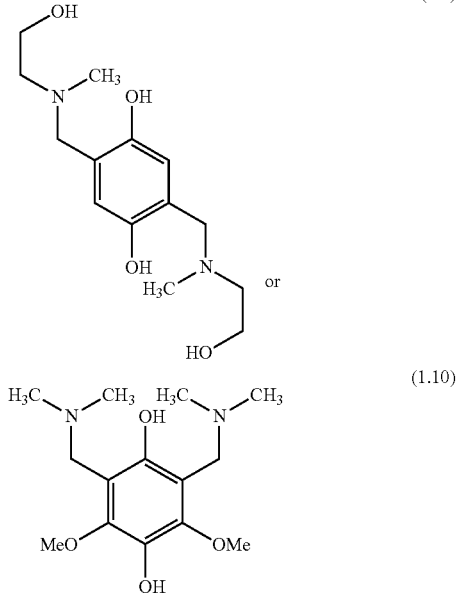

Preferably, in quinone compounds according to General Formula (2), $R^1$ and $R^2$ may be independently selected from —H, —OH and $C_{1-6}$ alkoxy, preferably methoxy; and $R^3$-$R^6$ may be independently selected from —H and —$SO_3H$.

According to the alternative annotation provided herein, in redox active compounds according to General Formula (2), $R^5$ and $R^6$ may be independently selected from —H, —OH and $C_{1-6}$ alkoxy, preferably methoxy; and $R^7$-$R^{10}$ may be independently selected from —H and —$SO_3H$.

Preferably, in quinone compounds according to General Formula (3), $R^1$, $R^2$ and $R^4$ may be independently selected from —H, —OH and $C_{1-6}$ alkoxy, preferably methoxy; and $R^3$ and $R^5$-$R^8$ may be independently selected from —H and —$SO_3H$.

More preferably, in quinone compounds according to General Formula (3), $R^1$ may be —$SO_3H$; $R^2$ may be —$SO_3H$ and $R^1$, $R^3$ and $R^4$ may preferably be —OH; $R^6$ may be —$SO_3H$, $R^1$ and $R^4$ or $R^1$, $R^2$ and $R^4$ may preferably be —OH; $R^2$ and $R^6$ may be —$SO_3H$, $R^1$ and $R^4$ or $R^1$, $R^3$ and $R^4$ may preferably be —OH; $R^3$ and $R^6$ may be —$SO_3H$; $R^1$, $R^2$ and $R^4$ may preferably be —OH; $R^2$ and $R^7$ may be —$SO_3H$; or $R^1$ and $R^4$ are —$SO_3H$; wherein each of the others of $R^1$-$R^8$ may be $C_{1-6}$ alkoxy or —H, preferably —H.

According to the alternative annotation used herein, preferably, in redox active compounds according to General Formula (3), $R^{11}$, $R^{12}$ and $R^{14}$ may be independently selected from —H, —OH and $C_{1-6}$ alkoxy, preferably methoxy; and $R^{13}$ and $R^{15}$-$R^{18}$ may be independently selected from —H and —$SO_3H$.

More preferably, in redox active compounds according to General Formula (3), $R^{11}$ may be —$SO_3H$; $R^{12}$ may be —$SO_3H$ and $R^{11}$, $R^{13}$ and $R^{14}$ may preferably be —OH; $R^{16}$ may be —$SO_3H$, $R^{11}$ and $R^{14}$ or $R^{11}$, $R^{12}$ and $R^{14}$ may preferably be —OH; $R^{12}$ and $R^{16}$ may be —$SO_3H$, $R^{11}$ and $R^{14}$ or $R^{11}$, $R^{13}$ and $R^{14}$ may preferably be —OH; $R^{13}$ and $R^{16}$ may preferably be —OH; $R^{12}$ and $R^{17}$ may be —$SO_3H$; or $R^{11}$ and $R^{14}$ are —$SO_3H$; wherein each of the others of $R^{11}$-$R^{18}$ may be $C_{1-6}$ alkoxy or —H, preferably —H.

In particular, quinone compounds may be characterized by Structural Formula (3.1) or a hydroquinone form thereof:

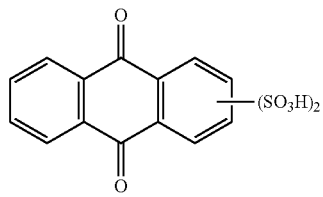

(3.1)

Further preferred quinone compounds obtained from process stream A by the inventive method include 1,4-benzoquinone-2,5-disulfonic acid, 1,4-benzoquinone-2,6-disulfonic acid, 1,4-benzoquinone-2-sulfonic acid, 1,4-naphthoquinone-2,6-disulfonic acid, 1,4-naphthoquinone-2,7-disulfonic acid, 1,4-naphthoquinone-5,7-disulfonic acid, 1,4-naphthoquinone-5-sulfonic acid, 1,4-naphthoquinone-2-sulfonic acid, 9,10-anthraquinone-2,6-disulfonic acid, 9,10-anthraquinone-2,7-disulfonic acid, 9,10-anthraquinone-1,5-disulfonic acid, 9,10-anthraquinone-1-sulfonic acid and 9,10-anthraquinone-2-sulfonic acid, or hydroquinone forms thereof.

Process Stream B: Pyrolysis and Optionally Catalytic Upgrading

In addition to processing of process stream A (and optionally any other process streams) as described herein, the inventive method may further preferably comprise at least one step of subjecting a process stream B to pyrolysis and optionally subsequent catalytic upgrading. Said process stream B is preferably rich in lignin or lignin derivatives (such as modified lignin-derived components or low molecular weight lignin-derived compounds.

Process stream B may be separated from the process stream A of the inventive method prior to or after step 1) (provision and optionally preparation of lignocellulosic material), after step 2) (pulping), after step 4) (isolation/purification of modified lignin-derived components), after step 5) (chemical decomposition) or after step 6) (isolation/purification of low molecular weight lignin-derived compounds).

Alternatively, process stream B may be separated from any other of the process streams described herein.

It will be acknowledged that if the process stream is separated from the main process stream A prior to step 2) (pulping), a step of dissolving lignocellulosic biomass and/or lignin may be required prior to further processing as described herein, thereby preferably rendering it more accessible for further (downstream) chemical reactions. Several solvents and extraction strategies have been reported and are envisaged in the context of the present invention, including, without limitation, cuprammonium hydroxide, DMSO/SO$_2$, DMSO/TBAF, DMSO/NMO; CO$_2$-expanded organic solvents; ionic liquids; and supercritical CO$_2$. Further solvents and extraction systems are discussed in Zakseski et al. Chem Rev. 2010, 110 (6): 3552-3599.

Lignin or lignin derivatives of process stream B are preferably subjected to pyrolysis. "Pyrolysis" refers to the thermochemical decomposition of organic material at elevated temperatures under anaerobic conditions, i.e. in the absence of oxygen (and typically also any halogen). Pyrolytic degradation typically starts at about 473 K. It is believed that linkages between the lignin units are cleaved between about 473 and 673 K.

The pyrolysis of lignin and its derivatives, including underlying chemical reactions, reaction conditions and reaction products, is extensively discussed by Amen-Chen et al. Biores Tech 79 (2001) 277-299 and by Zakseski et al. Chem Rev. 2010, 110 (6): 3552-3599.

Generally, the products from lignin pyrolysis can be divided into gaseous hydrocarbons together with carbon monoxide and carbon dioxide, volatile liquids (water, methanol, acetone, acetaldehyde) and monophenols (phenol, guaiacol (o-methoxyphenol), catechol (o-dihydroxybenzene) and other polysubstituted phenolic compounds. These higher molecular weight species are typically present in the liquid oil fraction ("pyrolysis oil").

Zeolite catalysts may be added to increase oil yields and decrease char formation by removing oxygen, resulting in products with a higher C/O ratio. Pyrolysis oil yields and the selectivity towards different products may be controlled by changing operating conditions such as temperature, time and reactor loading, or by altering catalyst variables such as zeolite Si/Al ratio or acidity.

The pyrolysis oil may subsequently be subjected to catalytic upgrading. "Catalytic upgrading" may refer to any chemical reaction involving the contacting of pyrolysis oil with a suitable catalyst to preferably obtain valuable chemicals or fuels. Specifically, catalytic upgrading may include the catalytic hydrodeoxygenation of pyrolysis oil, i.e. the removal of oxygen from the hydrocarbon products.

Pyrolysis oil may be catalytically upgraded by contacting with a suitable catalyst. Preferred catalysts for catalytic upgrading of pyrolysis oil include, without limitation, zeolites such as H-ZSM-5; tungsten carbide (W$_2$C) optionally supported on MCM-41; Pt-catalysts supported by alumina such as Pt/Al$_2$O$_3$; and TiO$_2$.

Other methods to obtain lignin oils include the depolymerisation in supercritical solvents and base-catalyzed depolymerization, which consists of heating a solution of lignin and inorganic base in water at high pressures.

Lignin-oils obtained by pyrolysis or alternative methods typically consist of oxygen-rich (alkyl-substituted) aromatic monomers, dimers and trimers, forming an oxygen-rich mixture of aromatic molecules with high water content, low vapor pressure and high viscosity. For the production of value-added chemicals or fuels, the removal of oxygen functionalities is typically desired. Hydrodeoxygenation (HDO) is an effective away to remove oxygen from oxygen-functionalized aromatics.

Catalytic upgrading of pyrolysis oil or other lignin oils may further involve the hydrodeoxygenation over suitable catalysts including, without limitation, sulfided CoMo/Al$_2$O$_3$ and NiMo/Al$_2$O$_3$ catalysts; optionally supported noble metal catalysts such as Pd, Pt, Ru but also Ni-based catalysts; Mo$_2$/CNF.

Preferred target compounds obtained or obtainable by pyrolysis and optionally catalytic upgrading of process stream B include, without limitation, benzenes, toluenes, xylenes, naphthalenes, polycyclic aromatic hydrocarbons, guaiacol, syringol, and derivatives thereof.

Pyrolysis may be conducted in the presence of additives, including hydrogen-donor reagents, such as tetralin (1, 2, 3, 4-tetrahydronaphthalene), optionally in combination with phenol; anthracene; naphthalene; xylene, pyridine; alcohols such as methanol, 2-propanol, or combinations thereof; each of the aforementioned compounds or combinations optionally under H$_2$ atmosphere and/or in combination with a suitable catalysts, such as Fe$_2$O$_3$, sulphided and non-sulphided ferrocene catalysts; Cu(II) acetate; ZnCl$_2$ or combinations thereof. Further, suitable additives such as alkaline or neutral salts or additives may be used, including NaOH; $K_2CO_3$; $Na_2CO_3$; KCl; NaCl; KOH; or combinations thereof.

Preferably, process stream B may yield monolignols, monophenols, volatile compounds, gaseous compounds, polysubstituted phenols, and biochar, which may optionally be isolated/purified and/or subjected to further chemical transformation reactions.

Exemplary compounds obtained or obtainable by processing process stream B as described herein include, without limitation, 1-(3,4-dimethoxyphenyl)-2-(mehoxyphenoxy) ethylene; 1-(4-hydroxy-3-methoxy-phenyl)-3-hydroxy-propanone; 2,3-dihydroxyanisole; 2,3-dimethoxyphenol; 4-methylguaiacacol; 4-methylsyringol; 4-propenylphenol; 4-propylcatechol; 4-propylphenol; 4-propylphenoxyacetaldehyde; 4-vinylguaiacol; 4-vinylveratrone; acetoguaiacone; acetonguaiacone; acetosyringone; acetovanillone; acetoveratrone; alkenyl guaiacol; alkyl catechols; alkyl guaiacols; alkyl-phenols; allylbenzene; anisole; aromatic aldehydes; benzaldehyde; benzene; benzene alkyl derivatives; $C_1$-$C_3$ alcohols; carbon monoxide; carboxylic acids; catechol; cinnamaldehydr; conferaldehyde; coniferyl alcohol; coumaryl alcohol; cresol; di-, trihydroxybenzenes; dihydroxyanisole; dihydroxybenzene alkyl derivatives; ethyl; ethyl phenols; ethylguaiacol; eugenol; formaldehyde; guaiacol; guaiacol vinylketone; homoveratraldehyde; isoeugenol; ketones; methane; methanol; methoxyphenols; methylguaiacol; methylsyringol; phenol; propyl; propylphenol; sinapaldehyde; sinapyl alcohol; syringaldehyde; syringol; sytrene; toluene; trimethylphenols; vanillin; veratrole; vinyl phenol; and xylenols; or derivatives of any of the aforementioned compounds.

Process Stream C: Lignin Catalytic Oxidation

In addition to processing of process stream A (and optionally any other process streams) as described herein, the inventive method may further preferably comprise at least one step of separating and subjecting a process stream C to oxidation, preferably catalytic oxidation. Said process stream C is preferably rich in lignin or lignin derivatives (such as modified lignin-derived components or low molecular weight lignin-derived compounds).

Without wishing to be bound by specific theory, it is envisaged that the catalytic oxidation of lignin or its derivatives of process stream C preferably forms complex aromatic compounds with additional functionalities, such as specific aromatic alcohols, aldehydes, acids, and other specially functionalized aromatics.

Process stream C may be separated from the process stream A of the inventive method prior to or after step 1) (provision and optionally preparation of lignocellulosic material), after step 2) (pulping), after step 4) (isolation/purification of modified lignin-derived components), after step 5) (chemical decomposition) or after step 6) (isolation/purification of low molecular weight lignin-derived compounds). Alternatively, process stream C may be separated from any other of the process streams described herein.

It will be acknowledged that if the process stream is separated from the main process stream A prior to step 2) (pulping), a step of dissolving lignocellulosic biomass and/or lignin may be required prior to further processing as described herein, thereby preferably rendering it more accessible for further (downstream) chemical reactions. Several solvents and extraction strategies have been reported and are envisaged in the context of the present invention, including, without limitation, cuprammonium hydroxide, $DMSO/SO_2$, DMSO/TBAF, DMSO/NMO; $CO_2$-expanded organic solvents; ionic liquids; and supercritical $CO_2$. Further solvents and extraction systems are discussed in Zakseski et al. Chem Rev. 2010, 110 (6): 3552-3599.

The catalytic oxidation of lignin or its derivatives of process stream C preferably includes contacting lignin or lignin derivatives with an oxidizing agent, preferably in the presence of a suitable catalyst, and optionally further additives. Oxidation of lignin and its derivatives is typically accomplished in alkaline media, such as in aqueous NaOH solution.

Suitable oxidizing agents (oxidants) may be selected from air, oxygen (optionally in combination with $CuSO_4$ as a catalyst), $H_2O_2$, nitrobenzene; and CuO. The (catalysed) oxidation with oxygen or CuO may be particularly preferred.

Preferred catalysts for the oxidation of lignin or its derivatives of process stream C are discussed in Zakseski et al. Chem Rev. 2010, 110 (6): 3552-3599, and include heterogenous catalysts comprising or consisting of metals or metal oxides, the metals preferably being selected from, without limitation, platinum (Pt), nickel (Ni), iron (Fe), rhenium (Re), titanium (Ti), manganese (Mn), or combinations thereof, such as Cu—Ni—Ce or Cu—Mn. Alternatively, electrocatalysis may be applied, where lignin or its derivatives are oxidized at the surface of an electrocatalyst (e.g. a Pt, Au, Cu, or Ni electrode) in a suitable solvent such as methanol. The oxidation of lignin or its derivatives in the presence of homogenous catalysts represents a particularly promising approach towards the production of value-added chemicals. Particularly preferred catalysts for the oxidation of lignin or its derivatives of process stream C therefore include homogenous catalysts selected from, without limitation, metalloporphyrins such as TPP, TMP, TF5PP or TPPS complexing Fe, Co or Ru; Schiff-base catalysts such as Co(salen) (where Salen=[N,N'-bis(salicylidene)ethane-1,2-diaminato]); nonporphyrinic catalysts such as tetraamido macrocyclic ligand (TAML), manganese-1,4,7-trimethyl-1,4,7-triazacyclononane (TACN) and manganese 1,2-bis-(4,7-dimethyl-1,4,7-triazacyclonon-1-yl)ethane (DTNE); polyoxometalates (POMs); simple metal salts such as CuO, $CuSO_4$, $FeCl_3$ or combinations thereof; or others.

The catalytic oxidation of lignin or its derivatives of process stream C may be accomplished at an alkaline pH at about 12 or more. The reaction may preferably be run at elevated temperatures of about 120° C. or more, more preferably about 130° C. or more, even more preferably between about 130-200° C., and most preferably between about 150-170° C. The reaction time may typically be about 3 hours or less, preferably about 2 hours or less, more preferably between about 2 hours and 30 minutes.

Process stream C preferably yields specific aromatic alcohols, aldehydes, carboxylic acids, ketones, phenols, and other specially functionalized aromatics that are difficult to produce. Vanillin (3-methoxy-4-hydrobenzaldehyde) is a preferred example of a high-value product obtainable from process stream C.

Further preferred compounds obtained or obtainable from process stream C are depicted in the Table below (adapted from Fache et al. ACS Sustainable Chem. Eng. 2016, 4, 35-46):

| | Compound | Formula |
|---|---|---|
| aldehydes | vanillin | 4-hydroxy-3-methoxybenzaldehyde structure |
| | syringaldehyde | 4-hydroxy-3,5-dimethoxybenzaldehyde structure |
| | p-hydroxy-benzaldehyde | 4-hydroxybenzaldehyde structure |
| carboxylic acids | vanillic acid | 4-hydroxy-3-methoxybenzoic acid structure |
| | syringic acid | 4-hydroxy-3,5-dimethoxybenzoic acid structure |
| ketones | acetovanilline | 4-hydroxy-3-methoxyacetophenone structure |
| | acetosyringone | 4-hydroxy-3,5-dimethoxyacetophenone structure |

-continued
| Compound | | Formula |
|---|---|---|
| phenolics | phenol | 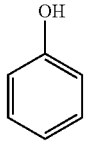 |
| | benzoic acid | 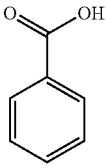 |
| | hydroxybenzoic acid | 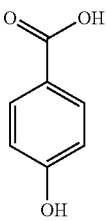 |
| | guiacaol | 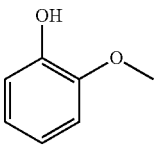 |
| | catechol | 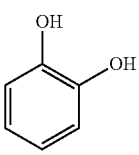 |
| | 3-methoxy catechol | 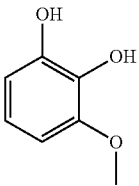 |
| | syringol | 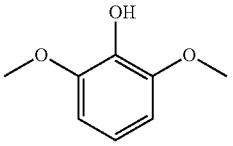 |
| | pyrogaliol | 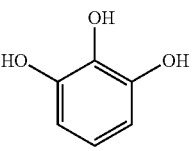 |
| | 4-methyl catechol | 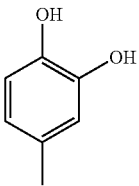 |

-continued

| Compound | Formula |
| --- | --- |
| 4-methyl syringol | |
| 4-ethyl catechol | |
| 2-(4-hydroxy-3-methoxyphenyl)acetaldehyde | |
| 2-(4-hydroxy-3,5-dimethoxyphenyl)acetaldehyde | |
| dehydrodivanillin | |
| 1,2-bis(4-hydroxy-3-methoxyphenyl)ethane-1,2-dione | |

-continued

| Compound | | Formula |
|---|---|---|
| other compounds | 1,2,3-trimethoxybenzene | |
| | 2-hydroxy-3-methyl-2-cyclopentenone | |
| | 3-ethyl-2-hydroxy-2-cyclopentenone | |
| | 3,4-dimethyl maleic anhydride | |
| | butyrolactone | |
| | maleic acid | |
| | fumaric acid | |
| | succinic acid | |
| | malonic acid | |
| | propionic acid | |
| | oxalic acid | |
| | acetic acid | |

-continued

| Compound | Formula |
|---|---|
| formic acid |  |

Derivatives, esters and salts of these compounds are also envisaged herein.

Said compounds may be isolated and/or purified in or may optionally be subjected to chemical transformation reactions, yielding derivatives of the compounds shown in the table above.

Vanillin (4-hydroxy-3-methoxybenzaldehyde) is of particular interest, as it is the world's most used flavoring and fragrance ingredient in the food or cosmetic industries and is furthermore the most available pure monoaromatic phenol currently produced at an industrial scale from lignin. Advantageously, vanillin is a safe aromatic compound bearing two reactive functions that can be chemically modified (the methoxy group being less reactive than the aldehyde and phenol functions). Vanillin can thus be considered as a difunctional compound, which is useful to prepare thermoplastic polymers. It is available on an industrial scale from well-described, ever improving processes. Thus, vanillin has the potential to be a key renewable aromatic building block for the production of valuable chemical compounds and products, such as renewable polymers. Syringaldehyde is a valuable starting material for the pharmaceutical industry, as it is a precursor for 3,4,5-trimethoxybenzaldehyde.

Vanillin and its derivatives are therefore particularly envisaged as target compounds obtained or obtainable from process stream C according to the inventive method.

Process Stream D: Lignin Catalytic Cracking and Hydrolysis

In addition to processing process stream A (and optionally any other process streams) as described herein, the inventive method may further preferably comprise at least one step of separating and subjecting a process stream D to catalytic cracking and/or hydrolysis. Said process stream D is preferably rich in lignin or lignin derivatives (such as modified lignin-derived components or low molecular weight lignin-derived compounds.

Process stream D may be separated from the process stream A of the inventive method, typically prior to or after step 1) (provision and optionally preparation of lignocellulosic material), or alternatively after step 2) (pulping), after step 4) (isolation/purification of modified lignin-derived components) or after step 5) (chemical decomposition) or step 6) (isolation/purification of low molecular weight lignin-derived compounds). Alternatively, process stream D may be separated from any other of the process streams described herein.

The catalytic cracking of lignin or its derivatives of process stream D may be accomplished using optimized zeolites in an acid-catalyzed reaction. In the hydrocracking process, the catalytic cracking of lignin or its derivatives is combined with a hydrogenation/hydrogenolysis step.

Suitable catalysts are preferably bifunctional, combining a support active in cracking, which may typically consist of zeolites or amorphous silica-alumina with various compositions, with a (noble) metal such as cobalt, tungsten, palladium, or nickel for the hydrogenation reaction. Particularly, suitable catalysts may be selected, without limitation, from H-ZSM-5; H-Y; silicalite; silica; Pt/Al2O3-SiO2; sulfided Ni—W/SiO$_2$—Al$_2$O$_3$, Ni—Mo/SiO$_2$—Al$_2$O$_3$; optionally sulfided Co—Mo/Al$_2$O$_3$; supported or non-supported Pt-modified superacid catalysts, such as Pt/SO$_4^{2-}$/ZrO$_2$, Pt/WO$_4^{2-}$/ZrO$_2$, or Pt/SO$_4^{2-}$/TiO$_2$.

The processing of process stream D by catalytic cracking, in particular hydrocracking, typically yields a crude mixture of aromatic or aliphatic hydrocarbons, including e.g. $C_1$-$C_4$ alkyl substituted phenols and methoxyphenols.

Hydrolysis of lignin or its derivatives may be accomplished by subjecting lignin or its derivatives of process stream D to alkaline hydrolysis in supercritical water, KOH in supercritical methanol or ethanol; or NaOH and Ca(OH)$_2$.

The processing of process stream D by hydrolysis, may yield e.g. phenols, such as syringol, as well as higher value-added products including 2-methoxyphenol, 4-hydroxy-3-methoxybenzaldehyde, 2,6-dimethoxyphenol, and 1-(4-hydroxy-3-methoxyphenyl)ethanone.

Process Stream E: Catalytic Reduction (Hydrogenation/Hydrodeoxygenation)

In addition to processing of process stream A (and optionally any other process streams) as described herein, the inventive method may further preferably comprise at least one step of separating and subjecting a process stream E to reduction, preferably catalysed reduction, in particular hydrogenation and/or hydrodeoxygenation. Said process stream E is preferably rich in lignin or lignin derivatives (such as modified lignin-derived components or low molecular weight lignin-derived compounds.

Without wishing to be bound by specific theory, it is envisaged that hydrogenation and/or hydrodeoxygenation of lignin or its derivatives of process stream E preferably (partially or completely) removes alcohol, aldehyde, ether and acid substituents from low molecular weight lignin-derived species to form simpler aromatics, such as benzene, toluene, xylene (BTX) and phenols.

Process stream E may be separated from the process stream A of the inventive method, typically prior to or after step 1) (provision and optionally preparation of lignocellulosic material), or alternatively after step 2) (pulping), after step 4) (isolation/purification of modified lignin-derived components) or after step 5) (chemical decomposition) or step 6) (isolation/purification of low molecular weight lignin-derived compounds). Alternatively, process stream E may be separated from any other of the process streams described herein.

It will be acknowledged that if the process stream is separated from the main process stream A prior to step 2) (pulping), a step of dissolving lignocellulosic biomass and/or lignin may be required prior to further processing as described herein, thereby preferably rendering it more accessible for further (downstream) chemical reactions. Several solvents and extraction strategies have been reported and are envisaged in the context of the present invention, including, without limitation, cuprammonium hydroxide, DMSO/SO$_2$, DMSO/TBAF, DMSO/NMO; CO2-expanded organic solvents; ionic liquids; and supercritical CO$_2$. Further solvents and extraction systems are discussed in Zakseski et al. Chem Rev. 2010, 110 (6): 3552-3599.

The catalytic hydrogenation and/or hydrodeoxygenation of lignin or its derivatives of process stream E preferably includes contacting lignin or lignin derivatives with a hydrogen donor-agent, preferably in the presence of a suitable catalyst, and optionally further additives.

Suitable hydrogen donor-agents for the catalytic hydrogenation and/or hydrodeoxygenation of lignin or its derivatives of process stream E may be selected from $H_2$, or hydrogen-donor solvents such as tetralin, dioxane, phenols, methanol, isopropanol, formic acid or $H_3PO_4$. Compared to neat pyrolysis, the presence of a hydrogen donating compound may advantageously lead to higher yields of monophenols and less char formation. The presence of hydrogen atoms in the medium preferably mediates a higher degree of dehydroxylation. The hydrogen donor also prevents, through hydrogenation, allyl and vinyl substituents to be degraded, resulting in a higher amount of ethyl and propyl substituted phenols.

Preferred catalysts for the catalytic hydrogenation and/or hydrodeoxygenation of lignin or its derivatives of process stream E are discussed in Zakseski et al. Chem Rev. 2010, 110 (6): 3552-3599, and include, without limitation, heterogenous catalysts comprising precious or transition metal based catalysts comprising platinum (Pt), ruthenium (Ru), rhodium (Rd), nickel (Ni), copper (Cu), iron (Fe), molybdenum (Mo), tungsten (W) or combinations thereof, such as Co—Mo, Ni—Mo, Rh—Co, Ni—Cu or Ni—W; preferably supported by a suitable material such as carbon, $Al_2O_3$, $SiO_2$—$Al_2O_3$, MgO, zeolites, or $ZrO_2$. Alternatively, electrocatalysis may be applied, where chemisorbed hydrogen, generated in situ at the surface of the electrocatalyst (usually a Raney-Ni electrode) by water electrolysis, reacts with the adsorbed organic substrate. As a further alternative, homogenous catalysts selected from, without limitation, rhodium and rhutenium complexes, may be applied for the catalytic hydrogenation and/or hydrodeoxygenation of lignin or its derivatives of process stream E.

Among the many hydrodeoxygenation techniques, catalysed high pressure hydrodeoxygenation (HDO) is believed to be particularly efficient. To that end, lignin or its derivatives of process stream E may be treated with gaseous hydrogen with a total hydrogen pressure of up to about 40 bar. The reaction may preferably be run at increased temperatures of about 150° C. or more, more preferably about 200° C. or more, even more preferably between about 250° C. The reaction time may typically be about 1 hours or more, preferably about 1.5 hours or more, more preferably about 2 hours. The reaction may be conducted at constant stirring with a speed of about 400 rpm.

The present invention also envisages subjecting lignin or its derivatives of process stream E to the Lignol process, where catalytic hydrogenation of lignin is followed by non-catalytic, thermal hydrodealkylation.

The choice of reactants, catalysts, and process parameters (such as duration, temperature, pressure of the reaction) typically determines the yield and nature of compounds obtained from the catalytic hydrogenation and/or hydrodeoxygenation of lignin or its derivatives of process stream E.

Preferably, the catalytic hydrogenation and/or hydrodeoxygenation of lignin or its derivatives of process stream E yields simpler aromatics or cycloalkanes, including cyclopentane, methyl cyclopentane, cyclohexane, methyl cyclohexane, 1-methoxycyclohexane, cyclopentamethanol, benzene, methoxy benzene, 1,2-dimethoxy-benzene, phenol, 2-methoxy-5-methyl-phenol, 2-methoxy-4-methyl-phenol, 1,1'-bicyclohexyl. More preferably, process stream E may be used to provide aromatics with reduced functionalities, in particular phenols, benzene, toluene, and xylene (BTX).

Process Stream F: Enzymatic Conversion

In addition to processing of process stream A (and optionally any other process streams) as described herein, the inventive method may further preferably comprise at least one step of separating and subjecting a process stream F to enzymatic conversion. Said process stream F is preferably rich in lignin or lignin derivatives (such as modified lignin-derived components or low molecular weight lignin-derived compounds.

Process stream F may typically be separated from the main process stream A of the inventive method prior to or after step 1) (provision and optionally preparation of lignocellulosic material), after step 2) (pulping), after step 4) (isolation/purification of modified lignin-derived components) or after step 5) (chemical decomposition) or step 6) (isolation/purification of low molecular weight lignin-derived compounds).

The enzymatic conversion of lignin and its derivatives is inter alia reviewed in Bugg Rahmanpour Curr Opin Chem Biol. 2015; 29: 10-7.

Enzymatic conversion of lignin, lignin-derived components and/or compounds of process stream F may be accomplished by contacting lignocellulosic material, lignin or lignin-derived components or compounds with microbial or fungal enzymes under appropriate reaction conditions. Preferred enzymes may for instance be obtained from white-rot fungi such as *Phanerochaete* sp., *Pleurotus* sp., *Phlebia* sp., or bacterial species such as *Rhodococcus* sp., *Streptomyces* sp., *Pseudomonas* sp., *Amycolatopsis* sp., *Sphingobium* sp. and *Novosphingobium* sp., and include, without limitation, fungal extracellular lignin peroxidases, Mn peroxidases and laccases, and bacterial dye-decolorizing peroxidases (DyP), laccases and beta-etherase enzymes.

Further preferred bacterial enzymes for lignin conversion are disclosed in Bugg and Rahmanpour Curr Opin Chem Biol. 2015; 29: 10-7. Wong Appl Biochem Biotechnol 2009, 157:174-209 discloses further preferred fungal lignolytic enzymes.

Process Stream G: Further Reactions and Processes

In addition to processing of process stream A (and optionally any other process stream) as described herein, the inventive method may further preferably comprise at least one step of separating and subjecting at least one further process stream G to treatment or processing for further applications. Said process stream G is preferably rich in lignin or lignin derivatives (such as modified lignin-derived components or low molecular weight lignin-derived compounds.

Process stream G may be separated from process stream A of the inventive method prior to or after step 1) (provision and optionally preparation of lignocellulosic material), after step 2) (pulping), after step 4) (isolation/purification of modified lignin-derived components) or after step 5) (chemical decomposition) or step 6) (isolation/purification of low molecular weight lignin-derived compounds). Alternatively, process stream G may be separated from any other of the process streams described herein.

It will be acknowledged that if the process stream is separated from the main process stream A prior to step 2) (pulping), a step of dissolving lignocellulosic biomass and/or lignin may be required prior to further processing as described herein, thereby preferably rendering it more accessible for further (downstream) chemical reactions. Several solvents and extraction strategies have been reported and are envisaged in the context of the present invention, including, without limitation, cuprammonium hydroxide, DMSO/SO2, DMSO/TBAF, DMSO/NMO; CO2-expanded organic solvents; ionic liquids; and supercritical CO2. Further solvents and extraction systems are discussed in Zakseski et al. Chem Rev. 2010, 110 (6): 3552-3599.

Process stream G may be subjected to downstream processing to obtain carbon fibres, as e.g. described by Baker and Rials. J Appl Polym Sci 2013, 130:713-728. Processing may typically involve at least one isolation/purification step to remove any impurities such as polysaccharides, salts, water and other volatiles. Subsequently, the high-purity lignin may be subjected to melt spinning at high rates to obtain carbon fibres.

Process stream G may be subjected to downstream processing to obtain phenol-formaldehyde adhesives, as e.g. described by Jin et al. Biores Technol 2010, 101:2046-2048.

Process stream G may be subjected to downstream processing to obtain phenolic resins, as e.g. described by Ramires et al. Biotech Bioeng 2010, 107:612-621.

Process stream G may be subjected to downstream processing to obtain polyurethane foams and elastomers, as e.g. described by Pan and Saddler Biotech Biofuels 2013, 6:12. Lignin may either be directly used for polyurethane synthesis, i.e. without any preliminary chemical modification (alone or in combination with other polyols). Alternatively, lignin may be subjected to further chemical transformations, e.g. by making the hydroxyl functions more readily available by e.g. esterification and etherification reactions. Since lignin contains both aliphatic and aromatic hydroxyl groups, it can potentially act as reactive sites for isocyanate groups (formation of urethane linkages). Optionally, oxypropylation may be applied to graft poly(propylene oxide) on the lignin, allowing the hydroxyl groups to be released on the outer shell of the polymer (particularly the phenolic groups entrapped inside the molecule). Consequently, the solid lignin becomes a liquid polyol with an optimal hydroxyl index for polyurethane foam formulations. The (optionally chemically modified) lignin may then be incorporated into polyurethane to form rigid polyurethane (RPU) for use as foams and elastomers that may be used in the construction, automotive industry, freeze sectors, equipment manufacturing, nautical applications.

Process stream G may be subjected to downstream processing to obtain porous carbon, as e.g. described by Zhang et al. ChemSusChem 2015, 8:428-432.

Process stream G may be subjected to downstream processing to obtain lignin nanocontainers, as e.g. described by Yiamsawas et al. RSC Adv 2014, 4:11661-11663.

Process stream G may be subjected to downstream processing to obtain ethanol, e.g. by may be subjected to hydrolysis with sulfuric acid or hydrochloric acid at 20-40° C. (CHAP method), or with diluted acid at high temperature (CASH method).

Process stream G may be separated from the main process stream A after sulphite pulping in step 2). The obtained lignosulfonates may—after optional further isolation/purification steps—be directly used as additives. Lignosulfonates interalia find use in the concrete and cement industry due to their strong dispersing agents properties allows using less water to form workable mixtures. The resulting concrete preferably has a higher density, better uniformity, higher compressive strength and better durability. Lignosulfonates are also used as set retarding agents where concrete must remain fluid over extended periods of time. Lignosulfonates may also be used for controlling dust and surface stabilization of cement. Furthermore, potassium lignosulfonates can be used in up till 30 wt % in slow-release fertilizers to improve the chelating of a variety of metal ions in the soil and increasing the solubility of nitrogen, phosphorus and potassium in the soil. Their binding properties increase hardness and avoid cracking and dust in storing of e.g. animal feed pellets to fertilizers. Advantageously, lignosulfonates are nontoxic and eco-friendly above the concentration level used.

Process stream G may be subjected to radiative degradation. Lignin is sensitive towards UV radiation. Lignin or its derivatives in process stream G may thus be subjected to UV radiation, optionally in the presence of a suitable catalyst such as $TiO_2$. Thereby, quinones may be formed from phenoxyl radicals in a process involving oxygen centered radicals. Several photochemical pathways for the formation of the phenoxyl radicals are presented in Scheme 4 of Dorrestijn et al. J. Anal. Appl. Pyrolysis 54 (2000) 153-192.

It is also conceivable and envisaged herein to separate several process streams G from the main process stream A and subject them to the processing described above to obtain several distinct value-added lignin-derived products.

EXAMPLES

The examples shown in the following are merely illustrative and shall describe the present invention in a further way. These examples shall not be construed to limit the present invention thereto. The following preparations and examples are given to enable those skilled in the art to more clearly understand and to practice the present invention. The present invention, however, is not limited in scope by the exemplified embodiments, which are intended as illustrations of single aspects of the invention only, and methods, which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Preparation of Low Molecular Weight Aromatic Lignin-Derived Compounds by Cracking and Reduction by a Nickel Catalyst Reductive cracking of a modified lignin-derived component of the inventive method may for example be carried out by means of a catalyst comprising nickel, e.g. supported on activated carbon (Ni/C). The catalysts are typically prepared by an incipient-wetness impregnation method and further treated by a carbothermal reduction method known in the art.

Herein, nickel nitrate(II) hexahydrate [Ni(NO$_3$)$_2$ 6H$_2$O] is used and optionally added into water in a beaker known in the art. The solution is then stirred, e.g. for at least 30 min, to prepare an impregnation stock solution. Activated carbon having a water absorption capacity of typically above 1.8 mL g$^{-1}$ is added into the solution and the beaker may then covered by a culture dish to keep the sample wet for a prescribed time, preferably more than 12 h, more preferably 24 h. The sample is then dried at a temperature above 80° C., e.g. 120° C. overnight. The actual reduction is carried out in a container such as a preferably horizontal furnace in a flow of inert gas such as N$_2$. The flow is, e.g., 10 mL min$^{-1}$ or more, preferably 30 mL min$^{-1}$ or more. The reduction temperature preferably reaches at least 400° C., preferably 450° C., e.g. over set time period such as at least 30 min, preferably at least 60 min. The temperature for conducting the reduction is maintained at 450° C. for at least 1 h, more preferably for at least 2 h. The Ni/SBA-15 catalysts are reduced at 550° C. for 2 h. The Ni/Al$_2$O$_3$ catalyst is reduced at 700° C. for 2 h. The metal loading for each nickel- and copper-based catalyst is 10% (w/w) relative to the support. Herein, birch sawdust serves as lignocellulosic material and is treated with the ethanol-benzene mixture (v/v ratio 1:2) for 12 h. The treated birch sawdust, solvent (m/v 1:20), and catalyst (w/w 20:1) are placed in an autoclave reactor. The reactor is sealed and purged with Ar 4 to 6 times to expel air. Then, the reducing reaction is conducted at 200° C. at a stirring speed of at least 300 rpm, preferably 500 rpm. When the desired reaction time (usually 2 to 10 h) is reached, the reactor is cooled to ambient temperature before sampling.

Typically, the reaction generates 4-propylguaiacol and 4-propylsyringol as major products, together with minor alkene-substituted 4-propylguaiacol and 4-propylsyringol, as determined by standard gas chromatography. The compounds are isolated according to step (F), preferably by extraction.

Example 2: Preparation of Monomeric Aromatic Lignin-Derived Molecules from Lignosulfonate of a Sulfite Process by Electrooxidation Lignosulfonate is provided by step (2) according to the present invention. Thereof, a 1 M aqueous NaOH solution is prepared, comprising 1% (W/W) lignosulfonate. Said solution is subjected to an electrooxidation according to step (5). Therein, the solution is employed as anolyte. A 1 M aqueous solution is employed as catalyte. A flow cell with a flow rate of 250 ml/min is used. Electrolysis is allowed to take place galvanostatically for 8 h applying current of 1 mA/cm$^2$. A typical resulting voltage is 1.4 V. The voltage curve typically is asymptotic and the solution changes preferably color from brown to dark brown.

Samples of the solution are taken every hour over a time span of 8 h and subsequently examined photometrically. Thereof, an absorption profile typical for ortho-benzoquinone is determined. Hence, a lower molecular weight aromatic lignin-derived compound, quinone compound, is prepared by said method.

Said compound is then isolated according to step (F) of the present invention. Therefore, said compound is extracted by dichloromethane and subsequently subjected to cycles of charging and discharging processes in a flow cell. The voltage curve shows that the compound is redox active, which may be reversibly electrolyzed.

Example 3: Preparation of an Annulated Quinone Compound by a Friedel-Crafts Acylation Vanillin as a low molecular weight aromatic lignin-derived compound is provided by step (6) of the inventive method. Said compound is further annulated and oxidized according to step (7) according to the present invention in five steps as follows:

(i) Synthesis of 4-(benzyloxy)-3-methoxybenzaldehyde (2)

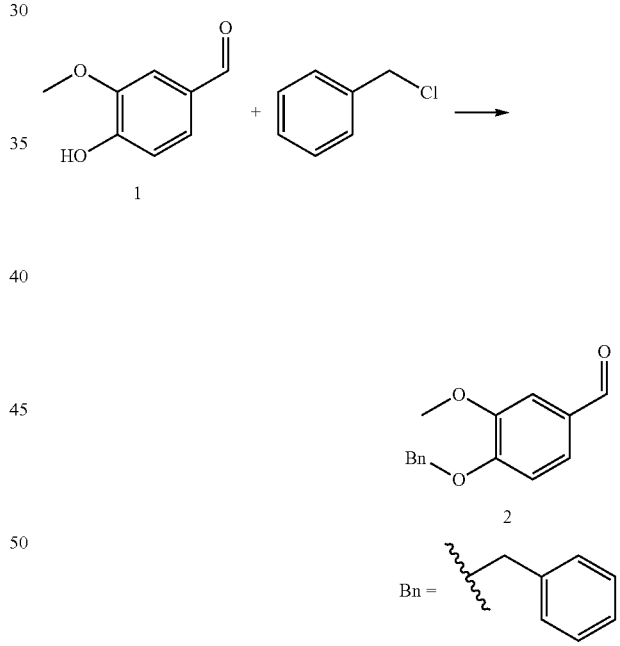

Vanillin (1) (1.0 eq.) and benzyl chloride (1.2 eq.) are dissolved in N,N-dimethylformamide and potassium iodine (0.5 mol %) is added. Afterwards potassium carbonate is added and the reaction is stirred above 60° C., preferably between 60 to 120° C. for at least 1 h, preferably 1 to 8 h. After completion of the reaction, the solution is diluted with distilled water and extracted with an appropriate solvent. The organic phase is washed with brine and the product is then isolated from the organic phase.

(ii) Synthesis of 4-(benzyloxy)-3-methoxybenzoic acid (3)

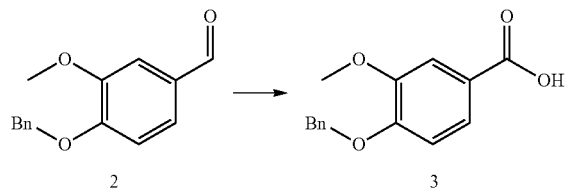 [SMILES: COc1cc(C=O)ccc1OCc1ccccc1 ; COc1cc(C(=O)O)ccc1OCc1ccccc1]

A mixture of 1,2-dimethoxyethane and potassium hydroxide (5 to 20 eq.) is purged with oxygen and the calculated amount of isolated product 2 (1.0 eq.) is added. After the absorption of oxygen ceases, the mixture is diluted with distilled water and neutral organic products are extracted with an appropriate solvent. The aqueous layer is acidified and the acidic organic products are extracted with an appropriate solvent. Product 3 is isolated from the organic layer.

(iii) Synthesis of 4-(benzyloxy)-3-methoxybenzoyl chloride (4)

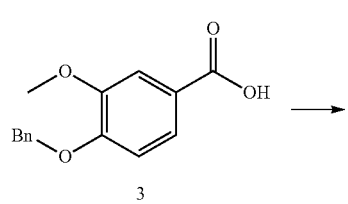

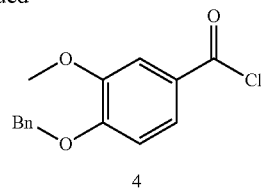

Isolated product 3 (1.0 eq.) is dissolved in thionyl chloride (5-20 eq.) and the mixture is stirred at 60 to 120° C. for 1 to 8 h. After completion of the reaction excess thionyl chloride is evaporated to yield desired acyl chloride 4.

(iv) Synthesis of Anthraquinones (5-7)

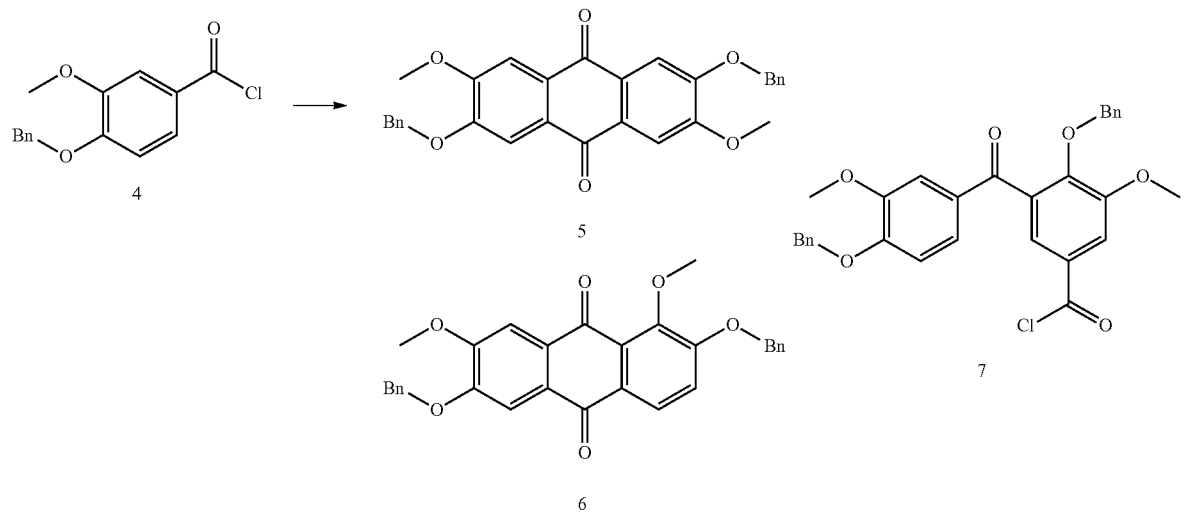

Aluminiumtrichloride (0.1 eq.) is added to the crude acyl chloride 4 and the mixture is stirred for 30 to 300 min at −20 to 60° C. After completion of the reaction the mixture is carefully quenched with bicarb solution. The product is extracted with an appropriate solvent and the organic layer is washed with brine. The product is then isolated from the organic phase.

(v) Synthesis of 2,6-dihydroxy-3,7-dimethoxyanthracene-9,10-dione 8 and 2,6-dihydroxy-1,7-dimethoxyanthracene-9,10-dione 9

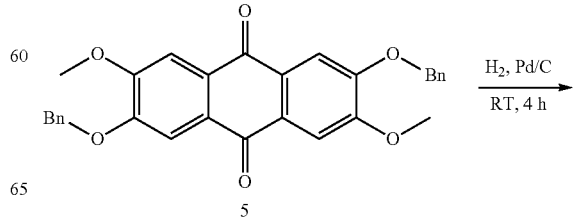

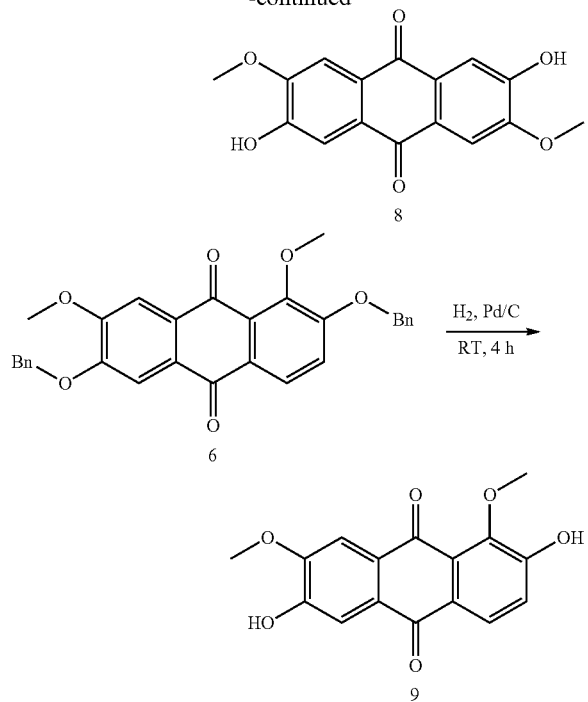

Anthraquinone 5 or 6 are dissolved in ethyl acetate, methanol or ethanol and palladium on charcoal (1 to 30 weight %) is added. The mixture is stirred at room temperature under hydrogen atmosphere (1-10 bar). The catalyst is filtered off and the product (9) is isolated from the mixture.

The product is then characterized by spectrographic means, and provided as redox active compound according to the present invention.

Example 4: Derivatization of (Hydro-)quinones

Substituents are introduced into the low molecular weight lignin-derived components according to step (7) of the inventive method.

Example 4.1: Reduction of Dimethoxy Benzoquinone

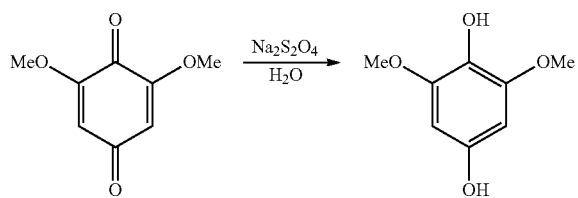 [SMILES: COC1=CC(=O)C=C(OC)C1=O ; "Na2S2O4" ; O ; COc1cc(O)cc(OC)c1O]

23.2 g of sodium dithionite (0.134 mol, 1.32 eq.) was added to the suspension of 17.0 g (0.101 mol, 1.0 eq.) 2,6-dimethoxycyclohexa-2,5-diene-1,4-dione in 100 mL H$_2$O. After 2 h stirring at room temperature the precipitate was filtered off and dried in the air to give 15.85 g (0.093 mol, 92% yield) of 2,6-dimethoxybenzene-1,4-diol as a white solid.

Example 4.2: Oxidation of Methoxy Benzohydroquinone

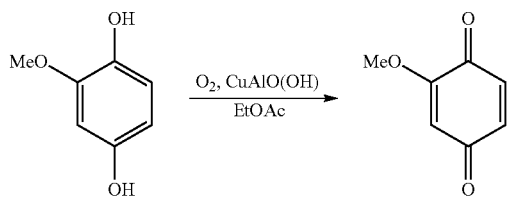

1.4 g of catalyst Cu/AlO(OH) was added to a solution of 8.2 g (0.059 mol) 2-methoxy-1,4-dihydroxybenzene in 250 mL ethyl acetate, and the reaction mixture was stirred at room temperature for 147 h under an O$_2$ atmosphere. After the conversion determined by HPLC reached 99%, the reaction mixture was filtered, and the recovered catalyst was washed with ethyl acetate (100 mL×3). The filtrate was collected and solvent was removed in vacuo to give 7.66 g (0.055 mol, 95% yield) of 2-methoxycyclohexa-2,5-diene-1,4-dione as a yellow-brownish solid.

Example 4.3: Acetylation of Methoxy Benzohydroquinone 8.24 g (0.059 mol, 1.0 eq.) of 2-methoxybenzene-1,4-diol was weighed into a 250 mL reaction flask equipped with a reflux condenser. 60 mL of dichloroethane and 15 mL (0.159 mol, 2.7 eq.) of acetic anhydride were added. 12 mL (0.096 mol, 1.63 eq.) of boron trifluoride ether solution was then slowly added at room temperature with stirring. The reaction mixture was heated to 90° C. for 20 hours. The mixture was cooled to 60° C., 30 mL H$_2$O was added followed by 10 mL HCl (6 M). The resulting mixture was heated to 100° C. for 30 min, cooled down and extracted with ethyl acetate (150 mL×3). The combined extracts were washed sequentially with H$_2$O (100 mL), saturated sodium bicarbonate (100 mL) and H$_2$O (100 mL) and then dried with anhydrous sodium sulfate. The solvent was removed in vacuo to give a brown solid residue, which was washed with methanol to give 7.49 g (0.041 mol, 70% yield) of 1-(2,5-dihydroxy-4-methoxyphenyl)ethan-1-one as a beige solid.

Example 4.4: Addition of Isonicotinic Acid to Benzoquinone 2.16 g (0.02 mol, 1.0 eq.) of p-benzoquinone was suspended in 6.4 mL of acetic acid. 2.46 g (0.02 mol, 1.0 eq.) of nicotinic acid was added and the mixture was stirred for 2 h at rt. The resulting dark mixture was diluted with 3 mL of water and treated with 6.6 mL of HCl (6 M). On cooling, solid precipitated which was filtered off and dried overnight at 60° C. to give 3.13 g (0.012 mol, 59% yield) of 3-carboxy-1-(2,5-dihydroxyphenyl)pyridin-1-ium chloride as an yellow solid.

Example 4.5: Sulfonation of Anthraquinone

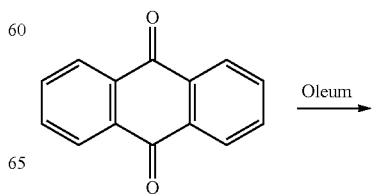

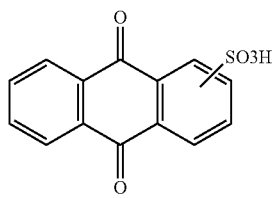

A solution of anthraquinone was heated (180° C.) in a solution of 20%-40% SO₃ in concentrated sulfuric acid (oleum), resulting in a mixture of sulfonated anthraquinones. The crude mixture was poured onto ice and partially neutralized with calcium hydroxide. Subsequently, the mixture was filtrated and concentrated to yield the final product.

Example 4.6: Sulfonation of Hydroquinone (1,4-Dihydroxybenzene)

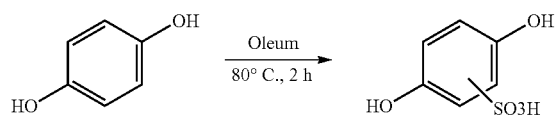

A solution of hydroquinone was heated (80° C.) in a solution of 20%-40% SO₃ in concentrated sulfuric acid (oleum), resulting in a mixture of sulfonated hydroquinones. The crude mixture was poured onto ice and partially neutralized with calcium hydroxide. Subsequently, the mixture was filtrated and concentrated to yield the final product.

Example 4.7: Sulfonation of 1,4-Dihydroxy-2,6-dimethoxybenzene

A solution of hydroquinone was heated (80° C.) in a solution of 20%-35% SO₃ in concentrated

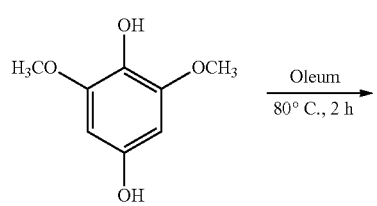

sulfuric acid (oleum), resulting in a mixture of sulfonated 1,4-dihydroxy-2,6-dimethoxybenzenes. The crude mixture was poured onto ice and partially neutralized with calcium hydroxide. Subsequently, the mixture was filtrated and concentrated to yield the final product.

Example 4.8: Sulfonation of 2-Methoxyhydroquinone

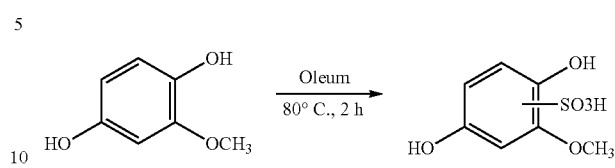

A solution of 2-methoxyhydroquinone was heated (80° C.) in a solution of 20%-40% SO₃ in concentrated sulfuric acid (oleum), resulting in a mixture of sulfonated 2-methoxyhydroquinones. The crude mixture was poured onto ice and partially neutralized with calcium hydroxide. Subsequently, the mixture was filtrated and concentrated to yield the final product.

Example 4.9: Synthesis of 2,5-bis{[(2-hydroxyethyl)(methyl)amino]methyl}benzene-1,4-diol

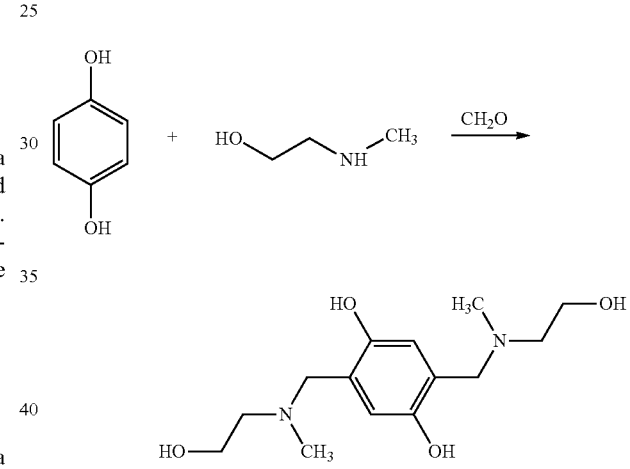

In a round-bottom flask 40.0 g hydroquinone (0.36 mol, 1 eq) and 24.0 g paraformaldehyde (0.80 mol, 2.2 eq) were dissolved in toluene (200 mL). 64 mL 2-(methylamino)ethanol (0.80 mol, 2.2 eq) was added and the reaction mixture was heated under reflux for 20 h. After cooling to room temperature the solvent was removed in vacuum and the residue was recrystallized from acetone to yield 65.2 g of product (63% yield) as an off-white solid.

Example 4.10: Synthesis of 2,6-bis[(dimethylamino)methyl]-3,5-dimethoxybenzene-1,4-diol

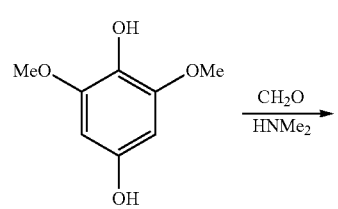

-continued

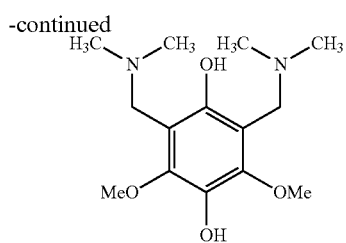

8.51 g 2,6-dimethoxyhydroquinone (50 mmol, 1 eq) and 3.30 g paraformaldehyde (110 mmol, 2.2 eq) were dissolved in ethanol (130 mL). 19 mL of dimethylamine solution in ethanol (5.6 M, 110 mmol, 2.2 eq) was added and the reaction mixture was stirred at room temperature for 20 h. After completion of the reaction, the solvent was removed in vacuum to obtain 12.2 g of product (86% yield). Analytically pure sample was obtained by recrystallization from acetone.

Example 5: Model Compounds from the Modification Reaction of Benzoquinones Paired with Sulfonated Anthraquinone in an Organic Redox Flow Battery Table 4 shows three examples for pairings that were used in a fully organic redox flow battery that were achieved by the modification of quinones. Example A shows a pairing of a sulfonated benzohydroquinone that was achieved by a double substitution reaction with sulfur trioxide and a sulfonated anthraquinone that was also achieved by a double substitution reaction with sulfur trioxide. Example B shows a glycin substituted mono methoxy benzohydroquinone that was achieved by the nucleophilic attack of an glycin to the methoxy benzoquinone paired with the sulfonated anthraquinone. In example C a isonicotinic acid substituted benzohydroquinone is paired with the same anthraquinone. The isonicotinic acid was introduced by nucleophilic attack as well.

TABLE 4

Pairings for modified products in a fully organic redox flow battery

A
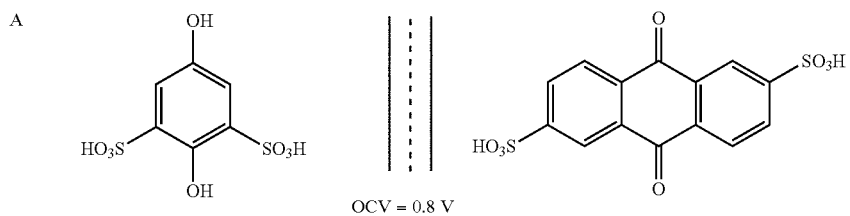
OCV = 0.8 V

B
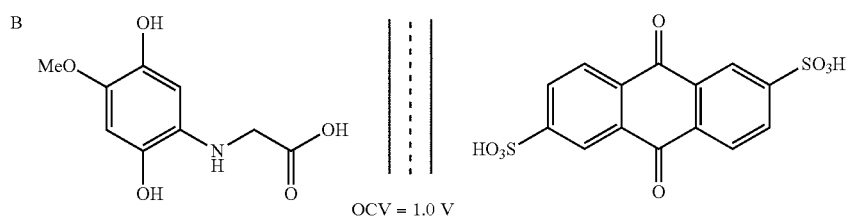
OCV = 1.0 V

C
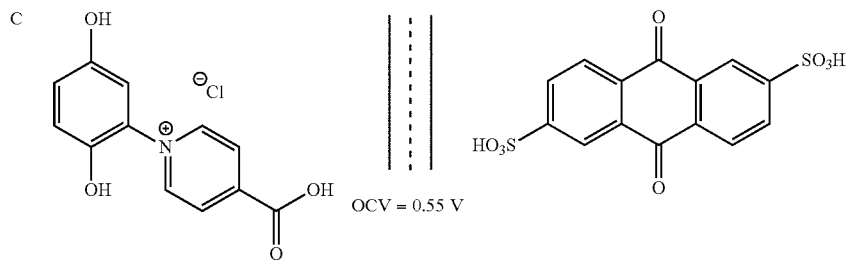
OCV = 0.55 V

The invention claimed is:

1. A method for treating lignocellulosic material, comprising:
   1) Providing and optionally preparing a process stream A comprising lignocellulosic material;
   2) subjecting said process stream A comprising lignocellulosic material to a pulping step and a separation step, thereby obtaining two separate process streams: at least one cellulose-derived process stream A, and at least one lignin-derived process stream A;
   3) further processing said at least one cellulose-derived process stream A, optionally by subjecting said cellulose-derived process stream A to one or more of the following sub-steps: washing, delignification, bleaching, chemical transformation, manufacturing of paper or paperboard, or any combination thereof;
   4) subjecting said at least one lignin-derived process stream A to at least one isolation and/or purification step, thereby obtaining at least one process stream A comprising modified lignin-derived components;
   5) subjecting said at least one lignin-derived process stream A comprising modified lignin-derived components to a chemical decomposition step, wherein the chemical decomposition step comprises oxidative cracking, reductive cracking or electro-oxidation of said modified lignin-derived components, thereby obtaining at least one lignin-derived process stream A comprising low molecular weight aromatic lignin-derived compounds;
   6) subjecting said at least one lignin-derived process stream A comprising modified lignin-derived compounds to an isolation and/or purification step, thereby obtaining at least one lignin-derived process stream A of low molecular weight aromatic lignin-derived compounds; and
   7) subjecting said at least one lignin-derived process stream A comprising low molecular weight aromatic lignin-derived compounds to a chemical transformation reaction, said chemical transformation reaction including at least one annulation, oxidation or substitution reaction, or any combination thereof, thereby obtaining a process stream A comprising low molecular weight aromatic lignin-derived quinone compounds, wherein the low molecular weight aromatic lignin-derived quinone compounds are optionally substituted.

2. The method according to claim 1, wherein said low molecular weight aromatic lignin-derived compounds obtained from lignin-derived process stream A correspond in structure to any one of General Formulas (1), (2) or (3):

General Formula (1)

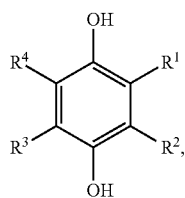
(a)

General Formula (2)

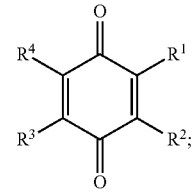
(b)

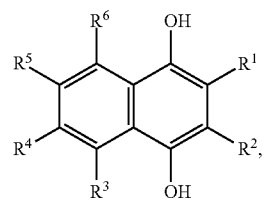
(a)

General Formula (3)

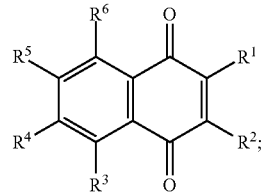
(b)

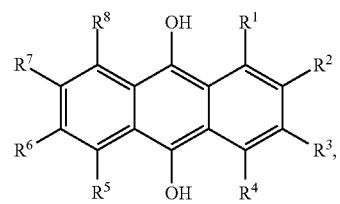
(a)

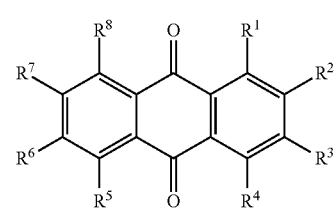
(b)

wherein each of $R^1$-$R^4$ in formula (1); $R^1$-$R^6$ in formula (2); and/or $R^1$-$R^8$ in formula (3) is independently selected from hydrogen; hydroxyl; carboxy; optionally substituted $C_{1-6}$ alkyl optionally comprising at least one heteroatom selected from N, O and S; carboxylic acids; esters; halogen; optionally substituted $C_{1-6}$ alkoxy; optionally substituted amine; amide; nitro; carbonyl; phosphoryl; phosphonyl; cyanide; and sulfonyl (—$SO_3H$).

3. The method according to claim 2, wherein at least one of $R^1$-$R^4$ in formula (1); $R^1$-$R^6$ in formula (2); and/or $R^1$-$R^8$ in formula (3) is selected from —$SO_3H$; —$C_nH_{2n}SO_3H$ optionally comprising at least one heteroatom selected from N, O and S, wherein n is an integer selected from 1, 2, 3, 4, 5, and 6; and optionally substituted amine.

4. The method according to claim 3, wherein the optionally substituted amine is selected from —$NH_2$/$NH_3^+$, —$NHR$/$NH_2R^+$, —$NR_2$/$NHR_2^+$ and —$NR_3^+$, where R is H or optionally substituted $C_{1-6}$ alkyl optionally comprising at least one heteroatom selected from N, O and S.

5. The method according to claim 4, wherein the optionally substituted $C_{1-6}$alkyl optionally comprising at least one heteroatom selected from N, O and S is selected from —$C_nH_{2n}$OH, —$C_nH_{2n}$NH$_2$, —$C_nH_{2n}$NR$_2$, —$C_nH_{2n}$CO$_2$H and —$C_nH_{2n}$SO$_3$H, wherein n is an integer selected from 1, 2, 3, 4, 5, and 6, and where R is H or optionally substituted $C_{1-6}$ alkyl optionally comprising at least one heteroatom selected from N, O and S.

6. The method according to claim 1, wherein in 1) preparing a process stream A comprising lignocellulosic material comprises debarking, chopping, grinding, crushing, milling, cleaning, refining and/or screening said lignocellulosic material.

7. The method according to claim 1, wherein said lignocellulosic material is derived from soft- or hardwoods.

8. The method according to according to claim 1, wherein in 2) the pulping step is a chemical pulping process selected from the group consisting of kraft (sulphate) pulping, sulphite pulping, and organosolv pulping.

9. The method according to claim 8, wherein the Kraft (sulphate) pulping comprises:
treating the lignocellulosic material with an aqueous alkaline solution comprising a Kraft pulping reactive agent selected from the group consisting of a sulfide agent, a sulfhydryl agent, and a polysulfide agent and a sulfate salt;
cooking the lignocellulosic material in said aqueous alkaline solution; and
optionally separating the cellulose-derived fraction and lignin-derived fraction to obtain the at least one cellulose-derived process stream A, and the at least one lignin-derived process stream A.

10. The method according to claim 1, wherein the delignification and/or bleaching of the cellulose-derived process stream A in step 3) comprises: oxygen (pre-)bleaching; chlorine prebleaching, chlorine dioxide and chlorine prebleaching, chlorine dioxide bleaching, alkaline extraction, ozone bleaching, chelating agent treatment, hydrogen peroxide bleaching, peracid treatment, or any combination thereof.

11. The method according to claim 1, wherein the chemical transformation of the cellulose-derived process stream A in step 3) comprises the preparation of rayon fibers and/or cellulose derivatives.

12. The method according to claim 11, wherein the preparation of rayon fibers comprises the following sub-steps:
(a) treatment of pulp with alkaline agent;
(b) optionally beating the pulp;
(c) contacting the pulp with carbon dioxide, thereby obtaining a "viscose solution" of cellulose xanthate;
(d) contacting the cellulose xanthate obtained from step (c) with an alkaline agent;
(e) optionally filtering, deaerating and/or ripening of the cellulose xanthate obtained from step (d)
(f) treatment with sulfuric acid, optionally by extrusion through a spinnerette into a HCl solution; and
(g) obtaining rayon fibers.

13. The method according to claim 12, wherein the treatment of pulp with an alkaline agent step comprises a mercerization treatment of the pulp with sodium hydroxide.

14. The method according to claim 11, wherein the cellulose derivative is carboxymethylcellulose (CMC), and its preparation comprises the following sub-steps:
(a) optionally beating the pulp;
(b) treatment with an alkaline agent;
(c) treatment with sodium monochloroacetate;
(d) neutralization, optionally with an acidic agent;
(e) optionally washing, beating and/or drying; and
(f) obtaining CMC.

15. The method according to claim 14, wherein the treatment with an alkaline agent step comprises a mercerization treatment with sodium hydroxide.

16. The method according to claim 1, wherein in 4) isolation and/or purification of the lignin-derived stream A comprises subjecting the lignin-derived stream A to extraction, countercurrent flow, stripping, ion-exchange, precipitation by a di- or multivalent cation, precipitation by $CO_2$ in acidic solution, filtration, or any combination thereof.

17. The method according to claim 1, further comprising in step 5) subjecting at least one further process stream A comprising modified lignin-derived components to oxidative cracking for chemical decomposition, thereby obtaining at least one lignin-derived process stream of low molecular weight aromatic lignin-derived compounds.

18. The method according to claim 17, wherein oxidative cracking is carried out in the presence of an oxidizing agent and a heterogenous or homogenous catalyst comprising a metal ion selected from Co(II), Cu(II) and Fe(III) or a metalloid component selected from B(III), Si(IV) and Al(III).

19. The method according to claim 1, wherein in step 6) isolation and/or purification comprises at least one sub-step of ultrafiltration and/or nanofiltration.

20. The method according to claim 1, wherein chemical transformation in step 7) comprises an annulation, oxidation and/or substitution reaction, or any combination thereof.

21. The method according to claim 20, wherein the substitution reaction is a sulfonation reaction.

22. The method according to claim 1, further comprising a step 8) of providing a low molecular weight aromatic lignin-derived compound, wherein step 8) optionally includes at least one purification step optionally comprising solid phase extraction or fluid-fluid phase extraction.

23. The method according to claim 22, wherein the low molecular weight aromatic lignin-derived compound is a sulfonated low molecular weight aromatic lignin-derived quinone compound.

24. The method according to claim 1, further comprising at least one step of separating a further process stream from the process stream A comprising lignocellulosic material, optionally prior to or after step 1), after step 2), after step 4), after step 5), or step 6).

25. The method according to claim 24, wherein said at least one further process stream is subjected to:
Pyrolysis and optionally catalytic upgrading (process stream B);
Catalytic oxidation (process stream C);
Catalytic cracking and/or hydrolysis (process stream D);
Catalytic reduction (process stream E);
Enzymatic conversion (process stream F); and/or
Further reactions and processes (process stream G);
or any combination thereof.

26. The method according to claim 25, wherein one or more of the following are satisfied:
the pyrolysis and optionally catalytic upgrading (process stream B) is used to additionally obtain pyrolysis oil, and optionally benzenes, toluenes, xylenes, naphthalenes, polycyclic aromatic hydrocarbons, and derivatives thereof;
the catalytic oxidation (process stream C) is used to additionally obtain specific aromatic alcohols, aldehydes, carboxylic acids, ketones, phenols, and other specially functionalized aromatics;

the catalytic cracking and/or hydrolysis (process stream D) is used to additionally obtain aromatic or aliphatic hydrocarbons;

the catalytic reduction (process stream E) is used to additionally obtain simple aromatics and cycloalkanes;

the enzymatic conversion (process stream F) is used to additionally obtain low molecular weight compounds; and the reactions and processes (process stream G) are used to additionally obtain carbon fibers, phenol-formaldehyde adhesives, polyurethane foams and elastomers, porous carbon, ethanol, lignosulfonates, and/or lignin radiation products.

* * * * *